(12) United States Patent
Gilbert et al.

(10) Patent No.: US 11,129,892 B1
(45) Date of Patent: Sep. 28, 2021

(54) VACCINE COMPOSITIONS COMPRISING ENDOGENOUS GAG POLYPEPTIDES

(71) Applicant: VNV Newco Inc., New York, NY (US)

(72) Inventors: Zachary Gilbert, Brooklyn, NY (US); Colin Malone, Brooklyn, NY (US)

(73) Assignee: VNV NEWCO INC., New York, NY (US)

( * ) Notice: Subject to any disclaimer, the term of this patent is extended or adjusted under 35 U.S.C. 154(b) by 0 days.

(21) Appl. No.: 16/876,731

(22) Filed: May 18, 2020

(51) Int. Cl.
| | |
|---|---|
| C12N 15/113 | (2010.01) |
| C12Q 1/6886 | (2018.01) |
| G01N 33/574 | (2006.01) |
| A61K 31/713 | (2006.01) |
| A61K 45/06 | (2006.01) |
| A61K 39/385 | (2006.01) |
| A61K 39/215 | (2006.01) |
| A61K 39/145 | (2006.01) |
| A61P 31/14 | (2006.01) |
| A61K 39/00 | (2006.01) |

(52) U.S. Cl.
CPC .......... *A61K 39/385* (2013.01); *A61K 39/145* (2013.01); *A61K 39/215* (2013.01); *A61P 31/14* (2018.01); *A61K 2039/6031* (2013.01); *A61K 2039/64* (2013.01); *C12N 2770/20034* (2013.01); *C12N 2770/20071* (2013.01)

(58) Field of Classification Search
CPC ............ C12Q 2600/158; C12Q 1/6886; C12Q 2600/16; C12N 15/113; C12N 2320/30
See application file for complete search history.

(56) References Cited

U.S. PATENT DOCUMENTS

| | | | |
|---|---|---|---|
| 4,510,245 A | 4/1985 | Cousens et al. | |
| 4,897,355 A | 1/1990 | Eppstein et al. | |
| 4,968,615 A | 11/1990 | Koszinowski et al. | |
| 5,168,062 A | 12/1992 | Stinski | |
| 6,919,438 B1 | 7/2005 | Alliel et al. | |
| 7,442,550 B1 | 10/2008 | Mallet et al. | |
| 7,534,439 B2 | 5/2009 | Alliel et al. | |
| 8,318,173 B2 * | 11/2012 | August ................... | A61P 15/18 424/185.1 |
| 8,518,694 B2 | 8/2013 | Hardy et al. | |
| 8,597,657 B2 | 12/2013 | Renard et al. | |
| 9,254,311 B2 | 2/2016 | Bancel et al. | |
| 9,481,905 B2 | 11/2016 | Chen et al. | |
| 9,555,091 B2 | 1/2017 | Kim et al. | |
| 9,827,332 B2 | 11/2017 | Bancel et al. | |
| 2019/0240351 A1 | 8/2019 | Bancel et al. | |
| 2019/0300902 A1 | 10/2019 | Galy | |

FOREIGN PATENT DOCUMENTS

| | | |
|---|---|---|
| CA | 2331923 C | 2/2014 |
| CA | 2383877 C | 4/2014 |
| CN | 101952436 B | 3/2013 |
| CN | 109563139 A | 4/2019 |
| EP | 1090122 B1 | 7/2008 |
| EP | 2241626 A2 | 10/2010 |
| EP | 2385058 B1 | 11/2013 |
| EP | 2241626 B1 | 1/2016 |
| JP | 4283475 B2 | 6/2009 |
| JP | 4824731 B2 | 11/2011 |
| JP | 5309159 B2 | 10/2013 |
| JP | 2019514369 A | 6/2019 |
| KR | 101164602 B1 | 7/2012 |
| KR | 20180135034 A | 12/2018 |
| WO | WO-2004087748 A1 | 10/2004 |
| WO | WO-2013151663 A1 | 10/2013 |
| WO | WO-2013151664 A1 | 10/2013 |
| WO | WO-2017182607 A1 | 10/2017 |
| WO | WO-2017191274 A2 | 11/2017 |
| WO | WO-2018209113 A1 | 11/2018 |
| WO | WO-2018234576 A1 | 12/2018 |
| WO | WO-2019077149 A1 | 4/2019 |
| WO | WO-2019077150 A1 | 4/2019 |
| WO | WO-2019118497 A1 | 6/2019 |
| WO | WO-2020061229 A2 | 3/2020 |

OTHER PUBLICATIONS

Zhang et al., "Structural Basis of Arc Binding to Synaptic Proteins: Implications for Cognitive Disease", Neuron, 2015, 86(2):490-500.*
Pastuzyn et al., "The neuronal gene arc encodes a repurposed retrotransposon gag protein that mediates intercellular RNA transfer "., Cell, 2018, 172:275-288.*
Balvay et al. Translational control of retroviruses. Nat rev Microbiol 5(2):128-49 (2007).
Becker et al. Extracellular vesicles in cancer: cell-to-cell mediators of metastasis. Cancer Cell 30:836-848 (2016).
Bramham et al. The Arc of synaptic memory. Exp. Brain Res. 200:125-140 (2010).
Budnik et al. Extracellular vesicles round off communication in the nervous system. Nat. Rev. Neurosci. 17:160-172 (2016).
Campbell et al. In vitro assembly properties of human immunodeficiency virus type 1 Gag protein lacking the p6 domain. J. Virol. 73:2270-2279 (1999).
Carlson et al. Reconstitution of selective HIV-1 RNA packaging in vitro by membrane-bound Gag assemblies. eLife 5:e14663 (2016).
Chowdhury et al. Arc/Arg3.1 interacts with the endocytic machinery to regulate AMPA receptor trafficking. Neuron 52:445-459 (2006).
Chuong et al. Regulatory activities of transposable elements: from conflicts to benefits. Nat. Rev. Genet. 18:71-8 (2017).
Comas-Garcia et al. On the selective packaging of genomic RNA by HIV-1. Viruses 8(9):246 (2016).

(Continued)

*Primary Examiner* — Barry A Chestnut
(74) *Attorney, Agent, or Firm* — Wilson Sonsini Goodrich & Rosati

(57) ABSTRACT

Described herein is a composition comprising: 1) an ARC polypeptide or an endogenous gag (endo-gag) polypeptide; 2) a pathogen-associated antigen; and 3) an adjuvant. Also described herein are vaccines and methods of vaccination using compositions comprising: 1) an ARC polypeptide or an endogenous gag (endo-gag) polypeptide; 2) a pathogen-associated antigen; and 3) an adjuvant.

23 Claims, 5 Drawing Sheets

Specification includes a Sequence Listing.

(56) References Cited

OTHER PUBLICATIONS

Cornelis et al. Retro-viral envelope gene captures and syncytin exaptation for placentation in marsupials. PNAS USA 112:E487-E496 (2015).
De Solis et al. Is Arc mRNA unique: a search for mRNAs that localize to the distal dendrites of dentate gyrus granule cells following neural activity. Front. Mol. Neurosci. 10:314 (2017).
Feigner et al. Lipofection: A Highly Efficient, Lipid-Mediated DNA-Transfection Procedure. PNAS USA 84(21): 7413-7417 (1987).
Feschotte et al. Endogenous viruses: insights into viral evolution and impact on host biology. Nat. Rev. Genet. 13:283-296 (2012).
Freed. HIV-1 assembly, release and maturation. Nat. Rev. Microbiol. 13:484-496 (2015).
Ganser et al. Assembly and analysis of conical models for the HIV-1 core. Science 283:80-83 (1999).
Gibson et al. Enzymatic assembly of DNA molecules up to several hundred kilobases. Nat Methods. 6(5):343-5 (2009).
Greer et al. The Angelman syndrome protein Ube3A regulates synapse development by ubiquitinating arc. Cell 140:704-716 (2010).
Guzowski et al. Environment-specific expression of the immediate-early gene Arc in hippo-campal neuronal ensembles. Nat. Neurosci. 2:1120-1124 (1999).
Guzowski et al. Inhibition of activity-dependent arc protein expression in the rat hippocampus impairs the maintenance of long-term potentiation and the consolidation of long-term memory. J. Neurosci. 20:3993-4001 (2000).
Hamann et al. Foamy virus protein-nucleic acid interactions during particle morphogenesis. Viruses 8(9):243 (2016).
Hansen et al. Ty3 GAG3 and POL3 genes encode the components of intracellular particles. J. Virol. 66:1414-1424 (1992).
Heraud-Farlow et al. The multifunctional Staufen proteins: conserved roles from neurogenesis to synaptic plasticity. Trends Neurosci. 37:470-479 (2014).
Irie et al. Cognitive Function Related to the Sirh11/Zcchc16 Gene Acquired from an LTR Retro-transposon in Eutherians. PLoS Genet. 11:e1005521 (2015).
Kaneko-Ishino et al. The role of genes domesticated from LTR retrotransposons and retroviruses in mammals. Front. Microbiol. 3:262 (2012).
Korkut et al. Trans-synaptic transmission of vesicular Wnt signals through Evi/Wntless. Cell 139:393-404 (2009).
Kraft et al. Visual experience sculpts whole-cortex spontaneous infraslow activity patterns through an Arc-dependent mechanism. PNAS USA 114:E9952-E9961 (2017).
Kutluay et al. Global changes in the RNA binding specificity of HIV-1 gag regulate virion genesis. Cell 159:1096-1109 (2014).
Lachenal et al. Release of exosomes from differentiated neurons and its regulation by synaptic glutamatergic activity. Mol. Cell. Neurosci. 46:409-418 (2011).
Lefebvre et al. Comparative transcriptomic analysis of human and *Drosophila* extracellular vesicles. Sci. Rep. 6:27680 (2016).
Macia et al. Dynasore, a cell-permeable inhibitor of dynamin. Dev. Cell 10:839-850 (2006).
Mailler et al. The life-cycle of the HIV-1 Gag-RNA complex. Viruses 8(9):248 (2016).
Malik et al. Poised for contagion: evolutionary origins of the infectious abilities of invertebrate retroviruses. Genome Res. 10:1307-1318 (2000).
Managò et al. Genetic disruption of Arc/Arg3.1 in mice causes alterations in dopamine and neurobehavioral phenotypes related to schizophrenia. Cell Rep. 16:2116-2128 (2016).
Mattei et al. Retrovirus maturation—an extraordinary structural transformation. Curr. Opin. Virol. 18:27-35 (2016).
McCurry et al. Loss of Arc renders the visual cortex impervious to the effects of sensory experience or deprivation. Nat. Neurosci. 13:450-457 (2010).
Mikuni et al. Arc/Arg3.1 is a postsynaptic mediator of activity-dependent synapse elimination in the developing cerebellum. Neuron 78:1024-1035 (2013).

Mokany et al. MNAzymes, a versatile new class of nucleic acid enzymes that can function as biosensors and molecular switches. J Am Chem Soc 132(2):1051-1059 (2010).
Mouland et al. The double-stranded RNA-binding protein Staufen is incorporated in human immunodeficiency virus type 1: evidence for a role in genomic RNA encapsidation. J. Virol. 74:5441-5451(2000).
Naville et al. Not so bad after all: retroviruses and long terminal repeat retrotransposons as a source of new genes in vertebrates. Clin Microbiol Infect 22(4):312-323 (2016).
NCBI, GenBank accession No. NP_001269464.1, 'paraneoplastic antigen Ma3 isoform 2 [*Homo sapiens* ]' (Jun. 30, 2018).
NCBI, GenBank accession No. XP_018887452.1, 'activity-regulated cytoskeleton-associated protein [Gorilla gorilla gorilla]' (Nov. 4, 2016).
NCBI, Gen Bank accession No. XP_020755692.1, 'activity-regulated cytoskeleton-associated protein [Odocoileus virginianus texanus ]' (Apr. 28, 2017).
Nolte-'T Hoen et al. Extracellular vesicles and viruses: Are they close relatives? PNAS USA 113:9155-9161 (2016).
Okuno et al. Inverse synaptic tagging of inactive synapses via dynamic interaction of Arc/Arg3.1 with CaMKIIβ. Cell 149:886-898 (2012).
Park et al. Elongation factor 2 and fragile X mental retardation protein control the dynamic translation of Arc/Arg3.1 essential for mGluR-LTD. Neuron 59:70-83 (2008).
Pastuzyn et al. Activity-dependent Arc expression and homeostatic synaptic plasticity are altered in neurons from a mouse model of Angelman syndrome. Front. Mol. Neurosci. 10:234 (2017).
PCT/US2018/032105 International Search Report and Written Opinion dated Aug. 1, 2018.
PCT/US2019/051786 International Search Report and Written Opinion dated Mar. 20, 2020.
Pinkstaff et al. Internal initiation of translation of five dendritically localized neuronal mRNAs. PNAS USA 98:2770-2775 (2001).
Plath et al. Arc/Arg3.1 is essential for the consolidation of synaptic plasticity and memories. Neuron 52:437-444 (2006).
Purcell et al. A poly-genic burden of rare disruptive mutations in schizophrenia. Nature 506:185-190 (2014).
Purdy et al. Critical role of conserved hydrophobic residues within the major homology region in mature retroviral capsid assembly. J. Virol. 82:5951-5961 (2008).
Rajendran et al. Alzheimer's disease β-amyloid peptides are released in association with exosomes. PNAS USA 103:11172-11177 (2006).
Raposo et al. Extracellular vesicles: exosomes, microvesicles, and friends. J. Cell Biol. 200:373-383 (2013).
Shepherd et al. Arc/Arg3.1 mediates homeostatic synaptic scaling of AMPA receptors. Neuron 52:475-484 (2006).
Shepherd et al. New views of Arc, a master regulator of synaptic plasticity. Nat. Neurosci. 14:279-284 (2011).
Smit. Interspersed repeats and other mementos of transposable elements in mammalian genomes. Curr. Opin. Genet. Dev. 9:657-663 (1999).
Steward et al. Synaptic activation causes the mRNA for the IEG Arc to localize selectively near activated postsynaptic sites on dendrites. Neuron 21:741-751 (1998).
Taylor et al. A comparative analysis of the foamy and ortho virus capsid structures reveals an ancient domain duplication. BMC Struct. Biol. 17(1):3 (2017).
Tkach et al. Communication by extracellular vesicles: where we are and where we need to go. Cell 164:1226-1232 (2016).
Topuzoğ ullari et al. An insight into the epitope-based peptide vaccine design strategy and studies against COVID-19. Turk J. Biol 44(3):215-227 (2020).
Ufer et al. Arc/Arg3.1 governs inflammatory dendritic cell migration from the skin and thereby controls T cell activation. Sci. Immunol. 1:eaaf8665 (2016).
Valadi et al. Exosome-mediated transfer of mRNAs and microRNAs is a novel mechanism of genetic exchange between cells. Nat. Cell Biol. 9:654-659 (2007).
Vlach et al. Structural and molecular determinants of HIV-1 Gag binding to the plasma membrane. Front Microbiol 6:232 (2015).

(56) References Cited

OTHER PUBLICATIONS

Wang et al. In vivo two-photon imaging reveals a role of arc in enhancing orientation specificity in visual cortex. Cell 126:389-402 (2006).
Waung et al. Rapid translation of Arc/Arg3.1 selectively mediates mGluR-dependent LTD through persistent increases in AMPAR endocytosis rate. Neuron 59:84-97 (2008).
Wu et al. Arc/Arg3.1 regulates an endosomal pathway essential for activity-dependent b-amyloid generation. Cell 147:615-628 (2011).
Yoshida et al. SARS-CoV-2-induced humoral immunity through B cell epitope analysis and neutralizing activity in COVID-19 infected individuals in Japan. bioRxiv (2020).
Zappulli et al. Extracellular vesicles and intercellular communication within the nervous system. J. Clin. Invest. 126:1198-1207 (2016).
Zhou et al. Novel reference genes for quantifying transcriptional responses of *Escherichia coli* to protein overexpression by quantitative PCR. BMC Mol. Biol. 12:18 (2011).
Altschul et al. Basic local alignment search tool. J Mol Biol 215(3):403-410 (1990).
An et al. Envelope gene of the human endogenous retrovirus HERV-W encodes a functional retrovirus envelope. J. Virol. 75:3488-3489 (2001).
Antony et al. The human endogenous retrovirus envelope glycoprotein, Syncytin-1, regulates neuroinflammation and its receptor expression in multiple sclerosis: a role for endoplasmic reticulum chaperones in astrocytes. J Immunology 179(2):1210-1224 (2007).
Ashley et al. Retrovirus-like Gag protein Arc1 binds RNA and traffics across synaptic boutons. Cell 172:262-274 (2018).
Campillos et al. Computational characterization of multiple Gag-like human proteins. Trends Genet. 22(11):585-9 (2006).
Day et al. Arc: Building a bridge from viruses to memory. Biochem. J. 469(1):eI-e3 (2015).
Delamarre et al. A Novel Human T-leukemia Virus Type 1 Cell-To-Cell Transmission Assay Permits Definition of SU Glycoprotein Amino Acids Important for Infectivity. J. Virol. 71(1):259-266 (1997).
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87: 2264-2268 (1990).
Lavillette et al. The envelope glycoprotein of human endogenous retrovirus type W uses a divergent family of amino acid transporters/cell surface receptors. J. Virol. 76:6442-6452 (2002).
Li et al. Cell culture processes for monoclonal antibody production. Mabs. 2(5):466-477 (2010).
Myrum et al. Arc is a flexible modular protein capable of reversible self-oligomerization. Biochem. J. 468(1):145-158 (2015).
Pastuzyn et al. The Neuronal Gene Arc Encodes a Repurposed Retrotransposon Gag Protein that Mediates Intercellular RNA Transfer. Cell 172:275-288 (2018).
Rosenberg et al. Early Assembly Step of a Retroviral Envelope Glycoprotein: Analysis Using a Dominant Negative Assay. J. Cell Biol. 145:57-68 (1999).
Zhang et al. Structural Basis of Arc Binding to Synaptic Proteins: Implications for Cognitive Diseases. Neuron 86(2):490-500 (2015).

\* cited by examiner

FIG. 2A
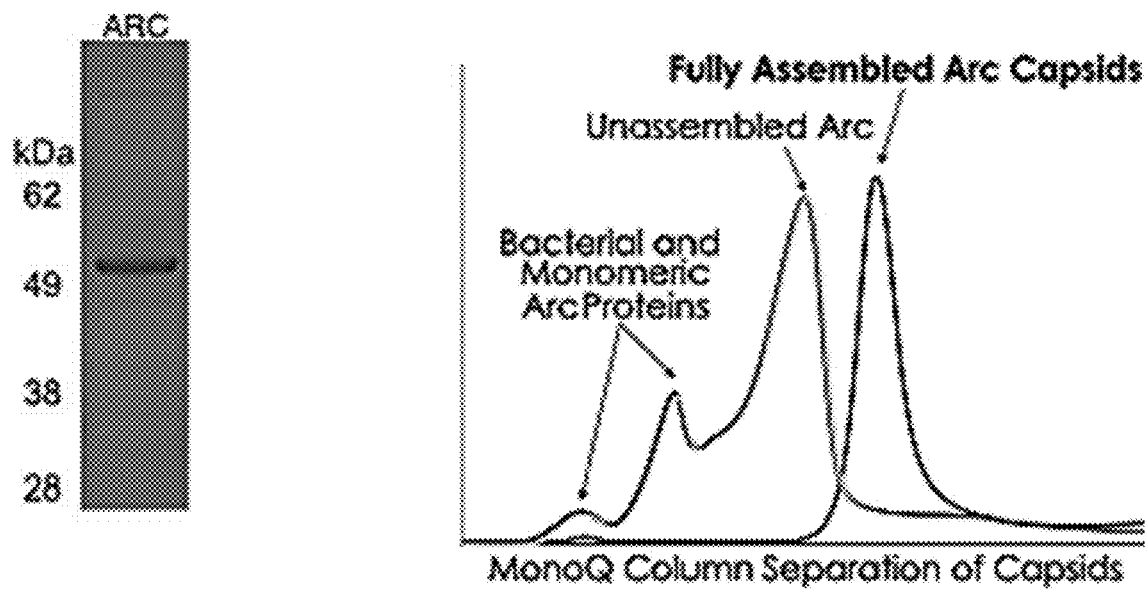
FIG. 2B
FIG. 2C
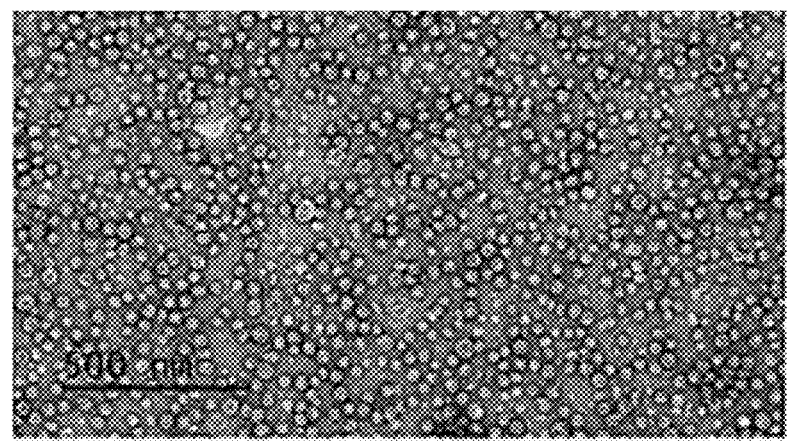
FIG. 2D

VACCINE COMPOSITIONS COMPRISING ENDOGENOUS GAG POLYPEPTIDES

SEQUENCE LISTING

The instant application contains a Sequence Listing which has been submitted electronically in ASCII format and is hereby incorporated by reference in its entirety. Said ASCII copy, created on Jun. 29, 2020, is named 54838-708_201_SL.txt and is 76,573 bytes in size.

SUMMARY

Described herein are vaccine compositions, methods of vaccinating using the compositions, and methods of making the compositions. Such compositions are useful for the vaccination of individuals against pathogenic diseases caused by bacteria, viruses, fungi, or parasites.

The compositions described herein are virus-like particles (VLPs) that display antigens and/or adjuvants. These VLPs comprise endogenous Gag-like polypeptides such as ARC polypeptides and are sometimes referred to as endogenous virus-like particles (endo-VLPs). When a human individual is the one vaccinated, the ARC polypeptides may comprise human ARC or other human endogenous Gag (endo-Gag) polypeptides. The endo-VLPs described herein provide advantages compared to known methods of vaccination.

Previous methods of vaccination, including the use of live attenuated viruses, inactivated viruses, and recombinant subunit-based vaccines, all suffer from drawbacks. One is that engineering and attenuating live virus-based vaccines are labor and time-intensive processes. While addressing this limitation, recombinant subunit vaccines may lack potency due to the lack of viral, bacterial, or other contexts that leads to adequate immune priming or boosting. Nanoparticle vaccines offer a potential solution to this limitation when using recombinant proteins for vaccine production. By introducing antigens, agonists for innate immune receptors, and/or adjuvants together on a single nanoparticle, one can leverage the benefits of a recombinant vaccine in a package that appears to the immune system to be a virus. When antigen and adjuvant molecules are mere nanometers apart on a single nanoparticle, the likelihood of immune cell recognition of both is greatly increased. This combination of benefits makes recombinant antigen delivery using endoVLP delivery systems a rapid approach to developing effective vaccines targeting emerging threats to human health. Further, the use of endoVLPs based upon human ARC and other human Gag-like proteins allows for a platform amenable to repeated administration since an immune response is not generated against the endoVLPs.

In one embodiment, a composition comprises: 1) an ARC polypeptide or an endogenous gag (endo-gag) polypeptide; 2) a pathogen-associated antigen; and 3) an adjuvant.

In some embodiments, the composition comprises an ARC polypeptide comprising an amino acid sequence that is SEQ ID NO: 1 or an amino acid sequence that is at least 90% identical to SEQ ID NO: 1. In some embodiments, the endo-gag polypeptide comprises an amino acid that is SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28. In other embodiments, the endo-gag polypeptide comprises an amino acid sequence that is at least 90% identical to SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28. In some instances, the endo-gag polypeptide comprises any combination of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments, the pathogen-associated antigen and the adjuvant are different compounds or polypeptides. In one embodiment, the pathogen-associated antigen comprises a polypeptide. In some embodiments, the pathogen-associated antigen is a bacterial antigen, a fungal antigen, a parasitic antigen, or a viral antigen. In one embodiment, the pathogen-associated antigen is a bacterial antigen. In another embodiment, the pathogen-associated antigen is a fungal antigen. In one instance, the pathogen-associated antigen is a parasitic antigen. In another instance, the pathogen-associated antigen is a viral antigen. In one embodiment, the viral antigen is a respiratory virus antigen. In another embodiment, the viral antigen is a Coronaviridae antigen. In one instance, Coronaviridae exhibits human tropism. In some embodiments, Coronaviridae is selected from the list consisting of SARS Coronavirus (SARS-CoV-1), COVID-19 (SARS-CoV-2), MERS-coronavirus (MERS-CoV), or any combination thereof.

In some embodiments, the viral antigen comprises a spike protein, an envelope protein, a nucleocapsid protein, a membrane protein, a membrane glycoprotein, or a non-structural protein. In other embodiments, the viral antigen comprises a SARS Coronavirus (SARS-CoV-1) antigen, a COVID-19 (SARS-CoV-2) antigen, a MERS-coronavirus (MERS-CoV) antigen, or any combination thereof. In some instances, the viral antigen comprises a spike protein, an envelope small membrane protein, a membrane protein, a non-structural protein 6 (NSP6), a nucleoprotein, an ORF10 protein, Protein 3a, Protein7a, Protein 9b, structural protein 8, uncharacterized protein 4, or any combination thereof. In some embodiments, the viral antigen comprises an amino acid residue sequence as set forth in any one of SEQ ID NOs: 30 to 42, and combinations thereof. In other embodiments, the viral antigen consists of an amino acid residue sequence as set forth in any one of SEQ ID NOs: 30 to 42, and combinations thereof. In some embodiments, the viral antigen is an Influenza antigen. In some embodiments, the Influenza antigen is an M1 matrix protein. In some embodiments, the M1 matrix protein is derived from influenza H5N1 and/or comprises SEQ ID NO: 45 or a fragment thereof.

In some embodiments, the ARC polypeptide or the endo-gag-polypeptide is coupled to the pathogen-associated antigen. In one embodiment, the ARC polypeptide or the endo-gag-polypeptide is coupled to the pathogen-associated antigen by a peptide bond. In another embodiment, the pathogen-associated antigen is N-terminal to the ARC polypeptide or the endo-gag-polypeptide. In one instance, the pathogen-associated antigen is C-terminal to the ARC polypeptide or the endo-gag-polypeptide. In another instance, a flexible peptide linker separates the pathogen-associated antigen and the ARC polypeptide or the endo-gag-polypeptide. In one embodiment, the ARC polypeptide or the endo-gag-polypeptide is coupled to the pathogen-associated antigen by a bond formed from the reaction of an NETS-ester and a primary amine of the ARC polypeptide.

In some embodiments, the adjuvant comprises an immune stimulatory compound. In other embodiments, the immune stimulatory compound comprises a lipid, a nucleic acid, an aluminum compound, an water-in-oil emulsion, a polypeptide, or any combination thereof. In one embodiment, the immune stimulatory compound comprises a lipid. In other embodiments, the immune stimulatory compound comprises a nucleic acid. In one embodiment, the nucleic acid is a DNA. In some embodiments, the DNA comprises CPG-1018, CPG-1826, CPG-2007, CPG-2006, or any combination thereof. In another embodiment, the nucleic acid is an RNA. In some embodiments, the RNA comprises CV1802, Poly(U), Poly(I:C), ssRNA40, GFP RNA, RNA41, RNA42, RNA33, RNA35, 5'-phosphorylated blunt ended viral genomic dsRNA <300 bp, long dsRNA >1000 bp, genomic ssRNA, ssRNA40, or any combination thereof. In other embodiments, the immune stimulatory compound comprises an aluminum compound. In some instances, the aluminum compound comprises alum. In some embodiments, the immune stimulatory compound comprises an water-in-oil emulsion. In other embodiments, the immune stimulatory compound comprises an agonist for a toll-like receptor, a NOD-like receptor, a RIG-1 or MDA-5 receptor, a C-type lectin receptor, a costimulatory molecule, a cytokine receptor, a STING pathway, or any combination thereof. In some instances, the toll-like receptor agonist is selected from the list consisting of CpG oligonucleotide, SD-101, LFX453, imiquimod, Bacillus Calmette-Guérin (BCG), monophosphoryl lipid A, Poly ICLC, GSK1795091, or any combination thereof. In some embodiments, the NOD-like receptor agonist is selected from the list consisting of bacterial peptidoglycan, an acylated derivative of iE-DAP (C12-iE-DAP), D-gamma-Glu-mDAP (iE-DAP), L-Ala-gamma-D-Glu-mDAP (Tri-DAP), muramyl dipeptide (MDP), muramyl tripeptide, L18-MDP, M-TriDAP, murabutide, PGN-ECndi, PGN-ECndss, PGN-SAndi, N-glycosylated muramyl dipeptide, murabutide, or any combination thereof. In other embodiments, the RIG-1 or MDA-5 receptor agonist is selected from the list consisting of poly(I:C), Poly (dA:dT), Poly(dG:dC), 3p-hpRNA, 5'ppp-dsRNA, or any combination thereof. In some instances, the C-type lectin receptor agonist is selected from the list consisting of Beta-1,3-glucan, zymosan, Heat-killed *C. albicans*, cord factor, and Trehalose-6,6-dibehenate, or any combination thereof. In one embodiment, the immune stimulatory compound comprises a polypeptide. In some embodiments, the polypeptide is a polypeptide from *Brucella abortus, Bordetella pertussis, Chlamydia trachomatis, Fusobacterium nucleatum, Mycobacterium tuberculosis, Neisseria meningitidis, Staphylococcus aureus, Shigella dysenteriae, Shigella flexneri, Streptococcus pneumoniae, Vibrio cholerae, Brucella abortus, Mycobacterium paratuberculosis, Neisseria meningitidis, Streptococcus pneumoniae*, or any combination thereof. In other embodiments, the polypeptide is from BCSP31, FHA, MOMP, PorB, PVL, Porin, OmpA, 34 kDa MOMP, PepO, OmpU, Lumazine synthase, Omp16, Omp19, BCSP31, CobT, RpfE, Rv0652, HBHA, NhhA, DnaJ, Pneumolysin, AA146 Pneumolysin, or any combination thereof. In another embodiment, the polypeptide is a polypeptide from human heat shock protein 70.

In one embodiment, the adjuvant is coupled to the ARC polypeptide or the endo-gag-polypeptide. In another embodiment, the adjuvant is coupled to the ARC polypeptide or the endo-gag-polypeptide by a bond formed from the reaction of an NHS-ester and a primary amine of the ARC polypeptide. In one instance, the adjuvant is coupled to the ARC polypeptide or the endo-gag-polypeptide by a peptide bond. In another instance, the adjuvant is N-terminal to the ARC polypeptide or the endo-gag-polypeptide. In one embodiment, the adjuvant is C-terminal to the ARC polypeptide or the endo-gag-polypeptide.

In some embodiments, the composition comprises a flexible peptide linker separating the adjuvant and the ARC polypeptide or the endo-gag-polypeptide. In other embodiments, the composition comprises a virus-like particle. In some instances, the virus-like particle comprises a mixture of the ARC or the endo-gag-polypeptide polypeptide coupled to the pathogen-associated antigen and the ARC polypeptide or the endo-gag-polypeptide coupled to the adjuvant. In some embodiments, the virus-like particle comprises ARC polypeptide or the endo-gag-polypeptide not coupled to adjuvant or pathogen-associated antigen. In other embodiments, the ARC polypeptide or the endo-gag-polypeptide coupled to the adjuvant comprises from about 5% to about 20% of the virus-like particle. In some instances, the ARC polypeptide or the endo-gag-polypeptide coupled to the adjuvant comprises from about 5% to about 15% of the virus-like particle. In some embodiments, the ARC polypeptide or the endo-gag-polypeptide coupled to the adjuvant comprises about 10% of the virus-like particle. In other embodiments, the ARC polypeptide or the endo-gag-polypeptide coupled to the pathogen-associated antigen comprises from about 5% to about 20% of the virus-like particle. In some instances, the ARC polypeptide or the endo-gag-polypeptide coupled to the pathogen-associated antigen comprises from about 5% to about 15% of the virus-like particle. In some embodiments, the ARC polypeptide or the endo-gag-polypeptide coupled to the pathogen-associated antigen comprises about 10% of the virus-like particle. In other embodiments, the ARC polypeptide or the endo-gag-polypeptide not coupled to adjuvant or pathogen-associated antigen comprises from about 90% to about 60% of the virus-like particle. In some instances, the ARC polypeptide or the endo-gag-polypeptide not coupled to adjuvant or pathogen-associated antigen comprises from about 90% to about 70% of the virus-like particle. In some embodiments, the ARC polypeptide or the endo-gag-polypeptide not coupled to adjuvant or pathogen-associated antigen comprises about 80% of the virus-like particle.

In some embodiments, the composition of any one of the previous embodiments comprises a pharmaceutically acceptable excipient, carrier, or diluent. In some embodiments, the composition of any one of the previous embodiments is used as a vaccine. In some embodiments, the composition of any one of the previous embodiments is used in priming or boosting an adaptive immune response to the pathogen-associated antigen. In one embodiment, the adaptive immune response is an antibody response to the pathogen-associated antigen. In another embodiment, the antibody response produces IgG antibodies that specifically bind the pathogen-associated antigen. In one instance, the adaptive immune response is a cellular immune response to the pathogen-associated antigen.

In some embodiments, a method of priming an adaptive immune response to a pathogen-associated antigen in an individual comprises administering the composition of any one the previous embodiments to the individual, thereby priming an adaptive immune response to the pathogen-associated antigen. In one embodiment, the individual is a human individual. In another embodiment, the adaptive immune response is an antibody response to the pathogen-associated antigen. In one instance, the antibody response produces IgG antibodies that specifically bind the pathogen-associated antigen. In one embodiment, the adaptive immune response is a cellular immune response to the pathogen-associated antigen.

In some embodiments, a method of vaccinating an individual comprises administering the composition of any one of the previous embodiments to the individual, thereby vaccinating the individual. In one embodiment, the method of vaccinating protects from Coronaviridae infection or symptoms. In some embodiments, Coronaviridae comprises SARS Coronavirus (SARS-CoV-1), COVID-19 (SARS-CoV-2), MERS-coronavirus (MERS-CoV), or any combination thereof.

In some embodiments, a nucleic acid encodes the ARC polypeptide or the endo-gag-polypeptide, the ARC polypeptide or the endo-gag-polypeptide that is coupled to the pathogen-associated antigen by a peptide bond, the pathogen-associated antigen that is N-terminal to the ARC polypeptide or the endo-gag-polypeptide, the pathogen-associated antigen that is C-terminal to the ARC polypeptide or the endo-gag-polypeptide, the pathogen-associated antigen and the ARC polypeptide or the endo-gag-polypeptide separated by a flexible peptide linker, the adjuvant coupled to the ARC polypeptide or the endo-gag-polypeptide by a peptide bond, the adjuvant that is N-terminal to the ARC polypeptide or the endo-gag-polypeptide, the adjuvant that is C-terminal to the ARC polypeptide or the endo-gag-polypeptide, or the adjuvant and the ARC polypeptide or the endo-gag-polypeptide separated by a flexible peptide linker.

In some embodiments, a vector comprises the nucleic acid encoding the ARC polypeptide or the endo-gag-polypeptide, the ARC polypeptide or the endo-gag-polypeptide that is coupled to the pathogen-associated antigen by a peptide bond, the pathogen-associated antigen that is N-terminal to the ARC polypeptide or the endo-gag-polypeptide, the pathogen-associated antigen that is C-terminal to the ARC polypeptide or the endo-gag-polypeptide, the pathogen-associated antigen and the ARC polypeptide or the endo-gag-polypeptide separated by a flexible peptide linker, the adjuvant coupled to the ARC polypeptide or the endo-gag-polypeptide by a peptide bond, the adjuvant that is N-terminal to the ARC polypeptide or the endo-gag-polypeptide, the adjuvant that is C-terminal to the ARC polypeptide or the endo-gag-polypeptide, or the adjuvant and the ARC polypeptide or the endo-gag-polypeptide separated by a flexible peptide linker. In other embodiments, the vector comprises a promoter operatively coupled to the nucleic acid encoding the ARC polypeptide. In some instances, a host cell comprises the vector of the previous embodiments. In some embodiments, a method of manufacturing a vaccine comprises isolating the ARC polypeptide or the endo-gag polypeptide from the host cell of any one of the previous embodiments and contacting the polypeptide to a solution comprising a salt concentration of 100 mM to 1000 mM. In other embodiments, the salt is NaCl or NaPO4.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1A discloses SEQ ID NOS 47-48, 46 and 46, respectively, in order of appearance.

FIGS. 2A to 2D illustrate human Arc protein purification and endoVLP formation. 2A, recombinant Arc purification construct design for inducible bacterial expression of a 6×His affinity tag (SEQ ID NO: 47), 3×GS amino acid spacer (SEQ ID NO: 48), TEV protease cleavage site, and Human Arc coding sequence, excluding the initiating methionine. 2B, visualization of purified Arc protein (~50 kDa) after affinity tag cleavage using SDS denaturing gel electrophoresis followed by Coomassie staining. 2C, a graph depicting MonoQ purification of unassembled Arc protein (yellow), or Arc endoVLPs (black). 2D, negative stain electron micrograph of MonoQ purified and concentrated recombinant Arc endoVLPs.

FIG. 3A discloses "6×His" as SEQ ID NO: 47, "GSGSGS" as SEQ ID NO: 48 and "GSGSGSGSGS" as SEQ ID NO: 46. 3B, visualization of Cre-Arc fusion protein (Arc-Cre not shown) by SDS denaturing gel electrophoresis followed by Coomassie staining. 3C, western blot analysis of Arc-fusion protein after transfection of mammalian expression constructs (not shown) into HEK293T cells, probing for Arc protein, with COX IV as a loading control. 3D, TEM of ARC endoVLPs made with tagged and untagged-ARC. 3E, depiction of an N-terminal Myc-tagged Arc mammalian expression construct that was transfected into HEK293T cells and visualized both by western blot analysis probing for Arc and indirect immunofluorescence microscopy probing for Arc (Arc-transfected cells denoted by asterisks).

DETAILED DESCRIPTION

Figure 1A:
FIG. 1A illustrates a recombinant Arc construct design for purification of antigen and adjuvant tethered fusion proteins, separated by a 5×GS flexible protein linker (SEQ ID NO: 46).

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein, the term "about" refers to an amount that is near the stated amount by 10% or less.

As used herein, the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

The terms "polypeptide" and "protein" are used interchangeably to refer to a polymer of amino acid residues and are not limited to a minimum length. Polypeptides, including the provided antibodies and antibody chains and other peptides, e.g., linkers and binding peptides, may include natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known, for instance, using publicly available computer software such as BLAST, BLAST-2, ALIGN, or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., South San Francisco, Calif., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The polypeptides described herein can be encoded by a nucleic acid. A nucleic acid is a type of polynucleotide comprising two or more nucleotide bases. In certain embodiments, the nucleic acid is a component of a vector that can be used to transfer the polypeptide-encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors, and the like. In the expression vectors, regulatory elements such as promoters, enhancers, polyadenylation signals for use in controlling transcription can be derived from mammalian, microbial, viral, or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

As used herein, the terms "homologous," "homology," or "percent homology" when used herein to describe an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the polypeptides described herein can be used to infect, transfect, transform, or otherwise render a suitable cell transgenic for the nucleic acid, thus enabling the production of polypeptides for commercial or therapeutic uses. Standard cell lines and methods for the production of antibodies from a large-scale cell culture are known in the art. See e.g., Li et al., "Cell culture processes for monoclonal antibody production." Mabs. 2010 September-October; 2(5): 466-477. In certain embodiments, the cell is a eukaryotic cell. In certain embodiments, the eukaryotic cell is a mammalian cell. In certain embodiments, the mammalian cell line useful for producing antibodies is a Chines Hamster Ovary (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising a nucleic acid encoding a polypeptide described herein integrated at a genomic location; and (b) a cryoprotectant. In certain embodiments, the cryoprotectant comprises glycerol or DMSO. In certain embodiments, the master cell bank is contained in a suitable vial or container able to withstand freezing by liquid nitrogen.

Also described herein are methods of making a polypeptide described herein. Such methods comprise incubating a cell or cell-line comprising a nucleic acid encoding the polypeptide in a cell culture medium under conditions sufficient to allow for expression and secretion of the polypeptide, and further harvesting the polypeptide from the cell culture medium. The harvesting can further comprise one or more purification steps to remove live cells, cellular debris, non-polypeptide of interest proteins, undesired salts, buffers, and medium components. In certain embodiments, the additional purification step(s) include centrifugation, ultracentrifugation, protein A, protein G, protein A/G, or protein L purification, and/or ion exchange chromatography.

As used herein, the term "prime" or "priming" in reference to an immune response refers to introducing an antigen to the immune system of an individual, wherein the individual is naïve to the antigen introduced. The term "boost" or "boosting" in reference to an immune response refers to introducing an antigen to the immune system of an individual, wherein the immune system of the individual has experienced the antigen before, either through a previous vaccine administration or through natural infection.

As used herein, a "vaccine" refers to a composition of matter that is intended to prime or boost an immune response in an individual. The term "vaccinating" refers to the act of administering a vaccine to an individual. Vaccines may be administered prophylactically to prevent any disease or severe disease, or one or more unwanted symptoms such as fever, cough, sore throat, rhinorrhea, nasopharyngeal or chest congestion, respiratory distress, diarrhea, or vomiting. Vaccines may also be administered post-recovery from disease to prevent reinfection or preserve immunity gained from natural infection.

The term "adaptive immune response" as used herein refers to the components of the immune response that respond in an antigen-restricted way and encompasses cellular immune responses attributable to T lymphocytes and humoral or antibody response attributable to B cells and plasma cells. A "cellular immune response" is indicated by any one or more of the following: cytokine/chemokine release by T cells; T-cell homing to secondary lymphoid organs; T-cell proliferation; and cytotoxic T-cell responses. Several methods can be used to verify an antigen-specific cellular immune response, including ex vivo antigen stimulation assays of T lymphocytes and in vivo assays, such as tetramer staining of T lymphocytes. An "antibody response" is indicated by any one or more of the following: B cell proliferation, B-cell cytokine/chemokine release, B-cell homing to secondary lymphoid organs, antibody secretion, isotype switching to IgG type antibodies, or plasma cell differentiation. An antibody response can be verified by several methods, but a predominant method is the detection of antigen-specific antibodies in the serum or plasma of a vaccinated individual.

An "adjuvant" as described herein refers to a substance that in combination with an antigen promotes an adaptive immune response to the antigen. An "immune stimulatory compound" refers to a substance that specifically interacts with the innate immune system to initiate a "danger signal" that ultimately leads to the development of the adaptive components of the immune response (e.g., B cell, T cells). Immune stimulatory compounds include pathogen-associated molecular patterns (PAMPs) such as dsRNA, lipopolysaccharide, and CpG DNA, either naturally occurring or synthetic. Immune stimulatory compounds are agonists of various innate immune receptors including Toll-like receptors (TLRs), NOD-like receptors, RIG-1 or MDA-5 receptors, C-type lectin receptors, or the STING pathway.

A "pathogen-associated antigen" as described herein includes antigenic determinants derived from pathogenic organisms, including viruses, bacteria, fungi, or parasites capable of causing disease in an individual. Generally, such antigens will comprise polypeptides that may elicit an adaptive immune response specific for said antigen.

Coronaviridae refers to a family of enveloped, positive-sense, single-stranded RNA viruses. Coronaviridae encompass alpha-, beta-, gamma-, and delta-coronaviruses. Several coronaviruses cause disease in humans, including SARS Coronavirus (SARS-CoV-1), COVID-19 (SARS-CoV-2), and MERS-coronavirus (MERS-CoV).

Virus-like particles (VLPs) are molecules that closely resemble viruses but are non-infectious because they contain no viral genetic material. VLPs generally comprise one or more viral structural proteins (e.g., envelop, capsid, or membrane proteins) and can comprise structural proteins from different viruses. Generally, VLPs form a hollow structure that can be used to carry therapeutic payloads, such as small molecule inhibitors or non-viral nucleic acids.

ARC Based Vaccines

Arc (activity-regulated cytoskeleton-associated protein) regulates the endocytic trafficking of a-amino-3-hydroxy-5-methylisoxazole-4-propionic acid (AMP A) type glutamate receptors. Arc activities have been linked to synaptic strength and neuronal plasticity. Phenotypes of loss of Arc in experimental murine models include defective formation of long-term memory and reduced neuronal activity and plasticity. Arc exhibits similar molecular properties to retroviral Gag proteins. The Arc gene may have originated from the Ty3/gypsy retrotransposon. An endogenous Gag (endo-Gag) protein is any protein endogenous to a eukaryotic organism, including Arc, that has predicted and annotated similarity to viral Gag proteins. Exemplary endo-Gag proteins are disclosed in Campillos M, Doerks T, Shah PK, and Bork P. "Computational characterization of multiple Gag-like human proteins," *Trends Genet.* 2006 November; 22(11): 585-9.

The compositions of ARC/endo-gag proteins and endoVLPs described herein are useful to vaccinate or otherwise prime and/or boost an adaptive immune response directed against a pathogen-associated antigen. Such immune responses can prevent natural infection against a pathogen from which the antigen is derived, reduce the severity of symptoms of or the mortality associated with the pathogen, or reduce an individual's ability to act as a carrier for the pathogen.

Figure 1B:
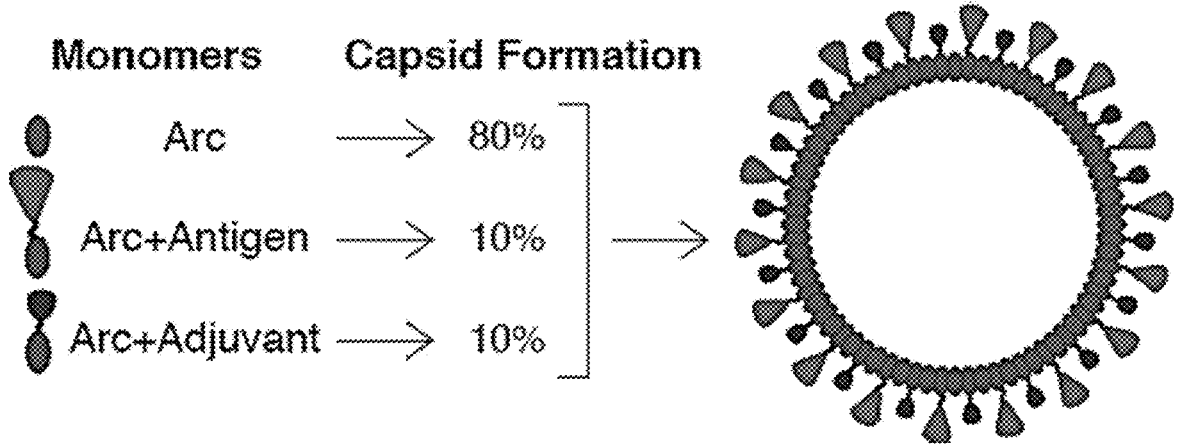
FIG. 1B illustrates a schematic outlining the mixing of endoVLP component monomers at defined ratios, followed by entry into structure formation conditions, which leads to the production of mature recombinant endoVLPs.
Figure 1C:
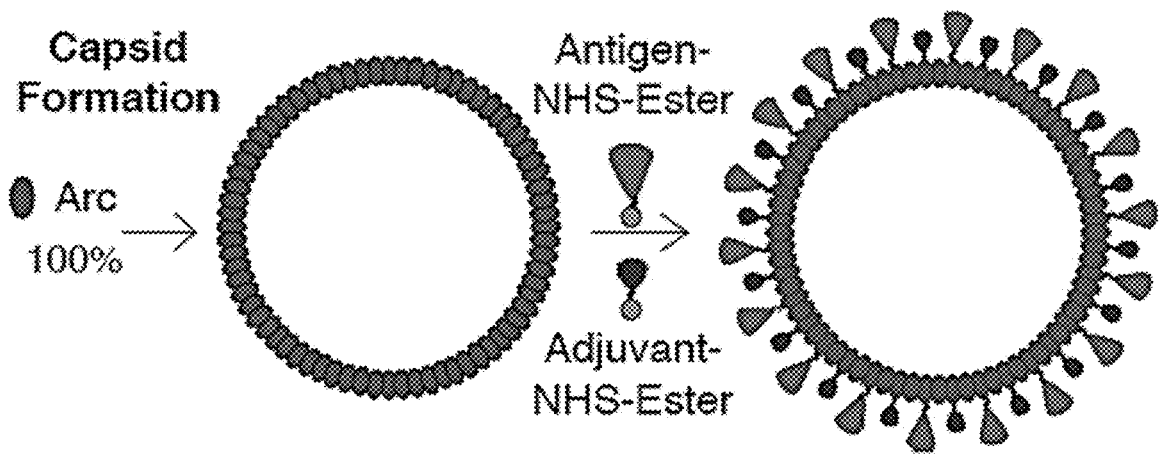
FIG. 1C illustrates a schematic outlining the production of pure Arc endoVLPs, which can then have antigen and adjuvant peptides chemically conjugated to the exposed face.
Figure 1D:
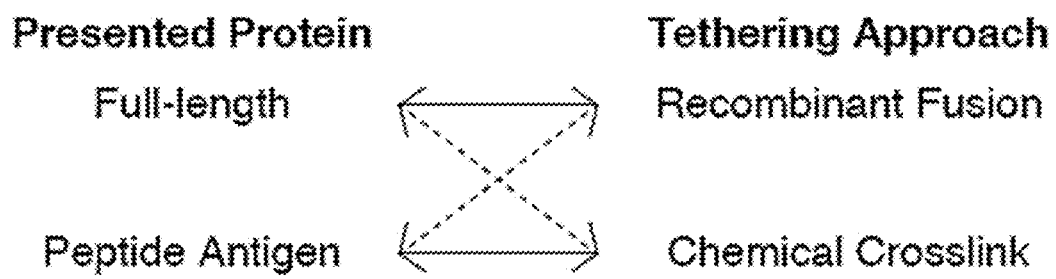
FIG. 1D illustrates the modularity of the Arc endoVLP for immune presentation and tethering approaches.

Referring to FIG. 1B, in a certain non-limiting embodiment, the vaccine compositions described herein minimally comprise an ARC/endo-gag polypeptide coupled to an adjuvant, an ARC/endo-gag polypeptide coupled to a pathogen-associated antigen, or an ARC/endo-gag polypeptide coupled to both a pathogen-associated antigen and an adjuvant. In another embodiment, the vaccine compositions comprise a first ARC/endo-gag polypeptide that is not coupled to an adjuvant or a pathogen-associated antigen; a second ARC/endo-gag polypeptide coupled to an adjuvant; and a third ARC/endo-gag polypeptide coupled to a pathogen-associated antigen. As shown in FIG. 1A, in certain embodiments, the adjuvant or pathogen-associated polypeptide is expressed as either an N- or C-terminal fusion to the ARC/endo-gag polypeptide. In certain embodiments, the fusion polypeptide optionally comprises a flexible linker between the ARC polypeptide and the adjuvant or pathogen-associated polypeptide (e.g., Gly-Ser linker). In certain embodiments, the fusion polypeptides are further expressed with a suitable purification Tag (e.g., HIS-tag) and/or a protease cleavage site (e.g., TEV protease cleavage site). In another embodiment, shown in FIG. 1C, ARC/endo-GAG polypeptides are not fusion polypeptide, but are expressed uncoupled to an adjuvant and/or pathogen-associated antigen, followed by covalent modification of the ARC/endo-gag polypeptide with an adjuvant or pathogen-associated antigen (e.g., ester linkages using NETS-ester chemistry). Finally, FIG. 1D illustrates that the approaches in 1B and 1C can be combined to achieve the optimal VLP for inducing immunity or prophylaxis to a pathogen in an individual.

The ARC/endo-gag-VLP polypeptide vaccines described herein, in certain embodiments, comprise an adjuvant coupled to an ARC polypeptide. The adjuvant may be a non-polypeptide compound such as a CpG oligonucleotide, double-stranded RNA, lipopolysaccharide, a TLR agonist, a RIG agonist, a STING agonist, or a C-type lectin receptor agonist. In such instances wherein the adjuvant is not a polypeptide, the adjuvant can be crosslinked to an ARC/endo-gag polypeptide using any suitable chemistry. In certain embodiments, the adjuvant is coupled by a crosslinking reaction after VLP formation. In certain embodiments, the adjuvant is coupled by the reaction of an NETS ester and a primary amine on the ARC/endo-gag polypeptide. In certain embodiments, the adjuvant is coupled by a peptide linkage as a fusion protein. In certain embodiments, the adjuvant is coupled by a peptide linkage N-terminal to the ARC/endo-gag polypeptide. In certain embodiments, the adjuvant is coupled by a peptide linkage C-terminal to the ARC/endo-gag polypeptide. In certain embodiments, the adjuvant and the ARC/endo-gag polypeptide are connected via a flexible polypeptide linker. In certain embodiments, the adjuvant and the ARC/endo-gag polypeptide are connected via a flexible polypeptide linker, wherein the adjuvant polypeptide is N-terminal to the ARC/endo-gag polypeptide. In certain embodiments, the adjuvant and the ARC/endo-gag polypeptide are connected via a flexible polypeptide linker, wherein the adjuvant polypeptide is C-terminal to the ARC/endo-gag polypeptide.

The ARC/endo-gag-VLP polypeptide vaccines described herein, in certain embodiments, comprise a pathogen-associated antigen coupled to an ARC/endo-gag polypeptide. In certain embodiments, the pathogen-associated antigen comprises a short polypeptide comprising 8, 9, 10, 11, 12, 13, 14, 15, 16, 17, 18, 19, 20, 21, 22, 23, 34, 25, 26, 27, 28, 29, 30, or more amino acids in length. In certain embodiments, the pathogen-associated antigen comprises a polypeptide comprising all or substantially all of an antigenic protein. In certain embodiments, the pathogen-associated antigen comprises a polypeptide comprising an antigenic domain of a protein. In certain embodiments, the pathogen-associated antigen comprises a polypeptide comprising an antigenic region of a protein. In certain embodiments, the pathogen-associated antigen comprises a polypeptide comprising two or more antigenic domains or regions of a protein, or combinations thereof. In certain embodiments, the pathogen-associated antigen comprises a polypeptide at least about 50, 75, 100, 150, 200, 250, 300, 350, 400, 450, 500, 550, 600, 650, 700, 750, 800, 850, 900, 950, 1,000, or more amino acids in length. In certain embodiments, the pathogen-associated antigen comprises a polypeptide less than about 100, 150, 200, 250, 300, 350, 400, 450, 500, 550, 600, 650, 700, 750, 800, 850, 900, 950, 1,000 amino acids in length.

In such instances wherein the pathogen-associated antigen is not a polypeptide, the pathogen-associated antigen can be crosslinked to an ARC/endo-gag polypeptide using any suitable chemistry. In certain embodiments, the pathogen-associated antigen is coupled by a crosslinking reaction after VLP formation. The cross-linking reaction can be any suitable reaction, including but not limited to, an amine-to-amine, sulfhydryl-to-sulfhydryl, amine-to-sulfhydryl, carboxyl-to-amine, or sulfhydryl-to-carboxyl. In certain embodiments, the pathogen-associated antigen is coupled by the reaction of an NHS ester and a primary amine on the ARC/endo-gag polypeptide (e.g., a lysine residue). In certain embodiments, the pathogen-associated antigen is coupled by the reaction of an imidoester and a primary amine on the ARC/endo-gag polypeptide. In certain embodiments, the pathogen-associated antigen is coupled by the reaction of a maleimide group and a sulfhydryl group (e.g., cysteine residue) on the ARC/endo-gag polypeptide. In certain embodiments, the pathogen-associated antigen is coupled by the reaction of a maleimide group and a primary amine group on the ARC/endo-gag polypeptide. In certain embodiments, the pathogen-associated antigen is coupled by the reaction of a haloacetyl group and a sulfhydryl group on the ARC/endo-gag polypeptide. In certain embodiments, the pathogen-associated antigen is coupled by the reaction of a haloacetyl group and a primary amine group on the ARC/endo-gag polypeptide. In certain embodiments, the pathogen-associated antigen is coupled by the reaction of a pyridyldithiol and a sulfhydryl group on the ARC/endo-gag polypeptide. In certain embodiments, the pathogen-associated antigen is coupled by the reaction of a pyridyldithiol and a primary amine group on the ARC/endo-gag polypeptide. In certain embodiments, the pathogen-associated antigen is coupled by the reaction of a carbodiimide and a primary amine group on the ARC/endo-gag polypeptide. In certain embodiments, is coupled by a heterobifunctional linker. In certain embodiments, the pathogen-associated antigen is coupled by the reaction of a maleimide/hydrazide and a sulfhydryl group on the ARC/endo-gag polypeptide. In certain embodiments, the pathogen-associated antigen is coupled by the reaction of a pyridyldithiol/hydrazide and a sulfhydryl group on the ARC/endo-gag polypeptide. In certain embodiments, the crosslinker is a photoreactive crosslinker. In certain embodiments, the pathogen-associated antigen is coupled by a peptide linkage as a fusion protein. In certain embodiments, the pathogen-associated antigen is coupled by a peptide linkage N-terminal to the ARC/endo-gag polypeptide. In certain embodiments, the pathogen-associated antigen is coupled by a peptide linkage C-terminal to the ARC/endo-gag polypeptide. In certain embodiments, the pathogen-associated antigen and the ARC/endo-gag polypeptide are connected via a flexible polypeptide linker. In certain embodiments, the pathogen-associated antigen and the ARC/endo-gag polypeptide are connected via a flexible polypeptide linker, wherein the pathogen-associated antigen polypeptide is N-terminal to the ARC/endo-gag polypeptide. In certain embodiments, the pathogen-associated antigen and the ARC/endo-gag polypeptide are connected via a flexible polypeptide linker, wherein the pathogen-associated antigen polypeptide is C-terminal to the ARC/endo-gag polypeptide.

The ARC/endo-gag-VLP compositions comprise unlabeled or uncoupled ARC/endo-gag polypeptides included with adjuvant coupled ARC/endo-gag polypeptides and pathogen-associated antigen coupled ARC/endo-gag polypeptides as specific percentages. Percentages described herein are based upon a percentage of the ARC/endo-gag protein with the indicated coupling.

In certain embodiments, adjuvant coupled ARC/endo-gag is present at about 1% to about 10% in the ARC/endo-gag-VLP vaccine compositions. In certain embodiments, adjuvant coupled ARC/endo-gag is present at about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 9% to about 10%. In certain embodiments, adjuvant coupled ARC/endo-gag is present at about 1%, about 2%, about 3%, about 4%, about 5%, about 6%, about 7%, about 8%, about 9%, or about 10%. In certain embodiments, adjuvant coupled ARC/endo-gag is present at, at least about 1%, about 2%, about 3%, about 4%, about 5%, about 6%, about 7%, about 8%, or about 9%. In certain embodiments, adjuvant coupled ARC/endo-gag is present at, at most about 2%, about 3%, about 4%, about 5%, about 6%, about 7%, about 8%, about 9%, or about 10%.

In certain embodiments, adjuvant coupled ARC/endo-gag is present at about 5% to about 40% in the ARC/endo-gag-VLP vaccine compositions. In certain embodiments, adjuvant coupled ARC/endo-gag is present at about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40%. In certain embodiments, adjuvant coupled ARC/endo-gag is present at about 5%, about 10%, about 15%, about 20%, about 25%, about 30%, about 35%, or about 40%. In certain embodiments, adjuvant coupled ARC/endo-gag is present at, at least about 5%, about 10%, about 15%, about 20%, about 25%, about 30%, or about 35%. In certain embodiments, adjuvant coupled ARC/endo-gag is present at, at most about 10%, about 15%, about 20%, about 25%, about 30%, about 35%, or about 40%.

In certain embodiments, adjuvant coupled ARC/endo-gag is present at less than 2% in the ARC/endo-gag-VLP vaccine compositions. In certain embodiments the adjuvant coupled ARC/endo-gag is present at about 0.01% to about 2%, about 0.01% to about 1.5%, about 0.1% to about 1.5%, about 0.2% to about 1%, about 0.2% to about 0.5%, about 0.01% to about 1.0%, about 0.01% to about 0.5%, about 0.01% to about 0.25%, about 0.01% to about 0.1%. In certain embodiments, 1, 2, 3, 4, 5, 6, 7, 8, 9, 10, about 15, about 20, about 25 or about 30 copies of an adjuvant coupled ARC/endo-gag polypeptide are present in an ARC/endo-gag-VLP vaccine particle. In certain embodiments, the ARC/endo-gag-VLP vaccine compositions contain no adjuvant coupled ARC/endo-gag.

In certain embodiments, pathogen-associated antigen coupled ARC/endo-gag is present at about 1% to about 10% in the ARC/endo-gag-VLP vaccine compositions. In certain embodiments, pathogen-associated antigen coupled ARC/endo-gag is present at about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 9% to about 10%. In certain embodiments, pathogen-associated antigen coupled ARC/endo-gag is present at about 1%, about 2%, about 3%, about 4%, about 5%, about 6%, about 7%, about 8%, about 9%, or about 10%. In certain embodiments, pathogen-associated antigen coupled ARC/endo-gag is present at, at least about 1%, about 2%, about 3%, about 4%, about 5%, about 6%, about 7%, about 8%, or about 9%. In certain embodiments, pathogen-associated antigen coupled ARC/endo-gag is present at, at most about 2%, about 3%, about 4%, about 5%, about 6%, about 7%, about 8%, about 9%, or about 10%.

In certain embodiments, pathogen-associated antigen coupled ARC/endo-gag is present at about 5% to about 40% in the ARC/endo-gag-VLP vaccine compositions. In certain embodiments, pathogen-associated antigen coupled ARC/endo-gag is present at about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40%. In certain embodiments, pathogen-associated antigen coupled ARC/endo-gag is present at about 5%, about 10%, about 15%, about 20%, about 25%, about 30%, about 35%, or about 40%. In certain embodiments, pathogen-associated antigen coupled ARC/endo-gag is present at, at least about 5%, about 10%, about 15%, about 20%, about 25%, about 30%, or about 35%. In certain embodiments, pathogen-associated antigen coupled ARC/endo-gag is present at, at most about 10%, about 15%, about 20%, about 25%, about 30%, about 35%, or about 40%.

In certain embodiments, pathogen-associated antigen coupled ARC/endo-gag is present at about 30% to 100% in the ARC/endo-gag-VLP vaccine compositions. In certain embodiments, pathogen-associated antigen coupled ARC/endo-gag is present at about 30% to about 40%, about 40% to about 50%, about 50% to about 60%, about 60% to about 70%, about 70% to about 80%, about 80% to about 90%, about 90% to about 95%, about 95% to 100%. In certain embodiments, pathogen-associated antigen coupled ARC/endo-gag is present at about 45%, about 50%, about 55%, about 60%, about 65%, about 70%, about 75%, about 80%, about 85%, about 90%, about 95%, or about 100%. In certain embodiments, pathogen-associated antigen coupled ARC/endo-gag is present at, at least about 50%, about 60%, about 70%, about 80%, about 90%, about 95%, or about 98%. In certain embodiments, pathogen-associated antigen coupled ARC/endo-gag is present at, at most about 50%, about 60%, about 70%, about 80%, about 90%, about 95%, or about 98%.

In certain embodiments, pathogen-associated antigen coupled ARC/endo-gag is present at less than 2% in the ARC/endo-gag-VLP vaccine compositions. In certain embodiments the pathogen-associated antigen coupled ARC/endo-gag is present at about 0.01% to about 2%, about 0.01% to about 1.5%, about 0.1% to about 1.5%, about 0.2% to about 1%, about 0.2% to about 0.5%, about 0.01% to about 1.0%, about 0.01% to about 0.5%, about 0.01% to about 0.25%, about 0.01% to about 0.1%. In certain embodiments, 1, 2, 3, 4, 5, 6, 7, 8, 9, 10, about 15, about 20, about 25 or about 30 copies of a pathogen-associated antigen coupled ARC/endo-gag polypeptide are present in an ARC/endo-gag-VLP vaccine particle. In certain embodiments, the ARC/endo-gag-VLP vaccine compositions contain no pathogen-associated antigen coupled ARC/endo-gag.

In certain embodiments, uncoupled ARC/endo-gag is present at about 90% to about 99% in the ARC/endo-gag-VLP vaccine compositions. In certain embodiments, uncoupled ARC/endo-gag is present at about 90% to about 91%, about 90% to about 92%, about 90% to about 93%, about 90% to about 94%, about 90% to about 95%, about 90% to about 96%, about 90% to about 97%, about 90% to about 98%, about 90% to about 99%, about 91% to about 92%, about 91% to about 93%, about 91% to about 94%, about 91% to about 95%, about 91% to about 96%, about 91% to about 97%, about 91% to about 98%, about 91% to about 99%, about 92% to about 93%, about 92% to about 94%, about 92% to about 95%, about 92% to about 96%, about 92% to about 97%, about 92% to about 98%, about 92% to about 99%, about 93% to about 94%, about 93% to about 95%, about 93% to about 96%, about 93% to about 97%, about 93% to about 98%, about 93% to about 99%, about 94% to about 95%, about 94% to about 96%, about 94% to about 97%, about 94% to about 98%, about 94% to about 99%, about 95% to about 96%, about 95% to about 97%, about 95% to about 98%, about 95% to about 99%, about 96% to about 97%, about 96% to about 98%, about 96% to about 99%, about 97% to about 98%, about 97% to about 99%, or about 98% to about 99%. In certain embodiments, uncoupled ARC/endo-gag is present at about 90%, about 91%, about 92%, about 93%, about 94%, about 95%, about 96%, about 97%, about 98%, or about 99%. In certain embodiments, uncoupled ARC/endo-gag is present at, at least about 90%, about 91%, about 92%, about 93%, about 94%, about 95%, about 96%, about 97%, or about 98%. In certain embodiments, uncoupled ARC/endo-gag is present at, at most about 91%, about 92%, about 93%, about 94%, about 95%, about 96%, about 97%, about 98%, or about 99%.

In certain embodiments, uncoupled ARC/endo-gag is present at about 60% to about 90% in the ARC/endo-gag-VLP vaccine compositions. In certain embodiments, uncoupled ARC/endo-gag is present at about 60% to about 65%, about 60% to about 70%, about 60% to about 75%, about 60% to about 80%, about 60% to about 85%, about 60% to about 90%, about 65% to about 70%, about 65% to about 75%, about 65% to about 80%, about 65% to about 85%, about 65% to about 90%, about 70% to about 75%, about 70% to about 80%, about 70% to about 85%, about 70% to about 90%, about 75% to about 80%, about 75% to about 85%, about 75% to about 90%, about 80% to about 85%, about 80% to about 90%, or about 85% to about 90%. In certain embodiments, uncoupled ARC/endo-gag is present at about 60%, about 65%, about 70%, about 75%, about 80%, about 85%, or about 90%. In certain embodiments, uncoupled ARC/endo-gag is present at, at least about 60%, about 65%, about 70%, about 75%, about 80%, or about 85%. In certain embodiments, uncoupled ARC/endo-gag is present at, at most about 65%, about 70%, about 75%, about 80%, about 85%, or about 90%.

In certain embodiments, an ARC/endo-gag-VLP vaccine comprises about 80% uncoupled ARC/endo-gag, about 10% ARC/endo-gag coupled to adjuvant, and about 10% ARC/endo-gag coupled to a pathogen-associated antigen. In certain embodiments, an ARC/endo-gag-VLP vaccine comprises about 80% uncoupled ARC/endo-gag, about 15% ARC/endo-gag coupled to adjuvant, and about 5% ARC/endo-gag coupled to a pathogen-associated antigen. In certain embodiments, an ARC/endo-gag-VLP vaccine comprises about 80% uncoupled ARC/endo-gag, about 5% ARC/endo-gag coupled to adjuvant, and about 15% ARC/endo-gag coupled to a pathogen-associated antigen. In certain embodiments, an ARC/endo-gag-VLP vaccine comprises about 80% uncoupled ARC/endo-gag, about 1% ARC/endo-gag coupled to adjuvant, and about 19% ARC/endo-gag coupled to a pathogen-associated antigen. In certain embodiments, an ARC/endo-gag-VLP vaccine comprises about 80% uncoupled ARC/endo-gag, about 2% ARC/endo-gag coupled to adjuvant, and about 18% ARC/endo-gag coupled to a pathogen-associated antigen. In certain embodiments, an ARC/endo-gag-VLP vaccine comprises about 80% uncoupled ARC/endo-gag, about 3% ARC/endo-gag coupled to adjuvant, and about 17% ARC/endo-gag coupled to a pathogen-associated antigen. In certain embodiments, an ARC/endo-gag-VLP vaccine comprises about 80% uncoupled ARC/endo-gag, about 4% ARC/endo-gag coupled to adjuvant, and about 16% ARC/endo-gag coupled to a pathogen-associated antigen. In certain embodiments, an ARC/endo-gag-VLP vaccine comprises about 90% uncoupled ARC/endo-gag, about 5% ARC/endo-gag coupled to adjuvant, and about 5% ARC/endo-gag coupled to a pathogen-associated antigen. In certain embodiments, an ARC/endo-gag-VLP vaccine comprises about 90% uncoupled ARC/endo-gag, about 1% ARC/endo-gag coupled to adjuvant, and about 9% ARC/endo-gag coupled to a pathogen-associated antigen. In certain embodiments, an ARC/endo-gag-VLP vaccine comprises about 90% uncoupled ARC/endo-gag, about 2% ARC/endo-gag coupled to adjuvant, and about 8% ARC/endo-gag coupled to a pathogen-associated antigen. In certain embodiments, an ARC/endo-gag-VLP vaccine comprises about 90% uncoupled ARC/endo-gag, about 3% ARC/endo-gag coupled to adjuvant, and about 7% ARC/endo-gag coupled to a pathogen-associated antigen. In certain embodiments, an ARC/endo-gag-VLP vaccine comprises about 90% uncoupled ARC/endo-gag, about 4% ARC/endo-gag coupled to adjuvant, and about 6% ARC/endo-gag coupled to a pathogen-associated antigen.

The ARC polypeptides of the VLPs described herein in certain embodiments, comprise a human ARC polypeptide. In certain embodiments, the ARC polypeptide comprises an amino acid sequence at least about 90%, 95%, 97%, 98%, 99% identical to SEQ ID NO: 1. In certain embodiments, the ARC polypeptide comprises an amino acid sequence identical to SEQ ID NO: 1. In certain embodiments, the ARC polypeptide comprises a deletion of 1, 2, 3, 4, 5, 6, 7, 8, 9, 10 amino acids from the N- or C-terminus of the ARC polypeptide.

In certain embodiments, the polypeptide of the VLP is an endo-gag. The endo-gag polypeptide may be any endo-gag polypeptide encoded by the genome of a cell, whether expressed or non-expressed.

In certain embodiments, the polypeptide of the VLP is an endo-gag. In certain embodiments, the endo-gag polypeptide comprises an amino acid sequence at least about 90%, 95%, 97%, 98%, 99% identical to SEQ ID NO: 16. In certain embodiments, the endo-gag polypeptide comprises an amino acid sequence identical to SEQ ID NO: 16. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 17. In certain embodiments, the endo-gag polypeptide comprises an amino acid sequence identical to SEQ ID NO: 17. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 18. In certain embodiments, the endo-gag polypeptide comprises an amino acid sequence identical to SEQ ID NO: 18. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 19. In certain embodiments, the endo-gag polypeptide comprises an amino acid sequence identical to SEQ ID NO: 19. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 20. In certain embodiments, the endo-gag polypeptide comprises an amino acid sequence identical to SEQ ID NO: 20. In certain embodiments, the endo-gag comprises a deletion of 1, 2, 3, 4, 5, 6, 7, 8, 9, 10 amino acids from the N- or C-terminus of the endo-gag In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 21. In certain embodiments, the endo-gag polypeptide comprises an amino acid sequence identical to SEQ ID NO: 21. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 22. In certain embodiments, the endo-gag polypeptide comprises an amino acid sequence identical to SEQ ID NO: 22. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 23. In certain embodiments, the endo-gag polypeptide comprises an amino acid sequence identical to SEQ ID NO: 23. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 24. In certain embodiments, the endo-gag polypeptide comprises an amino acid sequence identical to SEQ ID NO: 24. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 25. In certain embodiments, the endo-gag polypeptide comprises an amino acid sequence identical to SEQ ID NO: 25. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 26. In certain embodiments, the endo-gag polypeptide comprises an amino acid sequence identical to SEQ ID NO: 26. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 27. In certain embodiments, the endo-gag polypeptide comprises an amino acid sequence identical to SEQ ID NO: 27. In certain embodiments, the endo-gag comprises a deletion of 1, 2, 3, 4, 5, 6, 7, 8, 9, 10 amino acids from the N- or C-terminus of the endo-gag.

In certain embodiments, the polypeptide of the VLP is an Endogenous Gag (Endo-gag). In certain embodiments, the endo-gag polypeptide comprises an amino acid sequence at least about 90%, 95%, 97%, 98%, 99% identical to SEQ ID NO: 28. In certain embodiments, the endo-gag polypeptide comprises an amino acid sequence identical to SEQ ID NO: 28. In certain embodiments, the endo-gag comprises a deletion of 1, 2, 3, 4, 5, 6, 7, 8, 9, 10 amino acids from the N- or C-terminus of the endo-gag.

The VLPs may comprise a single type of ARC or endo-gag polypeptide or a mixture of any 1, 2, 3, 4, 5, or more ARC/endo-gag polypeptides selected from any of SEQ ID NOs:1, 16, 17, 18, 19, 20, 21, 22, 23, 24, 25, 26, 27, or 28.

Adjuvants

The ARC/endo-gag compositions described herein further comprise an adjuvant. Adjuvants allow for activation of the immune system and can act specifically through specific innate immune signaling molecules (Toll-like receptors, RIG receptors, NOD receptors, etc.) or non-specifically (e.g., water-in-oil emulsions, aluminum compounds). The adjuvants used in the compositions are, in certain embodiments, not conjugated to an ARC/endo-gag polypeptide, but mixed with the ARC/end-gag VLPs in an injectable form. In other embodiments, the adjuvants are coupled to a certain amount or percentage of VLP ARC/endo-gag polypeptides. Such coupling can be covalent or non-covalent. When the coupling is covalent, the coupling can be through a peptide bond (e.g., a fusion protein) or a non-peptide bond conjugation.

The adjuvant polypeptides described herein, are in certain embodiments, coupled to ARC/endo-gag peptides as a fusion protein. In certain embodiments, the adjuvant polypeptide is fused to the N-terminus of an ARC/end-gag polypeptide; the fusion optionally comprises a flexible polypeptide linker between the adjuvant polypeptide and the ARC/endo-gag polypeptide. In certain embodiments, the adjuvant polypeptide is fused to the C-terminus of an ARC/end-gag polypeptide; the fusion optionally comprises a flexible polypeptide linker between the adjuvant polypeptide and the ARC/endo-gag polypeptide.

Adjuvant polypeptides or adjuvant non-polypeptides (e.g., nucleic acids, bacterial compounds) are, in certain embodiments, covalently coupled or cross-linked by non-peptide linkages. In certain embodiments, the adjuvant polypeptide is coupled to an ARC/endo-gag polypeptide by a primary amine (e.g., lysine or N-terminus of the polypeptide chain), a sulfhydryl (e.g., cysteine), a carboxyl (e.g., aspartic acid, glutamic acid or C-terminus of the polypeptide chain). The cross-linking reaction can be any suitable reaction, including but not limited to, an amine-to-amine, sulfhydryl-to-sulfhydryl, amine-to-sulfhydryl, carboxyl-to-amine, or sulfhydryl-to-carboxyl. In certain embodiments, the adjuvant is coupled by the reaction of an NHS ester and a primary amine on the ARC/endo-gag polypeptide (e.g., a lysine residue). In certain embodiments, the adjuvant is coupled by the reaction of an imidoester and a primary amine on the ARC/endo-gag polypeptide. In certain embodiments, the adjuvant is coupled by the reaction of a maleimide group and a sulfhydryl group (e.g., cysteine residue) on the ARC/endo-gag polypeptide. In certain embodiments, the adjuvant is coupled by the reaction of a maleimide group and a primary amine group on the ARC/endo-gag polypeptide. In certain embodiments, the adjuvant is coupled by the reaction of a haloacetyl group and a sulfhydryl group on the ARC/endo-gag polypeptide. In certain embodiments, the adjuvant is coupled by the reaction of a haloacetyl group and a primary amine group on the ARC/endo-gag polypeptide. In certain embodiments, the adjuvant is coupled by the reaction of a pyridyldithiol and a sulfhydryl group on the ARC/endo-gag polypeptide. In certain embodiments, the adjuvant is coupled by the reaction of a pyridyldithiol and a primary amine group on the ARC/endo-gag polypeptide. In certain embodiments, the adjuvant is coupled by the reaction of a carbodiimide and a primary amine group on the ARC/endo-gag polypeptide. In certain embodiments, the adjuvant is coupled by a heterobifunctional linker. In certain embodiments, the adjuvant is coupled by the reaction of a maleimide/hydrazide and a sulfhydryl group on the ARC/endo-gag polypeptide. In certain embodiments, the adjuvant is coupled by the reaction of a pyridyldithiol/hydrazide and a sulfhydryl group on the ARC/endo-gag polypeptide. In certain embodiments, the crosslinker is a photoreactive crosslinker. For such conjugations, VLPs may be formed beforehand, and appropriate coupling reactions are carried out after VLP formation. Alternatively, the ARC/endo-gag polypeptides may be coupled with adjuvant before formation of VLPs.

An adjuvant according to the methods of this disclosure can be a pathogen-associated molecular pattern (PAMP) or a synthetic version thereof. PAMPs are small molecules conserved within a class of microbes and include, without limitation, glycans, glycol-conjugations, bacterial flagellin, lipoteichoic acid, peptidoglycan, CpG oligonucleotides, and double-stranded RNA. PAMPs activate a variety of innate immune receptors, known as pattern recognition receptors, expressed in antigen-presenting cells and initiate adaptive immune response attributable to B and T cells. Dendritic cells and other antigen-presenting cells express a variety of pattern recognition receptors and are activated in response to their binding to PAMPs. Pattern recognition receptors include, without limitation, Toll-like receptors, NOD-like receptors, RIG-1 receptors, MDA-5 receptors, and the STING pathway. In one embodiment, the dendritic cell-activating molecule activates dendritic cell sthrough a Toll-like receptor, a NOD-like receptor, a RIG-1 or MDA-5 receptor, a C-type lectin receptor, or the STING pathway.

Toll-like receptors are a class of receptors that are involved in the innate immune system. In a certain embodiment, the adjuvant activates a toll-like receptor. In another embodiment, the dendritic cell-activating molecule is a toll-like receptor agonist from the list consisting of a CpG oligonucleotide, SD-101, LFX453, imiquimod, Bacillus Calmette-Guérin (BCG), Poly ICLC, GSK1795091, and combinations thereof.

NOD-like receptors are a class of pattern recognition receptors found intracellularly in antigen-presenting cells that bind PAMPs and play a role in the innate immune system. In certain embodiments, the adjuvant activates a NOD-like receptor. In another embodiment, the dendritic cell activating-molecule is a NOD-like receptor agonist selected from the list consisting of bacterial peptidoglycan, an acylated derivative of iE-DAP (C12-iE-DAP), D-gamma-Glu-mDAP (iE-DAP), L-Ala-gamma-D-Glu-mDAP (Tri-DAP), muramyl dipeptide (MDP), muramyl tripeptide, L18-MDP, M-TriDAP, murabutide, PGN-ECndi, PGN-ECndss, PGN-SAndi, N-glycolylated muramyl dipeptide, murabutide, and combinations thereof.

RIG-1 and MDA-5 receptors also recognize PAMPs. Specifically, both RIG-1 receptors and MDA-5 receptors are involved in the recognition of viruses by the innate immune system. RIG-1 receptors generally bind to single- or double-stranded RNA strands of less than 2000 base pairs, while MDA-5 receptors generally bind to virally-derived single or double RNA strands greater than 2000 base pairs. When activated, these receptors promote interferon signaling and other responses of the innate immune system. In certain embodiments, the adjuvant activates a RIG-1 or MDA5 receptor. In another embodiment, the dendritic cell-activating molecule is a RIG-1 or MDA-5 receptor agonist selected from the list consisting of poly(I:C), Poly(dA:dT), Poly(dG:dC), 3p-hpRNA, 5'ppp-dsRNA, and combinations thereof.

C-type lectin receptors are involved in recognition of PAMPs, particularly those derived from fungi and mycobacteria. When a PAMP binds to a C-type lectin receptor, the innate immune system is activated. In certain embodiments, the adjuvant activates a C-type lectin receptor. In another embodiment, the adjuvant is a C-type lectin receptor agonist selected from the list consisting of Beta-1,3-glucan, zymosan, heat-killed *C. albicans*, cord factor, Trehalose-6,6-dibehenate, and combinations thereof.

The STING pathway is involved in innate immunity and the detection of PAMPs. Activation of the STING pathway results in expression of type I interferon. In certain embodiments, the adjuvant activates the STING pathway. In certain embodiments, the adjuvant is a STING agonist selected from the list consisting of 2',3'-cGAMP (CAS Number, 1441190-66-4), 4-[(2-Chloro-6-fluorophenyl)methyl]-N-(furan-2-ylmethyl)-3-oxo-1,4-benzothiazine-6-carboxamide, MK-1454, ADU-S100/MIW815, SRCB-0074, SYNB1891, E-7766, or SB11285, and combinations thereof.

CD40 is a TNF-family receptor expressed on dendritic cells and other antigen-presenting cells. CD40 signaling results in the expression of costimulatory ligands, cytokines, enhanced antigen presentation, and trafficking to the draining lymph node. In certain embodiments, the adjuvant comprises a CD40 agonist. In certain embodiments, the CD40 agonist is a CD40 agonistic antibody. Examples of CD40 agonist antibodies include, but are not limited to, dacetuzumab (also known as SGN-40, Seattle Genetics), CP-870,893 (University of Pennsylvania/Hoffmann-LaRoche), ADC-1013 (Alligator Bioscience AB), 2141-v11 (Rockefeller University), APX005M (Apexigen, Inc), Chi Lob 7/4 (Cancer research UKK), BG9588 (NIAMS), CFZ533 (Novartis), PG10 (PanGenetics UK Limited), BMS-986004 (Bristol-Myer Squibbs), lucatumumab (also known as HCD122, Novartis), HCD122 (Novartis), JNJ-64457107 (Janssen Research & Development), selicrelumab (also known as R07009789, Hoffman-La Roche), ASKP1240 (Astellas Pharma Global Development), and SEA-CD40 (Seattle Genetics).

Immunity can be primed by cytokines and chemokines. Cytokines can control the maturation of immature dendritic cells and activate dendritic cells. In certain embodiments, the adjuvant promotes signaling or is an agonist of a cytokine receptor. In other embodiments, the adjuvant comprises a cytokine selected from the list consisting of granulocyte-macrophage colony-stimulating factor (GM-CSF), interleukin-15 (IL-15), tumor necrosis factor alpha (TNF-alpha), interferon gamma (IFN-gamma), and combinations thereof.

In certain embodiments, the adjuvant comprises a water-in-oil emulsion, such as the Montanide series of adjuvants, including but not limited to, ISA-25™, ISA-50™, ISA-51™, ISA-206™, ISA720™, or SEPPIC™. Other water-in-oil emulsion adjuvants comprise complete Freund's adjuvant, incomplete Freund's adjuvant, MF59, squalene-water emulsions, OW-14, and combinations thereof.

Certain nucleic acids can act as adjuvants. In certain embodiments, the adjuvant comprises a nucleic acid. In certain embodiments, the nucleic acid is a DNA. In certain embodiments, the DNA comprises CPG-1018, CPG-1826, CPG-2007, CPG-2006, or any combination thereof. In certain embodiments, the nucleic acid is an RNA. In certain embodiments, the RNA comprises CV1802, Poly(U), Poly (I:C), ssRNA40, GFP RNA, RNA41, RNA42, RNA33, RNA35, 5'-phosphorylated blunt-ended viral genomic dsRNA <300 bp, long dsRNA >1000 bp, Genomic ssRNA, ssRNA40, or any combination thereof.

Aluminum compounds have been included in vaccine formulations as adjuvants. In certain embodiments, the adjuvant comprises an aluminum compound. In certain embodiments, the aluminum compound comprises alum.

Many polypeptides from a wide range of pathogens have been noted for their adjuvant effects. Therefore, in certain embodiments, the adjuvant comprises a polypeptide from a pathogen. In certain embodiments, the polypeptide is a polypeptide from *Brucella abortus, Bordetella pertussis, Chlamydia trachomatis, Fusobacterium nucleatum, Mycobacterium tuberculosis, Neisseria meningitidis, Staphylococcus aureus, Shigella dysenteriae, Shigella flexneri, Streptococcus pneumoniae, Vibrio cholerae, Brucella abortus, Mycobacterium paratuberculosis, Neisseria meningitidis, Streptococcus pneumoniae*, or any combination thereof.

In certain embodiments, the adjuvant polypeptide is from a protein selected from the list consisting of: BCSP31, FHA, MOMP, PorB, PVL, Porin, OmpA, 34 kDa MOMP, PepO, OmpU, Lumazine synthase, Omp16, Omp19, BCSP31, CobT, RpfE, Rv0652, HBHA, NhhA, DnaJ, Pneumolysin, AA146 Pneumolysin, or any combination thereof.

In certain embodiments, the adjuvant polypeptide is from a bacterial species and protein selected from the list consisting of: *Brucella abortus* (BCSP31), *Bordetella pertussis* (FHA), *Chlamydia trachomatis* (MOMP), *Neisseria meningitidis* (PorB), *Staphylococcus aureus* (PVL), *Shigella dysenteriae* (Porin), *Shigella flexneri* (OmpA, 34 kDa MOMP), *Streptococcus pneumoniae* (PepO), *Vibrio cholerae* (OmpU), *Brucella abortus* (Lumazine synthase, Omp16, Omp19, BCSP31), *Mycobacterium paratuberculosis* (CobT, RpfE, Rv0652, HBHA), *Neisseria meningitidis* (NhhA), *Streptococcus pneumoniae* (DnaJ, Pneumolysin, AA146 Pneumolysin), or any combination thereof.

In certain embodiments, the adjuvant polypeptide is from bacterial flagellin.

In certain embodiments, the adjuvant polypeptide is from human heat shock protein 70.

The VLPs described herein can comprise a single type of adjuvant or a mixture of different adjuvants. In certain embodiments, the ARC/endo-gag VLPs comprise a single type of adjuvant. In certain embodiments, the ARC/endo-gag VLPs comprise a plurality of different types of adjuvant. In certain embodiments, the ARC/endo-gag VLPs comprise two or more types of adjuvant. In certain embodiments, the ARC/endo-gag VLPs comprise three or more types of adjuvant. In certain embodiments, the ARC/endo-gag VLPs comprise four or more types of adjuvant. In certain embodiments, the ARC/endo-gag VLPs comprise five or more types of adjuvant. In certain embodiments, the ARC/endo-gag VLPs comprise two, three, four, five, six, or seven different types of adjuvant.

Pathogen-Associated Antigens

The ARC/endo-gag compositions described herein further comprise a pathogen-associated antigen (PAA). Immune responses directed against the pathogen-associated antigen allow for the generation of pathogen-specific adaptive immune responses that can serve to protect an individual from infection, symptoms, severe diseases, or mortality associated with the pathogen. In certain embodiments, the pathogen-associated antigens are coupled to a certain amount or percentage of the ARC/endo-gag polypeptides of a VLP. Such coupling can be covalent or non-covalent. When the coupling is covalent, the coupling can be through a peptide bond (e.g., fusion protein) or a non-peptide bond conjugation.

The pathogen-associated antigens described herein are, in certain embodiments, coupled to ARC/endo-gag peptides as a fusion protein. In certain embodiments, the pathogen-associated antigen is fused to the N-terminus of an ARC/end-gag polypeptide, and the fusion optionally comprises a flexible polypeptide linker between the adjuvant polypeptide and the ARC/endo-gag polypeptide. In certain embodiments, the pathogen-associated antigen is fused to the C-terminus of an ARC/end-gag polypeptide, and the fusion optionally comprises a flexible polypeptide linker between the pathogen-associated antigen and the ARC/endo-gag polypeptide.

Pathogen-associated antigens are, in certain embodiments, covalently coupled by non-peptide linkages. In certain embodiments, the pathogen-associated antigen is coupled to an ARC/endo-gag polypeptide by a primary amine (e.g., lysine or N-terminus of the polypeptide chain), a sulfhydryl (e.g., cysteine), a carboxyl (e.g., aspartic acid, glutamic acid or C-terminus of the polypeptide chain). For such conjugations, VLPs may be formed beforehand, and appropriate coupling reactions are carried out after VLP formation. Alternatively, the ARC/endo-gag polypeptides may be coupled with pathogen-associated antigen before the formation of VLPs.

The pathogen-associated antigens can comprise full proteins derived from a pathogen or fragments of polypeptides derived from a pathogen. Full-proteins or large polypeptide fragments of proteins (>40 amino acids in length) can be used in the ARC/endo-gag polypeptides. Without being bound by theory, large polypeptides and shorter polypeptides may be phagocytosed or otherwise internalized and processed to be presented to T cells by the MHC molecules on antigen-presenting cells such as macrophages, dendritic cells, or B cells, leading to initiation of an immune response. Such an immune response results in an adaptive immune response comprising an antibody response, a cellular immune response, or a combination thereof. In certain embodiments, the ARC/endo-gag VLPs generate an antibody response, as indicated by pathogen-associated antigen-specific antibodies. In certain embodiments, the antibodies comprise IgG isotype antibodies. IgG antibodies are indicative of the establishment of immunological memory and are generally higher affinity than IgM antibodies. In certain embodiments, the ARC/endo-gag VLPs generate a cellular immune response represented by the generation of pathogen-associated antigen-specific helper T cells or pathogen-associated antigen-specific cytotoxic T cells.

In certain embodiments, the pathogen-associated antigen is configured to bind an MHC class I protein. In certain embodiments, the MHC class I is a human MHC class I. In certain embodiments, the pathogen-associated antigen is a polypeptide at least 8 amino acids in length. In certain embodiments, the pathogen-associated antigen is a polypeptide that is between 8 and 11 amino acids in length. In certain embodiments, the pathogen-associated antigen is a polypeptide that is 8, 9, 10, or 11 amino acids in length.

In certain embodiments, the pathogen-associated antigen is configured to bind an MHC class II protein. In certain embodiments, the MHC class II is a human MHC class II. In certain embodiments, the pathogen-associated antigen is a polypeptide at least 10 amino acids in length. In certain embodiments, the pathogen-associated antigen is a polypeptide that is between 10 and 40 amino acids in length. In certain embodiments, the pathogen-associated antigen is a polypeptide that is 10, 11, 12, 13, 14, 15, 16, 17, 18, 19, 20, 21, 22, 23, 24 or 25 amino acids in length.

In certain embodiments, the pathogen-associated antigen is large polypeptide greater than about 40 amino acids in length, which may contain a plurality of antigens capable of binding MHC class I or MHC class II. Such polypeptides can be from pathogen-derived antigens or polypeptides known to be immunogenic.

In certain embodiments, the pathogen-associated antigen comprises or consists of about 40 amino acids to about 1,000 amino acids. In certain embodiments, the pathogen-associated antigen comprises or consists of about 40 amino acids to about 50 amino acids, about 40 amino acids to about 100 amino acids, about 40 amino acids to about 200 amino acids, about 40 amino acids to about 300 amino acids, about 40 amino acids to about 400 amino acids, about 40 amino acids to about 500 amino acids, about 40 amino acids to about 750 amino acids, about 40 amino acids to about 1,000 amino acids, about 50 amino acids to about 100 amino acids, about 50 amino acids to about 200 amino acids, about 50 amino acids to about 300 amino acids, about 50 amino acids to about 400 amino acids, about 50 amino acids to about 500 amino acids, about 50 amino acids to about 750 amino acids, about 50 amino acids to about 1,000 amino acids, about 100 amino acids to about 200 amino acids, about 100 amino acids to about 300 amino acids, about 100 amino acids to about 400 amino acids, about 100 amino acids to about 500 amino acids, about 100 amino acids to about 750 amino acids, about 100 amino acids to about 1,000 amino acids, about 200 amino acids to about 300 amino acids, about 200 amino acids to about 400 amino acids, about 200 amino acids to about 500 amino acids, about 200 amino acids to about 750 amino acids, about 200 amino acids to about 1,000 amino acids, about 300 amino acids to about 400 amino acids, about 300 amino acids to about 500 amino acids, about 300 amino acids to about 750 amino acids, about 300 amino acids to about 1,000 amino acids, about 400 amino acids to about 500 amino acids, about 400 amino acids to about 750 amino acids, about 400 amino acids to about 1,000 amino acids, about 500 amino acids to about 750 amino acids, about 500 amino acids to about 1,000 amino acids, or about 750 amino acids to about 1,000 amino acids. In certain embodiments, the pathogen-associated antigen comprises or consists of about 40 amino acids, about 50 amino acids, about 100 amino acids, about 200 amino acids, about 300 amino acids, about 400 amino acids, about 500 amino acids, about 750 amino acids, or about 1,000 amino acids. In certain embodiments, the pathogen-associated antigen comprises or consists of at least about 40 amino acids, about 50 amino acids, about 100 amino acids, about 200 amino acids, about 300 amino acids, about 400 amino acids, about 500 amino acids, or about 750 amino acids. In certain embodiments, the pathogen-associated antigen comprises or consists of at most about 50 amino acids, about 100 amino acids, about 200 amino acids, about 300 amino acids, about 400 amino acids, about 500 amino acids, about 750 amino acids, or about 1,000 amino acids.

In certain embodiments, the pathogen-associated antigen is from a virus, a bacterium, a fungus, or a parasite.

In certain embodiments, the pathogen-associated antigen is from a bacterium, including without limitation a *Streptococcus*, a *Pseudomonas*, a *Shigella*, a *Campylobacter*, a *Salmonella*, a *Clostridium*, an *Escherichia*, or Bacillus *Anthracis*.

In certain embodiments, the pathogen-associated antigen is from a pathogen that causes human disease which include but are not limited to, Bacillus *anthracis* (anthrax), *Clostridium botulinum* toxin (botulism), *Yersinia pestis* (plague). Variola major (smallpox) and other related pox viruses, *Francisella tularensis* (tularemia), Viral hemorrhagic fevers, Arenaviruses, (e.g., Junin, Machupo, Guanarito, Chapare, Lassa, and/or Lujo), Bunyaviruses (e.g., Hantaviruses causing Hanta Pulmonary syndrome, Rift Valley Fever, and/or Crimean Congo Hemorrhagic Fever), Flaviviruses, Dengue, Filoviruses (e.g., Ebola and Marburg viruses), *Burkholderia pseudomallei* (melioidosis), *Coxiella burnetii* (Q fever), *Brucella* species (brucellosis), *Burkholderia mallei* (glanders), *Chlamydia psittaci* (Psittacosis), Ricin toxin (*Ricinus communis*), Epsilon toxin (*Clostridium perfringens*), *Staphylococcus* enterotoxin B (SEB), Typhus fever (*Rickettsia* prow azekii), Food- and waterborne pathogens, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A, *Cryptosporidium parvum, Cyclospora cayatanensis, Giardia lamblia, Entamoeba histolytica, Toxoplasma gondii, Naegleria fowleri, Balamuthia mandrillaris*, Fungi, Microsporidia, Mosquito-borne viruses (e.g., West Nile virus (WNV), LaCrosse encephalitis (LACV), California encephalitis, Venezuelan equine encephalitis (VEE), Eastern equine encephalitis (EEE), Western equine encephalitis (WEE), Japanese encephalitis virus (JE), St. Louis encephalitis virus (SLEV), Yellow fever virus (YFV), Chikungunya virus, Zika virus, Nipah and Hendra viruses, Additional hantaviruses, Tickborne hemorrhagic fever viruses, Bunyaviruses, Severe Fever with Thrombocytopenia Syndrome virus (SFTSV), Heartland virus, Flaviviruses (e.g., Omsk Hemorrhagic Fever virus, Alkhurma virus, Kyasanur Forest virus), Tickborne encephalitis complex flaviviruses, Tickborne encephalitis viruses, Powassan/Deer Tick virus, Tuberculosis, including drug-resistant Tuberculosis, Influenza virus, Prions, *Streptococcus, Pseudomonas, Shigella, Campylobacter, Salmonella, Clostridium, Escherichia*, Hepatitis C, papillomavirus, Epstein-Barr virus, varicella, variola, Orthomyxovirus, Severe acute respiratory syndrome associated coronavirus (SARS-CoV), SARS-CoV-2 (COVID-19), MERS-CoV, other highly pathogenic human coronaviruses, or any combination thereof.

In certain embodiments, the virus is a respiratory virus that primarily results in respiratory symptoms including, without limitation, coronaviruses, influenza viruses, adenoviruses, rhinoviruses, coxsackieviruses, and metapneumoviruseses. In certain embodiments, the virus is an enteric virus that primarily results in digestive symptoms including, without limitation, enteroviruses, noroviruses, heptoviruses, reoviruses, rotaviruses, parvoviruses, toroviruses, and mastadenovirus. In certain embodiments, the virus is a hemorrhagic fever virus including, without limitation, Ebola virus, Marburg virus, dengue fever virus, yellow fever virus, Rift valley fever virus, hanta virus, and Lassa fever virus.

In certain embodiments, the pathogen-associated antigen is from an influenza virus. In certain embodiments, the pathogen-associated antigen is from an influenza A virus, such as the H5N1 strain. In certain embodiments, the pathogen-associated antigen is from an influenza B virus. In certain embodiments, the pathogen-associated antigen is an influenza matrix M1 protein or a fragment thereof. In certain embodiments, the pathogen-associated antigen is an influenza neuraminidase or a fragment thereof. In certain embodiments, the pathogen-associated antigen is an influenza hemagglutinin or a fragment thereof. For example, the pathogen-associated antigen may comprise an entire hemagglutinin, an HA1 domain, an HA2 domain or any antigenic portion thereof.

In certain embodiments, the pathogen-associated antigen is a Coronaviridae antigen. In certain embodiments, the Coronaviridae exhibits human tropism. In certain embodiments, the Coronaviridae is selected from the list consisting of SARS Coronavirus (SARS-CoV-1), COVID-19 (SARS-CoV-2), MERS-coronavirus (MERS-CoV), or any combination thereof. In certain embodiments, the Coronaviridae comprises SARS Coronavirus (SARS-CoV-1). In certain embodiments, the Coronaviridae comprises COVID-19 (SARS-CoV-2). In certain embodiments, the Coronaviridae comprises MERS-coronavirus (MERS-CoV). In certain embodiments, the Coronaviridae antigen comprises a spike protein, an envelope protein, a nucleocapsid protein, a membrane protein, a membrane glycoprotein, or a non-structural protein. In certain embodiments, the Coronaviridae antigen comprises a spike protein, an envelope small membrane protein, a membrane protein, a non-structural protein 6 (NSP6), a nucleoprotein, an ORF10 protein, Protein 3a, Protein7a, Protein 9b, structural protein 8, uncharacterized protein 4, or any combination thereof. In certain embodiments, the Coronaviridae antigen comprises an amino acid residue sequence as set forth in any one of SEQ ID NOs: 30 to 42, and combinations thereof. In certain embodiments, the Coronaviridae antigen consists of an amino acid residue sequence as set forth in any one of SEQ ID NOs: 30 to 42, and combinations thereof. In certain embodiments, the Coronaviridae antigen comprises a spike protein comprising SEQ ID NO: 43 or SEQ ID NO: 44, or a fragment thereof.

The VLPs described herein can comprise a single type of pathogen-associated antigen or a mixture of different pathogen-associated antigens. In certain embodiments, the ARC/endo-gag VLPs comprise a single pathogen-associated antigen. In certain embodiments, the ARC/endo-gag VLPs comprise a plurality of different pathogen-associated antigens. In certain embodiments, the ARC/endo-gag VLPs comprise two or more pathogen-associated antigens, wherein the two or more pathogen-associated antigens are from the same pathogen. In certain embodiments, the ARC/endo-gag VLPs comprise two or more pathogen-associated antigens, wherein the two or more pathogen-associated antigens are from a different pathogen. In certain embodiments, the ARC/endo-gag VLPs comprise three or more pathogen-associated antigens, wherein the three or more pathogen-associated antigens are from the same pathogen. In certain embodiments, the ARC/endo-gag VLPs comprise four or more pathogen-associated antigens, wherein the four or more pathogen-associated antigens are from the same pathogen. In certain embodiments, the ARC/endo-gag VLPs comprise five or more pathogen-associated antigens, wherein the five or more pathogen-associated antigens are from the same pathogen. In certain embodiments, the ARC/endo-gag VLPs comprise two, three, four, five, six, or seven different pathogen-associated antigens, wherein the pathogen-associated antigens are from the same pathogen.

Methods of Making

The VLP vaccine compositions comprising ARC polypeptides, endo-gag polypeptides, or a mixture thereof are assembled from ARC or endo-gag polypeptides that are encoded by nucleic acid vectors that have been transferred into a suitable host cell.

In certain embodiments, the Arc polypeptides, endo-Gag polypeptides, engineered Arc polypeptides, and engineered endo-Gag polypeptides described herein are encoded by plasmid vectors. In some embodiments, vectors include any suitable vectors derived from either a eukaryotic or prokaryotic source. In some cases, vectors are obtained from bacteria (e.g., *E. coli*), insects, yeast (e.g., *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA3 1-Luc, pZE21-MCS-1, pFLAG ATS, pFLAG CTS, pFLAG MAC, pFLAG Shift-12c, pTAC-MAT-1, pFLAG CTC, or pTAC-MAT-2. Exemplary insect vectors include pFastBacl, pFastBac DETAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2. In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pA0815 *Pichia* vector, pFLD1 Pichi *pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector. Exemplary algae vectors include pChlamy-4 vector or MCS vector. Examples of mammalian vectors include transient expression vectors or stable expression vectors. Mammalian transient expression vectors include p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some embodiments, a host cell includes any suitable cell, such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., a yeast cell), an animal cell, or a plant cell. In some cases, a prokaryotic cell is a bacterial cell. Examples of a bacterial cell include gram-positive bacteria or gram-negative bacteria. In some embodiments, the gram-negative bacterium is anaerobic, rod-shaped, or both. In some instances, gram-positive bacteria include Actinobacteria, Firmicutes or Tenericutes. In some cases, gram-negative bacteria include *Aquifivae, Deinococcus-Thermus, Fibrobacteres Chlorobi/Bacteroidetes* (FCB group), *Fusobacteria, Gemmatimonadetes, Nitrospirae, Planctomycetes Verrucomicrobia/Chlamydiae* (PVC group), *Proteobacteria, Spirochaetes* or *Synergistetes*. In some embodiments, the bacterium is *Acidobacteria, Chloroflexi, Chrysiogenetes, Cyanobacteria, Deferribacteres, Dictyoglomi, Thermodesulfobacteria,* or *Thermotogae*. In some embodiments, a bacterial cell is *Escherichia coli, Clostridium botulinum*, or *Coli* bacilli. Exemplary prokaryotic host cells include, but are not limited to, BL21, Machl™, DH10BTM, TOP10, DH5a, DH1OBac™, Omni-Max™, MegaX™, DH12STM, INV110, TOP10F', INVaF, TOP10/P3, ccdB Survival, PIR1, PIR2, Stb12™, Stb13™, or Stb14™. In some instances, animal cells include a cell from a vertebrate or from an invertebrate. In some cases, an animal cell includes a cell from a marine invertebrate, fish, insect, amphibian, reptile, mammal, or human. In some cases, a fungus cell includes a yeast cell, such as brewer's yeast, baker's yeast, or wine yeast. Fungi include ascomycetes such as yeast, mold, filamentous fungi, basidiomycetes, or zygomycetes. In some instances, yeast includes *Ascomycota* or *Basidiomycota*. In some cases, Ascomycota includes *Saccharomycotina* (true yeasts, e.g., *Saccharomyces cerevisiae* (baker's yeast)) or *Taphrinomycotina* (e.g., *Schizosaccharomycetes* (fission yeasts)). In some cases, *Basidiomycota* includes *Agaricomycotina* (e.g., *Tremellomycetes*) or *Pucciniomycotina* (e.g., *Microbotryomycetes*). Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium,* or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans,* Rhodosporidium toru-*Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii,* or *Saccharomyces boulardii*. Exemplary yeast host cells include, but are not limited to, *Pichia pastoris* yeast strains such as GS115, KM71H, SMD1168, SMD1168H, and X-33; and *Saccharomyces cerevisiae* yeast strain such as INVScl. In some instances, additional animal cells include cells obtained from a mollusk, arthropod, annelid or sponge. In some cases, an additional animal cell is a mammalian cell, e.g., from a human, primate, ape, equine, bovine, porcine, canine, feline or rodent. In some cases, a rodent includes mouse, rat, hamster, gerbil, hamster, chinchilla, fancy rat, or guinea pig. Exemplary mammalian host cells include, but are not limited to, HEK 293 cells, 293 A cell line, 293FT cell line, 293F cells, 293 H cells, CHO DG44 cells, CHO-S cells, CHO-K1 cells, Expi293FTM cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line. In some instances, a mammalian host cell is a primary cell. In some instances, a mammalian host cell is a stable cell line or a cell line that has incorporated a genetic material of interest into its own genome and has the capability to express the product of the genetic material after many generations of cell division. In some cases, a mammalian host cell is a transient cell line or a cell line that has not incorporated a genetic material of interest into its own genome and does not have the capability to express the product of the genetic material after many generations of cell division. Exemplary insect host cells include, but are not limited to, *Drosophila* S2 cells, Sf9 cells, Sf21 cells, High Five™ cells, and expresSF+® cells. In some instances, plant cells include a cell from algae. Exemplary plant cell lines include, but are not limited to, strains from *Chlamydomonas reinhardtii* 137c, or Synechococcus *elongatus* PPC 7942.

Production of the VLPs described herein comprises recovering the ARC/end-gag polypeptides from a cell culture supernatant of a cell expressing the ARC/end-gag polypeptides and incubating the recovered polypeptides at conditions to form the VLPs. VLPs can self-assemble at salt concentrations ranging from 100 mM-1000 mM, 200 mM-800 mM, 300 mM-600 mM, or about 500 mM. The salt may comprise NaCl, KCl, $CaSO_4$, $Na_2CO_3$, $NaHCO_3$, $MgSO_4$, sodium acetate, sodium bicarbonate, sodium borate, sodium citrate, sodium phosphate, sodium sulfate, sodium sulfide, sodium sulfite, sodium thiosulfate, ammonium acetate, ammonium chloride, ammonium sulfate, magnesium chloride, potassium acetate, potassium carbonate, or potassium phosphate. In certain embodiments, ARC/endo-gag polypeptides recovered from supernatant can be subjected to one or more of centrifugation, ultracentrifugation, dialysis, filtration, ultrafiltration, buffer exchange, column chromatography, anion exchange chromatography or nickel affinity chromatography.

Therapeutic Methods

The ARC/endo-gag polypeptides described herein can be included with one or more pharmaceutically acceptable excipients, carriers, or diluents in a vaccine composition. The vaccine compositions described herein can be used in a method of priming an adaptive immune response in an individual against the pathogen from which the pathogen-associated antigen is derived. The vaccine compositions described herein can be used in a method of boosting an adaptive immune response in an individual against the pathogen from which the pathogen-associated antigen is derived. In certain embodiments, the adaptive immune response primed or boosted reduces the probability that the individual will be infected with the pathogen from which the pathogen-associated antigen is derived. In certain embodiments, the adaptive immune response primed or boosted reduces the probability that the individual will spread the pathogen from which the pathogen-associated antigen is derived.

Also described herein is a method of vaccinating an individual against a pathogen comprising administering to the individual a composition comprising: 1) an ARC polypeptide or an endogenous gag (endo-gag) polypeptide; 2) a pathogen-associated antigen derived from the pathogen; and 3) an adjuvant.

Also described herein is a method of inducing an antibody response to a pathogen in an individual comprising administering to the individual a composition comprising: 1) an ARC polypeptide or an endogenous gag (endo-gag) polypeptide; 2) a pathogen-associated antigen derived from the pathogen; and 3) an adjuvant. In certain embodiments, the antibody response is an IgG response.

Also described herein is a method of inducing a cellular immune response to a pathogen in an individual comprising administering to the individual a composition comprising: 1) an ARC polypeptide or an endogenous gag (endo-gag) polypeptide; 2) a pathogen-associated antigen derived from the pathogen; and 3) an adjuvant. In certain embodiments, the cellular immune response is a CD4+ helper T-cell response. In certain embodiments, the cellular immune response is a CD8+ cytotoxic T-cell response.

Pharmaceutically Acceptable Excipients, Carriers, and Diluents

In certain embodiments, the polypeptides or virus-like particles of the current disclosure are included in a pharmaceutical composition comprising one or more pharmaceutically acceptable excipients, carriers, and diluents. Various pharmaceutically acceptable ingredients are described in Remington: The Science and Practice of Pharmacy, Joseph P Remington and Loyd V. Allen, 22nd edition, Pharmaceutical Press, 2013.

The compositions of the present invention are in a biologically compatible form suitable for administration in vivo for subjects. The pharmaceutical compositions further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the VLP is administered.

Also described herein are kits comprising one or more of the polypeptides or virus-like particles described herein in a suitable container and one or more additional components selected from: instructions for use; a diluent, an excipient, a carrier, and a device for administration.

In certain embodiments, described herein is a method of preparing a vaccine comprising admixing one or more pharmaceutically acceptable excipients, carriers, or diluents and one or more Arc or endo-Gag polypeptides of the current disclosure. In certain embodiments, described herein is a method of preparing a vaccine for storage or shipping comprising lyophilizing one or more Arc or endo-Gag polypeptide compositions of the current disclosure.

EXAMPLES

The following illustrative examples are representative of embodiments of compositions and methods described herein and are not meant to be limiting in any way.

Example 1—Assembly of endoVLPs

A robust recombinant system was established to purify monomeric Arc or endo-Gag proteins and form highly pure and concentrated endoVLPs resembling viral capsids (FIG. 2). This was accomplished by expressing a 6×HIS tagged (SEQ ID NO: 47) version of Arc that is suitable for Ni-NTA column purification (FIG. 2A) and affinity tag cleavage, producing highly purified and soluble monomeric Arc protein (FIG. 2B). Arc protein is then subjected to buffer and temperature conditions that induce the formation of endoVLPs, which can be further purified and stripped of carry-through RNAs on an anion exchange (MonoQ) column on and AKTA Pure 25M FPLC system (FIG. 2C). Arc endoVLP nanoparticle consistency, purity, and capsid titer (as high as $4.02 \times 10^{12}$) can be confirmed using TEM (FIG. 2D).

Example 2—a Protocol for endoVLP Formation

A certain protocol for expression of recombinant ARC polypeptide and assembly into endVLPs is detailed below.

Expression vectors constructs comprising Arc and endo-Gag open reading frames were transformed into the Rosetta 2 (DE3)pLysS *E. coli* strain (Millipore Sigma, Cat #71403). Arc was induced with 0.1 mM IPTG followed by a 16-hour incubation at 16° C. Cell pellets were lysed by sonication in 20 mM sodium phosphate pH 7.4, 0.1M NaCl, 40 mM imidazole, 1 mM DTT, and 10% glycerol. The lysate was treated with excess TETRBO DNase (Thermo Fisher Scientific, Cat # AM2238), RNase Cocktail (Thermo Fisher Scientific, Cat # AM2286), and Benzonase Nuclease (Millipore Sigma, Cat #71205) to eliminate nucleic acids. NaCl was added to lysate in order to adjust the NaCl concentration to 0.5 M followed by centrifugation and filtration to remove cellular debris. 6×HIS-tagged (SEQ ID NO: 47) recombinant protein was loaded onto a HisTrap HP column (GE Healthcare, Cat #17-5247-01), washed with buffer A (20 mM sodium phosphate pH 7.4, 0.5M NaCl, 40 mM imidazole, and 10% glycerol), and eluted with a linear gradient of buffer B (20 mM sodium phosphate pH 7.4, 0.5M NaCl, 500 mM imidazole, and 10% glycerol). Collection tubes were supplemented in advance with 10 mL of 0.5 M EDTA pH 8.0 per 1 ml eluate. The resulting Arc or protein is generally more than 95% pure, with a yield of up to 50 mg per 1 L of bacterial culture.

Residual nucleic acid was removed by anion exchange chromatography on a Mono Q 5/50 GL column (GE Healthcare, Cat #17516601). Before loading to the column, recombinant protein was buffer exchanged to buffer C (20 mM Tris-HCl pH 8.0, 100 mM NaCl, and 10% glycerol) using Pierce Protein Concentrator PES, 10K MWCO, 5-20 ml" (Thermo Scientific, Cat #88528) according to the manufacturer's protocol. After loading, the mono Q resin was washed with 2 ml of buffer C. Arc and endo-Gag proteins were eluted using a linear gradient of buffer D (20 mM Tris-HCl pH 8.0, 500 mM NaCl, and 10% glycerol). RNA efficiently separated from Arc and eluted at 600 mM NaCl.

The N-terminal 6×HIS tag (SEQ ID NO: 47) and spacer were removed from concentrating peak fractions of the mono Q purified Arc using a 10 kDa MWCO PES concentrator and then treating with 10% v/v of AcTEV™ Protease (Invitrogen™ #12575023). The cleavage efficiency is above 99%, as revealed by an SDS-PAGE assay. The protein is then diluted into HisTrap Buffer A and cleaned with HisTrap HP resin. The resulting purified Arc has an N-terminal Glycine residue and does not contain the initial methionine.

Cleaved Arc protein (1 mg/mL) was loaded into a 20 kDa MWCO dialysis cassette and dialyzed overnight in 1M sodium phosphate (pH 7.5) at room temperature. The following day, the solution was removed from the cassette, transferred to microcentrifuge tubes, and spun at max speed for 5 minutes in a tabletop centrifuge. The supernatant was transferred to a 100 kDa MWCO Regenerated Cellulose Amicon ETltrafiltration Centrifugal concentrator. The buffer was exchanged to PBS pH 7.5, and the volume was reduced 20-fold.

Example 3—Assembly of endoVLPs from ARC Fusion Proteins

Figure 3A:
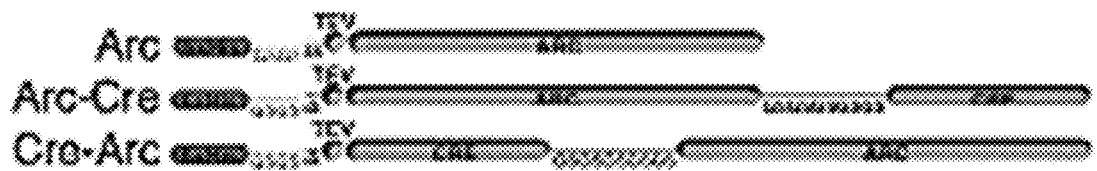
FIGS. 3A to 3E illustrate protein tethering and the generation of engineered Arc endoVLPS. 3A, recombinant construct design for the expression of Cre-tethered Arc proteins, separated by a 5×GS flexible linker peptide (SEQ ID NO: 46).
Figure 3B:
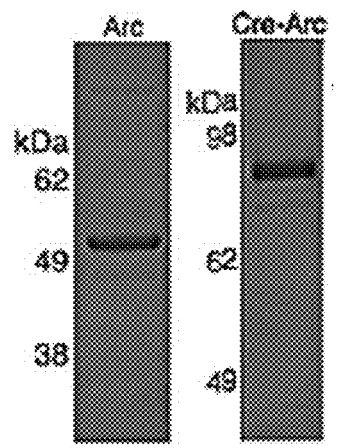
Figure 3C:
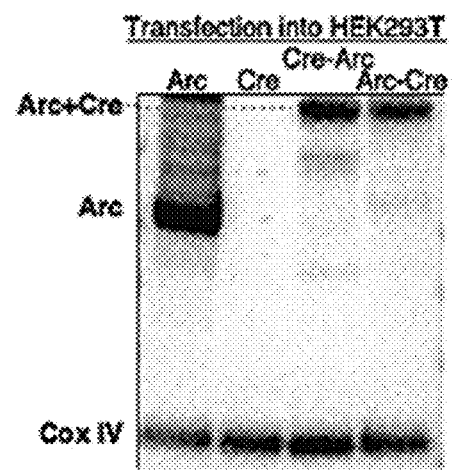
Figure 3D:
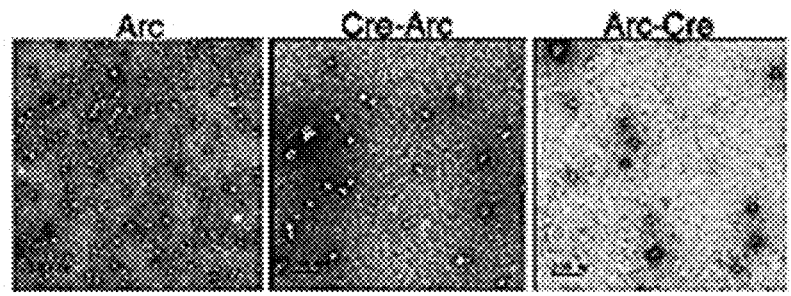
Figure 3E:
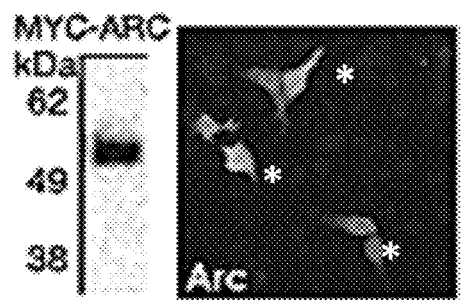

In order to utilize a recombinant Arc endoVLP delivery system for vaccine development, the Arc protein must be amenable to stable tethering of candidate antigens and adjuvant molecules while retaining the ability to assemble into VLP capsids. Various Arc protein fusions were generated, including fusion proteins with N- and C-terminal Cre domains separated from Arc by a SXGS flexible protein linker (SEQ ID NO: 46) (FIG. 3A). The Cre-Arc and Arc-Cre proteins were recombinantly expressed, purified, and treated with TEV protease to remove an N-terminal 6×HIS affinity tag (SEQ ID NO: 47). Integrity of the recombinant tethered proteins was verified by SDS-PAGE (FIG. 3B). Stable expression of the Arc-Cre fusions with N- or C-terminal Cre in transfected human HEK293T cells was confirmed by western blot analysis (FIG. 3C). endoVLP formation experiments performed using purified recombinant tethered and untethered Arcdemonstrated that both N- and C-terminal conjugations to Arc were capable of forming endoVLP structures (FIG. 3D). An enzyme-linked immunosorbent assay (ELISA) will be used to confirm that the N- and C-terminally tethered Cre proteins are displayed on the outside of the endoVLP structures. To verify the stability of an additional tagged Arc protein within human cells, an N-terminal MYC tagged Arc construct was recombinantly expressed in HEK293T cells. Stable expression was observed by western blot analysis and immunofluorescence microscopy (FIG. 3E). Dual labeling immunofluorescence confirmed the colocalization of Arc and Myc, demonstrating that the fusion protein was intact. These data confirm the amenability of the Arc protein to various engineering approaches, and its maintenance of endoVLP forming potential, even while tethering a protein as large as ~40 kDa, such as Cre. Arc can be recombinantly expressed as a GST-tagged fusion protein, increasing its versatility for conjugation to antigens or adjuvants that might be unstable in the context of a 6×HIS-tagged (SEQ ID NO: 47) fusion protein. These results demonstrate the ability to tether antigen and adjuvant molecules directly to recombinant Arc for vaccine screening and development. Indeed, carrying larger protein molecules will allow for more natural folding conditions and more potent antigen presentation.

Example 4—Labeling of ARC Proteins after VLP Formation

Figure 4A:
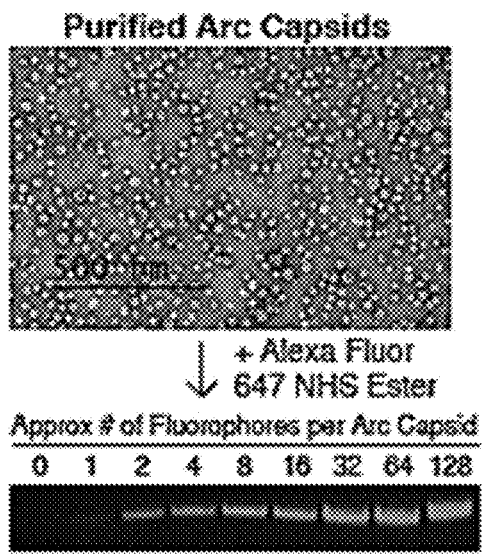
FIGS. 4A to 4D illustrate Arc endoVLP labeling and delivery into cultured cells and living animals. 4A, negative stain electron micrograph of recombinant human Arc endoVLPs that were subsequently labeled with titrated amounts of an Alexa Fluor 647 NETS-ester dye (Thermo). Fluorescent labeling was titrated, and labeled Arc protein (from formed endoVLPs) was visualized using SDS denaturing gel electrophoresis followed by direct fluorescence detection. 4B, the amount of fluorescent incorporation per Arc protein was then plotted against the molar excess of Dye in the labeling reaction. 4C and 4D, Purified and labeled Arc endoVLPs delivery was assessed after either introduction into cell culture media (C), or directly into mice via intravenous injection (D).
Figure 4B:
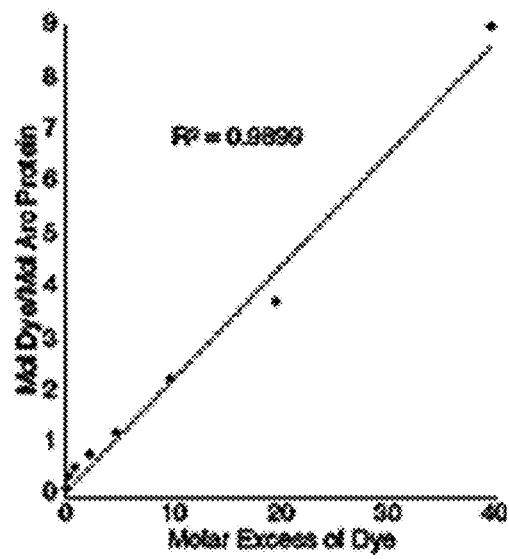
Figure 4C:
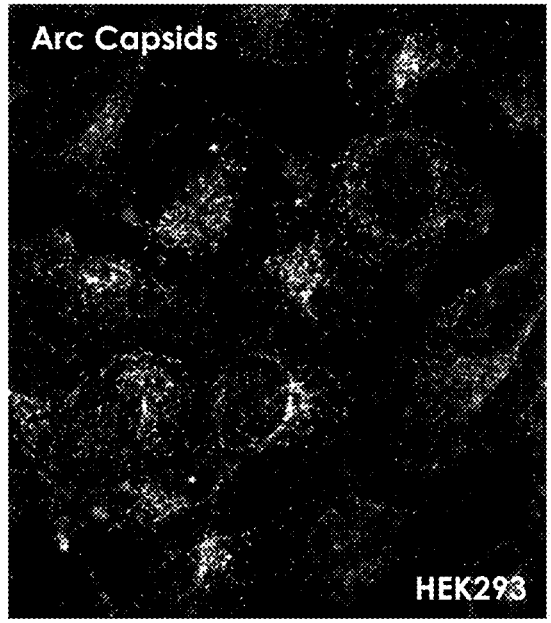
Figure 4D:
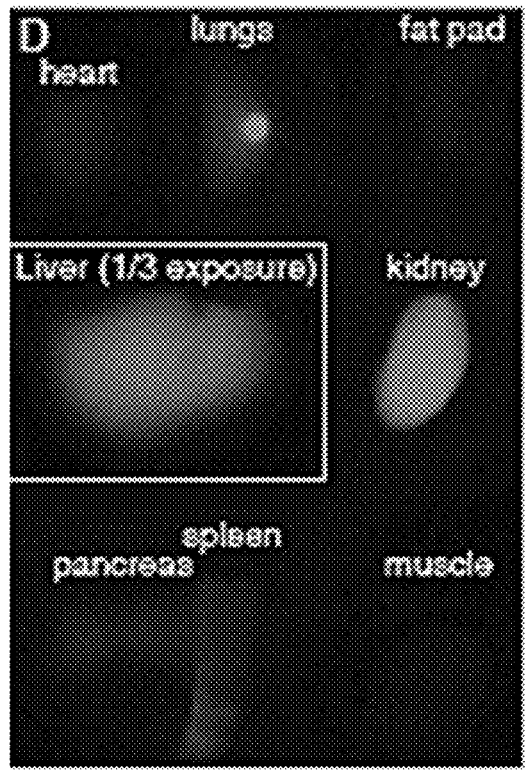

As an alternative to direct tethering, proteins will be conjugated directly to fully formed Arc endoVLPs. After confirming the assembly of highly pure recombinant Arc endoVLP preparations by TEM, endoVLP structures were fluorescently labeled through chemical crosslinking using Alexa Fluor (Thermo) NETS-ester (FIG. 4A). The number of fluorescent molecules linked to mature Arc endoVLPs scales linearly when increasing the amount of NETS ester dye added (FIG. 4B), indicating that the number of incorporated adjuvant or antigen molecules can be tightly regulated. Introduction of fluorescently labeled Arc endoVLPs into cultured cells (FIG. 4C) or throughout a living animal (FIG. 4D) displays the biostability of formed and labeled endoVLPs, as well as their biodistribution. This demonstrates Arc's amenability to engineering, as a large percentage of the exterior capsid face can be conjugated without a loss of capsid stability.

Example 5—In Vivo Testing of endoVLP-Based Vaccines

A mouse model system can provide in vivo proof-of-principle data for endoVLP vaccines comprising Arc or endo-Gag polypeptides. The mouse Arc protein (SEQ ID NO: 29) is used for these experiments. Groups of ten, split gender, eight-week-old BALB/C mice will be administered either naked endoVLPs (control) or an endoVLP SARS-CoV-2 vaccine (with spike protein as the antigen), with a second administration after two weeks. Three weeks after booster administration, serum and plasma will be collected, with an additional assessment of an antibody response against the viral antigen using a commercially available ELISA for SARS-CoV-2 spike protein. In vivo studies can also examine immune response in both B and T-cells. To determine the humoral immune responses by B-cells, a neutralization assay based on heat-inactivated animal sera would be employed. To assess cell-mediated immunity, the release of various cytokines in response to SARS-CoV-2 antigen-presenting target cells can be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

| | Sequence listings provided herein | |
|---|---|---|
| SEQ ID NO: | Sequence | Origin |
| 1 | GELDHRTSGGLHAYPGPRGGQVAKPNVILQIGKCRAEMLEHVRRTHR HLLAEVSKQVERELKGLHRSVGKLESNLDGYVPTSDSQRWKKSIKAC LCRCQETIANLERWVKREMHVWREVFYRLERWADRLESTGGKYPVG SESARHTVSVGVGGPESYCHEADGYDYTVSPYAITPPPAAGELPGQEP AEAQQYQPWVPGEDGQPSPGVDTQIFEDPREFLSHLEEYLRQVGGSEE YWLSQIQNHMNGPAKKWWEFKQGSVKNWVEFKKEFLQYSEGTLSR EAIQRELDLPQKQGEPLDQFLWRKRDLYQTLYVDADEEEIIQYVVGTL QPKLKRFLRHPLPKTLEQLIQRGMEVQDDLEQAAEPAGPHLPVEDEA ETLTPAPNSESVASDRTQPE | Human Arc |
| 16 | GPLTLLQDWCRGEHLNTRRCMLILGIPEDCGEDEFEETLQEACRHLGR YRVIGRMFRREENAQAILLELAQDIDYALLPREIPGKGGPWEVIVKPR NSDGEFLNRLNRFLEEERRTVSDMNRVLGSDTNCSAPRVTISPEFWTW AQTLGAAVQPLLEQMLYRELRVFSGNTISIPGALAFDAWLEHTTEML QMWQVPEGEKRRRLMECLRGPALQVVSGLRASNASITVEECLAALQ QVFGPVESHKIAQVKLCKAYQEAGEKVSSFVLRLEPLLQRAVENNVV SRRNVNQTRLKRVLSGATLPDKLRDKLKLMKQRRKPPGFLALVKLLR EEEEWEATLGPDRESLEGLEVAPRPPARITGVGAVPLPASGNSFDARP SQGYRRRRGRGQHRRGGVARAGSRGSRKRKRHTFCYSCGEDGHIRV QCINPSNLLLAKETKEILEGGEREAQTNSR | Human PNMA3 |
| 17 | GALTLLEDWCKGMDMDPRKALLIVGIPMECSEVEIQDTVKAGLQPLC AYRVLGRMERREDNAKAVFIELADTVNYTTLPSHIPGKGGSWEVVVK PRNPDDEFLSRLNYFLKDEGRSMTDVARALGCCSLPAESLDAEVMPQ VRSPPLEPPKESMWYRKLKVESGTASPSPGEETFEDWLEQVTEIMPIW QVSEVEKRRRLLESLRGPALSIMRNIQANNDSITVEQCLDALKQIFGD KEDFRASQPRFLQTSPKIGEKVSTFLLRLEPLLQKAVHKSPLSVRSTDM IRLKHLLARVAMTPALRGKLELLDQRGCPPNFLELIVIKLIRDEEEWEN TEAVMKNKEKPSGRGRGASGRQARAEASVSAPQATVQARSFSDSSPQ TIQGGLPPLVKRRRLLGSESTRGEDFIGQATYPKAENQTPGREGPQAA GEELGNEAGAGAMSHPKPWET | Human PNMA5 |
| 18 | GAVTMLQDWCRWMGVNARRGLIALGIPEDCDDAEFQESLEAALRPM GHFTVLGICAFREEDNATAALVELDREVNYALVPREIPGTGGPWNVVF VPRCSGEEFLGLGRVEHFPEQEGQMVESVAGALGVGLRRVCWLRSIG QAVQPWVEAVRCQSLGVFSGRDQPAPGEESFEVWLDHTTEMLHVW QGVSERERRRRLLEGLRGTALQLVHALLAENPARTAQDCLAALAQVF GDNESQATIRVKCLTAQQQSGERLSAFVLRLEVLLQKAMEKEALARA SADRVRLRQNILTRAHLTEPLDEALRKLRMAGRSPSFLEMLGLVRESE AWEASLARSVRAQTQEGAGARAGAQAVARASTKVEAVPGGPGREPE GLLQAGGQEAEELLQEGLKPVLEECDN | Human PNMA6A |
| 19 | GAVTMLQPWCRWMGVNARRGLLILGIPEDCDDAEFQESLEAALRPM GHFTVLGKVFREEDNATAALVELDREVWALVPREIPGTGGPWNVVF VPRCSGEEFLGLGRVFHPPEQEGQMVESVAGALGVGLRRVCWLRSIG QAVQPWVEAVRYQSLGVFSGRDQPAPGEESFEVWLDHTTEMLHVW QGVSERERRRRLLEGLRGTALQLVHALLAENPARTAQDCLAALAQVF GDNESQATERVKCLTAQQQSGERLSAFVLRLEVLLQKAMEKEALARA SADRVRLRQMLTRAHLTEPLDEALRKLRMAGRSPSFLEMLGLVRESE AWEASLARSVRAQTQEGAGARAGAQAVARASTKVEAVPGGPGREPE GLRQAGGQEAEELLQEGLKPVLEECDN | Human PNMA6B |
| 20 | GVEDLAASYIVLKLENEIRQAQVQWLMEENAALQAQIPELQKSQAAK EYDLLRKSSEAKEPQKLPEHMNPPAAWEAQKTPEFKEPQKPPEPQDL LPWEPPAAWELQEAPAAPESLAPPATRESQKPPMAHEIPTVLEGQGPA NTQDATIAQEPKNSEPQDPPNIEKNEAPEYQETAAQLEFLELPPPQEP LEPSNAQEFLELSAAQESLEGLIVVETSAASEPPQAPIGLEATDFPLQYT LTFSGDSQKLPEFLVQLYSYMRVRGHLYPTEAALVSFVGNCFSGRAG WWFQLLLDIQSPLLEQCESFIPVLQDTFDNPENNIKDANKIHQLCQGE GHVATHFHLIAQELNWDESTLWIQFQEGLASSIQDELSHTSPATNLSD LITQCISLEEKPDPNPLGKSSSAEGDGPESPPAENQPMQAAINCPHISEA ENVVRWHKGRLCINCGYPGHFARDCPVKPHQALQAGNIQACQ | Human RTL3 |
| 21 | GVQPQTSKAESPALAASPNAQMDDVIDTLTSLRLTNSALRREASTLRA EKANLTNMLESVMAELTLLRTRARIPGALQITPPISSITSNGTRPNFTTPP TSLPEPFSGDPGRLAGFLMQMDRFMIFQASRFPGEAERVAFLVSRLTG EAEKWAIPHMQPDSPLRNNYQGFLAELRRTYKSPLRHARRAQIRKTS ASNRAVRERQMLCRQLASAGTGPCPVHPASNGTSPAPALPARARNL | Human RTL6 |

Sequence listings provided herein

| SEQ ID NO: | Sequence | Origin |
|---|---|---|
| 22 | GDGRVQLMKALLAGPLRPAARRWRNPIPFPETFDGDTDRLPEFIVQTS SYMFVDENITSNDALKVTFUTRLTGPALQWVIPYTRKESPLLNDYRG FLAEMKRVFGWEEDEDF | Human RTL8A |
| 23 | GEGRVQLMKALLARPLRPAARRWRNPIPFPETFDGDTDRLPEFIVQTS SYMINDENTFSNDALKVTFLITRLTGPALQWVIPYIKKESPLLSDYRGF LAEMKRVFGWEEDEDF | Human RTL8B |
| 24 | GPRGRCRQQGPRIPIWAAANYANAHPWQQMDKASPGVAYIPINDP WIERPCCGDTVCVRTIMEQKSTASGTCGGKPAERGPLAGHMPSSRPH RVDFCWVPGSDPGTFDGSPWLLDRFLAQLGDYMSFHFEHYQDNISRV CEILRRLTGRAQAWAAPYLDGDLPLPDDYELFCQDLKEVVQDPNSFA EYHAVVTCPLPLASSQLPVAPQLPVVRQYLARFLEGLALDMGTAPRS LPAAMATPAVSGSNSVSRSALFEQQLTKESTPGPKEPPVLPSSTCSSKP GPVEPASSQPEEAAPTPVPRLSESANPPAQRPDPAHPGGPKPQKTEEEV LETEGDQEVSLGTNEVVEAPETPGEPPLSTGF | Human BOP |
| 25 | GVDELVLLLHALLMRHRALSIENSQLMEQLRLLVCERASLLRQVRPPS CPVPFPETFNGESSRLPEFIVQTASYMINNENRFCNDAMKVAFLISLLT GEAEEWVVPYIEMDSPILGDYRAFLDEMKQCFGWDDDEDDDEEEE DDY | Human LDOC 1 |
| 26 | GPVDLGQALGLLPSLAKAEDSQFSESDAALQEELSSPETARQLFRQFR YQVMSGPHETLKQLRKLCFQWLQPEVHTKEQILEILMLEQFLTILPGEI QMWVRKQCPGSGEEAVTLVESLKGDPQRLWQWISIQVLGQDILSEK MESPSCQVGEVEPHLEVVPQELGLENSSSGPGELLSHIVKEESDTEAEL ALAASQPARLEERLIRDQDLGASLLPAAPQEQWRQLDSTQKEQYWDL MLETYGKMVSGAGISHPKSDLTNSIEFGEELAGIYLHVNEKIPRPTCIG DRQENDKENLNLENHRDQELLHASCQASGEVPSQASLRGFFTEDEPG CFGEGENLPEALQNIQDEGTGEQLSPQERISEKQLGQIILPNPHSGEMS TMWLEEKRETSQKGQPRAPMAQKLPTCRECGKTFYRNSQLIFHQRTH TGETYFQCTICKKAFLRSSDFVKHQRTHTGEKPCKCDYCGKGFSDFSG LRHHEKIHTGEKPYKCPICEKSFIQRSNFNRHQRVHTGEKPYKCSHCG KSFSWSSSLDKHQRSHLGKKPFQ | Human ZNF18 |
| 27 | GTLRLLEDWCRGMDMNPRKALLIAGISQSCSVAEIEEALQAGLAPLGE YRLLGRMFRRDENRKVALVGLTAETSFIALVPKEIPGKGGIWRVIFKPP DPDNTFLSRLNEFLAGEGMTVGELSRALGHENGSLDPEQGMIPEMWA PMLNQALEALQPALQCLKYKKLRNTSGRESPEPGEEEFGRWMFHTTQ MIKAWQVPDVEKRRRLLESLRGPALDVIRVLKINNPLITVDECLQALE EVFGVTDNPRELQVKYLTMIKDEEKLSAYVLRLEPLLQKLVQRGAI ERDAVNQARLDQVIAGAVHKTIRRELNLPEDGPAPGFLQLLVLIKDYE AAEEEEALLQAILEGNFT | Human MOAP1 |
| 28 | GTERRRDELSEEINNLREKVMKQSEENNNLQSQVQKLIEENTTIREQ VEPTPEDEDDDIELRGAAAAAPPPPIEEECPEDLPEKFDGNPDMLAPF MAQCQJFMEKSTRDFSVDRVRVCFVTSMMTGRAARWASAKLERSHY LMHNYPAFMMEMKHVFEDPQRREVAKRKIRRLRQGMGSVIDYSNAF QMIAQDLDWNEPALIDQYHEGLSDHIQEELSHLEVAKSLSALIGQCIHI ERRLARAAAARKPRSPPRALVLPHIASHHQVDPTEPVGGARMRLTQE EKERRRKLNLCINCGTGGHYADNCPAKASKSSPAGKLPGPAVEGPSA TGPEIIRSPQDDASSPHLQVMLQIHLPGRHTLFVRAMIDSGASGNFIDH EYVAQNGIPLRIKDWPILVEAIDGRPIASGPVVHETHDLIVDLGDHREV LSFDVTQSPFFPVVLGVRWLSTHDPNITWSTRSIVFDSEYCRYHCRMY SPIPPSUPPAPQPPLYYPVDGYRVYQPVRMVQNVYTPVDEIWYPD HRINDPHIEMIPGAHSIPSGHVYSLSEPEMAALRDFVARNVKDGLITPT IAPNGAQVLQVKRGWKLQVSYDCRAPNNFTIQNQYPRLSIPNLEDQA HLATYTEFVPQIPGYQTYPTYAAYPTYPVGFAWYPVGRDGQGRSLYV PVMITWNPHWYRQPPVPQYPPPQPPPPPPPPPPPSYSTL | Human PEG10 |
| 29 | MELDHMTTGGLHAYPAPRGGPAAKPNVILQIGKCRAEMLEHVRRTH RHLLTEVSKQVERELKGLHRSVGKLENNLDGYVPTGDSQRWKKSIKA CLCRCQETIANLERWVKREMHVWREVFYRLERWADRLESMGGKYP VGSEPARHTVSVGVGGPEPYCQEADGYDYTVSPYAITPPPAAGELPEQ ESVEAQQYQSWGPGEDGQPSPGVDTQIFEDPREFLSHLEEYLRQVGGS EEYWLSQIQNHMNGPAKKWWEFKQGSVKNWVEFKKEFLQYSEGTL SREAIQRELELPQKQGEPLDQFLWRKRDLYQTLYVDAEEEDIQYVVG TLQPKLKRFLRHPLPKTLEQLIQRGMEVQDGLEQAAEPSGTPLPTEDE TEALTPALTSESVASDRTQPE | Mouse Arc |

-continued

Sequence listings provided herein

| SEQ ID NO: | Sequence | Origin |
|---|---|---|
| 30 | SYGFQPTNGVGYQPY | SARS-CoV-2 Spike |
| 31 | SQSIIAYTMSLGAEN | SARS-CoV-2 Spike |
| 32 | IPTNFTTSVTTEMP | SARS-CoV-2 Spike |
| 33 | AAAYYVGYLQPRTFL | SARS-CoV-2 Spike |
| 34 | APHGVVFLHVTYVPA | SARS-CoV-2 Spike |
| 35 | DGEVITFDNLKTLLS | SARS-CoV-2 ORFlab |
| 36 | EVRTIKVFTTVDNIN | SARS-CoV-2 ORFlab |
| 37 | IINLVQMAPISAMVR | SARS-CoV-2 ORFlab |
| 38 | NPTTFHLDGEVITFD | SARS-CoV-2 ORFlab |
| 39 | VAAIFYLITPVHVMS | SARS-CoV-2 ORFlab |
| 40 | IASFRLFARTRSMWS | SARS-CoV-2 Membrane |
| 41 | ATKAYNVTQAFGRRG | SARS-CoV-2 Nucleoprotein |
| 42 | VKPSFYVYSRVKNLN | SARS-CoV-2 Envelope |
| 43 | MFVFLVLLPLVSSQCVNLTTRTQLPPAYTNSFTRGVYYPDKVFRSSVL<br>HSTQDLFLPFFSNVTWFHAIHVSGTNGTKRFDNPVLPFNDGVYFASTE<br>KSNIIRGWIFGTTLDSKTQSLLIVNNATNVVIKVCEFQFCNDPFLGVYY<br>HKNNKSWMESEFRVYSSANNCTFEYVSQPFLMDLEGKQGNFKNLRE<br>FVFKNIDGYFKIYSKHTPINLVRDLPQGFSALEPLVDLPIGINITRFQTLL<br>ALHRSYLTPGDSSSGWTAGAAAYYVGYLQPRTFLLKYNENGTITDAV<br>DCALDPLSETKCTLKSFTVEKGIYQTSNFRVQPTESIVRFPNITNLCPFG<br>EVFNATRFASVYAWNRKRISNCVADYSVLYNSASFSTFKCYGVSPTK<br>LNDLCFTNVYADSFVIRGDEVRQIAPGQTGKIADYNYKLPDDFTGCVI<br>AWNSNNLDSKVGGNYNYLYRLFRKSNLKPFERDISTEIYQAGSTPCN<br>GVEGFNCYFPLQSYGFQPTNGVGYQPYRVVVLSFELLHAPATVCGPK<br>KSTNLVKNKCVNFNFNGLTGTGVLTESNKKFLPFQQFGRDIADTTDA<br>VRDPQTLEILDITPCSFGGVSVITPGTNTSNQVAVLYQDVNCTEVPVAI<br>HADQLTPTWRVYSTGSNVFQTRAGCLIGAEHVNNSYECDIPIGAGICA<br>SYQTQTNSPRRARSVASQSIIAYTMSLGAENSVAYSNNSIAIPTNFTISV<br>TTEILPVSMTKTSVDCTMYICGDSTECSNLLLQYGSFCTQLNRALTGIA<br>VEQDKNTQEVFAQVKQIYKTPPIKDFGGFNFSQILPDPSKPSKRSFIEDL<br>LFNKVTLADAGFIKQYGDCLGDIAARDLICAQKFNGLTVLPPLLTDEM<br>IAQYTSALLAGTITSGWTFGAGAALQIPFAMQMAYRFNGIGVTQNVL<br>YENQKLIANQFNSAIGKIQDSLSSTASALGKLQDVVNQNAQALNTLV<br>KQLSSNFGAISSVLNDILSRLDKVEAEVQIDRLITGRLQSLQTYVTQQLI<br>RAAEIRASANLAATKMSECVLGQSKRVDFCGKGYHLMSFPQSAPHG<br>VVFLHVTYVPAQEKNFTTAPAICHDGKAHFPREGVFVSNGTHWFVTQ<br>RNFYEPQIITTDNTFVSGNCDVVIGIVNNTVYDPLQPELDSFKEELDKY<br>FKNHTSPDVDLGDISGINASVVNIQKEIDRLNEVAKNLNESLIDLQELG<br>KYEQYIKWPWYIWLGFIAGLIAIVMVTIMLCCMTSCCSCLKGCCSCGS<br>CCKFDEDDSEPVLKGVKLHYT | SARS-CoV-2 Spike |

| Sequence listings provided herein | | |
|---|---|---|
| SEQ ID NO: | Sequence | Origin |
| 44 | MFIFLLFLTLTSGSDLDRCTTFDDVQAPNYTQHTSSMRGVYYPDEIFRS DTLYLTQDLFLPFYSNVTGFHTINHTFGNPVIPFKDGIYFAATEKSNVV RGWVFGSTMNNKSQSVIIINNSTNVVIRACNFELCDNPFFAVSKPMGT QTHTMIFDNAFNCTFEYISDAFSLDVSEKSGNFKHLREFVFKNKDGFL YVYKGYQPIDVVRDLPSGFNTLKPIFKLPLGINITNFRAILTAFSPAQDI WGTSAAAYFVGYLKPTTFMLKYDENGTITDAVDCSQNPLAELKCSV KSFEIDKGIYQTSNFRVVPSGDVVRFPNITNLCPFGEVFNATKFPSVYA WERKKISNCVADYSVLYNSTFFSTFKCYGVSATKLNDLCFSNVYADS FVVKGDDVRQIAPGQTGVIADYNYKLPDDFMGCVLAWNTRNIDATS TGNYNYKYRYLRHGKLRPFERDISNVPFSPDGKPCTPPALNCYWPLN DYGFYTTTGIGYQPYRVVVLSFELLNAPATVCGPKLSTDLIKNQCVNF NFNGLTGTGVLTPSSKRFQPFQQFGRDVSDFTDSVRDPKTSEILDISPC SFGGVSVITPGTNASSEVAVLYQDVNCTDVSTAIHADQLTPAWRIYST GNNVFQTQAGCLIGAEHVDTSYECDIPIGAGICASYHTVSLLRSTSQKS IVAYTMSLGADSSIAYSNNTIAIPTNFSISITTEVMPVSMAKTSVDCNM YICGDSTECANLLLQYGSFCTQLNRALSGIAAEQDRNTREVFAQVKQ MYKTPTLKYFGGFNFSQILPDPLKPTKRSFIEDLLFNKVTLADAGFMK QYGECLGDINARDLICAQKFNGLTVLPPLLTDDMIAAYTAALVSGTAT AGWTFGAGAALQIPFAMQMAYRFNGIGVTQNVLYENQKQIANQFNK AISQIQESLTTTSTALGKLQDVVNQNAQALNTLVKQLSSNFGAISSVL NDILSRLDKVEAEVQIDRLITGRLQSLQTYVTQQLIRAAEIRASANLAA TKMSECVLGQSKRVDFCGKGYHLMSFPQAAPHGVVFLHVTYVPSQE RNFTTAPAICHEGKAYFPREGVFVFNGTSWFITQRNFFSPQIITTDNTFV SGNCDVVIGIINNTVYDPLQPELDSFKEELDKYFKNHTSPDVDLGDISG INASVVNIQKEIDRLNEVAKNLNESLIDLQELGKYEQYIKWPWYVWL GFIAGLIAIVMVTILLCCMTSCCSCLKGACSCGSCCKFDEDDSEPVLKG VKLHYT | SARS-CoV-1 Spike |
| 45 | MSLLTEVETYVLSIIPSG

```
Arg Leu Glu Ser Thr Gly Gly Lys Tyr Pro Val Gly Ser Glu Ser Ala
130                 135                 140

Arg His Thr Val Ser Val Gly Val Gly Pro Glu Ser Tyr Cys His
145                 150                 155                 160

Glu Ala Asp Gly Tyr Asp Tyr Thr Val Ser Pro Tyr Ala Ile Thr Pro
                165                 170                 175

Pro Pro Ala Ala Gly Glu Leu Pro Gly Gln Glu Pro Ala Glu Ala Gln
                180                 185                 190

Gln Tyr Gln Pro Trp Val Pro Gly Glu Asp Gly Gln Pro Ser Pro Gly
                195                 200                 205

Val Asp Thr Gln Ile Phe Glu Asp Pro Arg Glu Phe Leu Ser His Leu
210                 215                 220

Glu Glu Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Phe
                245                 250                 255

Lys Gln Gly Ser Val Lys Asn Trp Val Glu Phe Lys Lys Glu Phe Leu
                260                 265                 270

Gln Tyr Ser Glu Gly Thr Leu Ser Arg Glu Ala Ile Gln Arg Glu Leu
                275                 280                 285

Asp Leu Pro Gln Lys Gln Gly Glu Pro Leu Asp Gln Phe Leu Trp Arg
290                 295                 300

Lys Arg Asp Leu Tyr Gln Thr Leu Tyr Val Asp Ala Asp Glu Glu Glu
305                 310                 315                 320

Ile Ile Gln Tyr Val Val Gly Thr Leu Gln Pro Lys Leu Lys Arg Phe
                325                 330                 335

Leu Arg His Pro Leu Pro Lys Thr Leu Glu Gln Leu Ile Gln Arg Gly
                340                 345                 350

Met Glu Val Gln Asp Asp Leu Glu Gln Ala Ala Glu Pro Ala Gly Pro
                355                 360                 365

His Leu Pro Val Glu Asp Glu Ala Glu Thr Leu Thr Pro Ala Pro Asn
                370                 375                 380

Ser Glu Ser Val Ala Ser Asp Arg Thr Gln Pro Glu
385                 390                 395

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000
```

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<211> LENGTH: 455
<212> TYPE: PRT
<213> ORGANISM: Homo sapiens -continued

<400> SEQUENCE: 16

```
Gly Pro Leu Thr Leu Leu Gln Asp Trp Cys Arg Gly Glu His Leu Asn
1               5                   10                  15

Thr Arg Arg Cys Met Leu Ile Leu Gly Ile Pro Glu Asp Cys Gly Glu
            20                  25                  30

Asp Glu Phe Glu Glu Thr Leu Gln Glu Ala Cys Arg His Leu Gly Arg
        35                  40                  45

Tyr Arg Val Ile Gly Arg Met Phe Arg Glu Glu Asn Ala Gln Ala
    50                  55                  60

Ile Leu Leu Glu Leu Ala Gln Asp Ile Asp Tyr Ala Leu Leu Pro Arg
65                  70                  75                  80

Glu Ile Pro Gly Lys Gly Pro Trp Glu Val Ile Lys Pro Arg
                85                  90                  95

Asn Ser Asp Gly Glu Phe Leu Asn Arg Leu Asn Arg Phe Leu Glu Glu
                100                 105                 110

Glu Arg Arg Thr Val Ser Asp Met Asn Arg Val Leu Gly Ser Asp Thr
            115                 120                 125

Asn Cys Ser Ala Pro Arg Val Thr Ile Ser Pro Glu Phe Trp Thr Trp
130                 135                 140

Ala Gln Thr Leu Gly Ala Ala Val Gln Pro Leu Glu Gln Met Leu
145                 150                 155                 160

Tyr Arg Glu Leu Arg Val Phe Ser Gly Asn Thr Ile Ser Ile Pro Gly
                165                 170                 175

Ala Leu Ala Phe Asp Ala Trp Leu Glu His Thr Thr Glu Met Leu Gln
                180                 185                 190

Met Trp Gln Val Pro Glu Gly Glu Lys Arg Arg Arg Leu Met Glu Cys
            195                 200                 205

Leu Arg Gly Pro Ala Leu Gln Val Val Ser Gly Leu Arg Ala Ser Asn
210                 215                 220

Ala Ser Ile Thr Val Glu Glu Cys Leu Ala Ala Leu Gln Gln Val Phe
225                 230                 235                 240

Gly Pro Val Glu Ser His Lys Ile Ala Gln Val Lys Leu Cys Lys Ala
                245                 250                 255

Tyr Gln Glu Ala Gly Glu Lys Val Ser Ser Phe Val Leu Arg Leu Glu
                260                 265                 270

Pro Leu Leu Gln Arg Ala Val Glu Asn Asn Val Val Ser Arg Arg Asn
            275                 280                 285

Val Asn Gln Thr Arg Leu Lys Arg Val Leu Ser Gly Ala Thr Leu Pro
290                 295                 300

Asp Lys Leu Arg Asp Lys Leu Lys Leu Met Lys Gln Arg Arg Lys Pro
305                 310                 315                 320

Pro Gly Phe Leu Ala Leu Val Lys Leu Leu Arg Glu Glu Glu Trp
                325                 330                 335

Glu Ala Thr Leu Gly Pro Asp Arg Glu Ser Leu Glu Gly Leu Glu Val
            340                 345                 350

Ala Pro Arg Pro Pro Ala Arg Ile Thr Gly Val Gly Ala Val Pro Leu
                355                 360                 365

Pro Ala Ser Gly Asn Ser Phe Asp Ala Arg Pro Ser Gln Gly Tyr Arg
            370                 375                 380

Arg Arg Arg Gly Arg Gly Gln His Arg Gly Gly Val Ala Arg Ala
385                 390                 395                 400

Gly Ser Arg Gly Ser Arg Lys Arg Lys Arg His Thr Phe Cys Tyr Ser
                405                 410                 415
```

```
Cys Gly Glu Asp Gly His Ile Arg Val Gln Cys Ile Asn Pro Ser Asn
                420                 425                 430

Leu Leu Leu Ala Lys Glu Thr Lys Glu Ile Leu Glu Gly Gly Glu Arg
            435                 440                 445

Glu Ala Gln Thr Asn Ser Arg
        450                 455

<210> SEQ ID NO 17
<211> LENGTH: 448
<212> TYPE: PRT
<213> ORGANISM: Homo sapiens

<400> SEQUENCE: 17

Gly Ala Leu Thr Leu Leu Glu Asp Trp Cys Lys Gly Met Asp Met Asp
1               5                   10                  15

Pro Arg Lys Ala Leu Leu Ile Val Gly Ile Pro Met Glu Cys Ser Glu
            20                  25                  30

Val Glu Ile Gln Asp Thr Val Lys Ala Gly Leu Gln Pro Leu Cys Ala
        35                  40                  45

Tyr Arg Val Leu Gly Arg Met Phe Arg Arg Glu Asp Asn Ala Lys Ala
    50                  55                  60

Val Phe Ile Glu Leu Ala Asp Thr Val Asn Tyr Thr Thr Leu Pro Ser
65                  70                  75                  80

His Ile Pro Gly Lys Gly Gly Ser Trp Glu Val Val Lys Pro Arg
                85                  90                  95

Asn Pro Asp Asp Glu Phe Leu Ser Arg Leu Asn Tyr Phe Leu Lys Asp
            100                 105                 110

Glu Gly Arg Ser Met Thr Asp Val Ala Arg Ala Leu Gly Cys Cys Ser
        115                 120                 125

Leu Pro Ala Glu Ser Leu Asp Ala Glu Val Met Pro Gln Val Arg Ser
    130                 135                 140

Pro Pro Leu Glu Pro Pro Lys Glu Ser Met Trp Tyr Arg Lys Leu Lys
145                 150                 155                 160

Val Phe Ser Gly Thr Ala Ser Pro Ser Pro Gly Glu Glu Thr Phe Glu
                165                 170                 175

Asp Trp Leu Glu Gln Val Thr Glu Ile Met Pro Ile Trp Gln Val Ser
            180                 185                 190

Glu Val Glu Lys Arg Arg Arg Leu Leu Glu Ser Leu Arg Gly Pro Ala
        195                 200                 205

Leu Ser Ile Met Arg Val Leu Gln Ala Asn Asn Asp Ser Ile Thr Val
    210                 215                 220

Glu Gln Cys Leu Asp Ala Leu Lys Gln Ile Phe Gly Asp Lys Glu Asp
225                 230                 235                 240

Phe Arg Ala Ser Gln Phe Arg Phe Leu Gln Thr Ser Pro Lys Ile Gly
                245                 250                 255

Glu Lys Val Ser Thr Phe Leu Leu Arg Leu Glu Pro Leu Leu Gln Lys
            260                 265                 270

Ala Val His Lys Ser Pro Leu Ser Val Arg Ser Thr Asp Met Ile Arg
        275                 280                 285

Leu Lys His Leu Leu Ala Arg Val Ala Met Thr Pro Ala Leu Arg Gly
    290                 295                 300

Lys Leu Glu Leu Asp Gln Arg Gly Cys Pro Pro Asn Phe Leu Glu
305                 310                 315                 320

Leu Met Lys Leu Ile Arg Asp Glu Glu Glu Trp Glu Asn Thr Glu Ala
                325                 330                 335
```

Val Met Lys Asn Lys Glu Lys Pro Ser Gly Arg Gly Arg Gly Ala Ser
            340                 345                 350

Gly Arg Gln Ala Arg Ala Glu Ala Ser Val Ser Ala Pro Gln Ala Thr
            355                 360                 365

Val Gln Ala Arg Ser Phe Ser Asp Ser Ser Pro Gln Thr Ile Gln Gly
            370                 375                 380

Gly Leu Pro Pro Leu Val Lys Arg Arg Leu Leu Gly Ser Glu Ser
385                 390                 395                 400

Thr Arg Gly Glu Asp His Gly Gln Ala Thr Tyr Pro Lys Ala Glu Asn
            405                 410                 415

Gln Thr Pro Gly Arg Glu Gly Pro Gln Ala Ala Gly Glu Leu Gly
            420                 425                 430

Asn Glu Ala Gly Ala Gly Ala Met Ser His Pro Lys Pro Trp Glu Thr
            435                 440                 445

<210> SEQ ID NO 18
<211> LENGTH: 399
<212> TYPE: PRT
<213> ORGANISM: Homo sapiens

<400> SEQUENCE: 18

Gly Ala Val Thr Met Leu Gln Asp Trp Cys Arg Trp Met Gly Val Asn
1               5                   10                  15

Ala Arg Arg Gly Leu Leu Ile Leu Gly Ile Pro Glu Asp Cys Asp Asp
            20                  25                  30

Ala Glu Phe Gln Glu Ser Leu Glu Ala Ala Leu Arg Pro Met Gly His
            35                  40                  45

Phe Thr Val Leu Gly Lys Ala Phe Arg Glu Glu Asp Asn Ala Thr Ala
50                  55                  60

Ala Leu Val Glu Leu Asp Arg Glu Val Asn Tyr Ala Leu Val Pro Arg
65                  70                  75                  80

Glu Ile Pro Gly Thr Gly Gly Pro Trp Asn Val Val Phe Val Pro Arg
            85                  90                  95

Cys Ser Gly Glu Glu Phe Leu Gly Leu Gly Arg Val Phe His Phe Pro
            100                 105                 110

Glu Gln Glu Gly Gln Met Val Glu Ser Val Ala Gly Ala Leu Gly Val
            115                 120                 125

Gly Leu Arg Arg Val Cys Trp Leu Arg Ser Ile Gly Gln Ala Val Gln
            130                 135                 140

Pro Trp Val Glu Ala Val Arg Cys Gln Ser Leu Gly Val Phe Ser Gly
145                 150                 155                 160

Arg Asp Gln Pro Ala Pro Gly Glu Glu Ser Phe Glu Val Trp Leu Asp
            165                 170                 175

His Thr Thr Glu Met Leu His Val Trp Gln Gly Val Ser Glu Arg Glu
            180                 185                 190

Arg Arg Arg Arg Leu Leu Glu Gly Leu Arg Gly Thr Ala Leu Gln Leu
            195                 200                 205

Val His Ala Leu Leu Ala Glu Asn Pro Ala Arg Thr Ala Gln Asp Cys
            210                 215                 220

Leu Ala Ala Leu Ala Gln Val Phe Gly Asp Asn Glu Ser Gln Ala Thr
225                 230                 235                 240

Ile Arg Val Lys Cys Leu Thr Ala Gln Gln Ser Gly Glu Arg Leu
            245                 250                 255

Ser Ala Phe Val Leu Arg Leu Glu Val Leu Leu Gln Lys Ala Met Glu
            260                 265                 270

```
Lys Glu Ala Leu Ala Arg Ala Ser Ala Asp Arg Val Arg Leu Arg Gln
            275                 280                 285

Met Leu Thr Arg Ala His Leu Thr Glu Pro Leu Asp Glu Ala Leu Arg
        290                 295                 300

Lys Leu Arg Met Ala Gly Arg Ser Pro Ser Phe Leu Glu Met Leu Gly
305                 310                 315                 320

Leu Val Arg Glu Ser Glu Ala Trp Glu Ala Ser Leu Ala Arg Ser Val
                325                 330                 335

Arg Ala Gln Thr Gln Glu Gly Ala Ala Arg Ala Gly Ala Gln Ala
            340                 345                 350

Val Ala Arg Ala Ser Thr Lys Val Glu Ala Val Pro Gly Gly Pro Gly
            355                 360                 365

Arg Glu Pro Glu Gly Leu Leu Gln Ala Gly Gln Glu Ala Glu Glu
    370                 375                 380

Leu Leu Gln Glu Gly Leu Lys Pro Val Leu Glu Cys Asp Asn
385                 390                 395
```

<210> SEQ ID NO 19
<211> LENGTH: 399
<212> TYPE: PRT
<213> ORGANISM: Homo sapiens

<400> SEQUENCE: 19

```
Gly Ala Val Thr Met Leu Gln Asp Trp Cys Arg Trp Met Gly Val Asn
1               5                   10                  15

Ala Arg Arg Gly Leu Leu Ile Leu Gly Ile Pro Glu Asp Cys Asp Asp
            20                  25                  30

Ala Glu Phe Gln Glu Ser Leu Glu Ala Ala Leu Arg Pro Met Gly His
        35                  40                  45

Phe Thr Val Leu Gly Lys Val Phe Arg Glu Glu Asp Asn Ala Thr Ala
    50                  55                  60

Ala Leu Val Glu Leu Asp Arg Glu Val Asn Tyr Ala Leu Val Pro Arg
65                  70                  75                  80

Glu Ile Pro Gly Thr Gly Gly Pro Trp Asn Val Val Phe Val Pro Arg
                85                  90                  95

Cys Ser Gly Glu Glu Phe Leu Gly Leu Gly Arg Val Phe His Phe Pro
            100                 105                 110

Glu Gln Glu Gly Gln Met Val Glu Ser Val Ala Gly Ala Leu Gly Val
        115                 120                 125

Gly Leu Arg Arg Val Cys Trp Leu Arg Ser Ile Gly Gln Ala Val Gln
    130                 135                 140

Pro Trp Val Glu Ala Val Arg Tyr Gln Ser Leu Gly Val Phe Ser Gly
145                 150                 155                 160

Arg Asp Gln Pro Ala Pro Gly Glu Glu Ser Phe Glu Val Trp Leu Asp
                165                 170                 175

His Thr Thr Glu Met Leu His Val Trp Gln Gly Val Ser Glu Arg Glu
            180                 185                 190

Arg Arg Arg Arg Leu Leu Glu Gly Leu Arg Gly Thr Ala Leu Gln Leu
        195                 200                 205

Val His Ala Leu Leu Ala Glu Asn Pro Ala Arg Thr Ala Gln Asp Cys
    210                 215                 220

Leu Ala Ala Leu Ala Gln Val Phe Gly Asp Asn Glu Ser Gln Ala Thr
225                 230                 235                 240

Ile Arg Val Lys Cys Leu Thr Ala Gln Gln Ser Gly Glu Arg Leu
                245                 250                 255
```

Ser Ala Phe Val Leu Arg Leu Glu Val Leu Gln Lys Ala Met Glu
                260                 265                 270

Lys Glu Ala Leu Ala Arg Ala Ser Ala Asp Arg Val Arg Leu Arg Gln
            275                 280                 285

Met Leu Thr Arg Ala His Leu Thr Glu Pro Leu Asp Glu Ala Leu Arg
    290                 295                 300

Lys Leu Arg Met Ala Gly Arg Ser Pro Ser Phe Leu Glu Met Leu Gly
305                 310                 315                 320

Leu Val Arg Glu Ser Glu Ala Trp Glu Ala Ser Leu Ala Arg Ser Val
                325                 330                 335

Arg Ala Gln Thr Gln Glu Gly Ala Gly Ala Arg Ala Gly Ala Gln Ala
            340                 345                 350

Val Ala Arg Ala Ser Thr Lys Val Glu Ala Val Pro Gly Gly Pro Gly
    355                 360                 365

Arg Glu Pro Glu Gly Leu Arg Gln Ala Gly Gln Glu Ala Glu Glu
370                 375                 380

Leu Leu Gln Glu Gly Leu Lys Pro Val Leu Glu Glu Cys Asp Asn
385                 390                 395

<210> SEQ ID NO 20
<211> LENGTH: 475
<212> TYPE: PRT
<213> ORGANISM: Homo sapiens

<400> SEQUENCE: 20

Gly Val Glu Asp Leu Ala Ala Ser Tyr Ile Val Leu Lys Leu Glu Asn
1               5                   10                  15

Glu Ile Arg Gln Ala Gln Val Gln Trp Leu Met Glu Glu Asn Ala Ala
            20                  25                  30

Leu Gln Ala Gln Ile Pro Glu Leu Gln Lys Ser Gln Ala Ala Lys Glu
        35                  40                  45

Tyr Asp Leu Leu Arg Lys Ser Ser Glu Ala Lys Glu Pro Gln Lys Leu
    50                  55                  60

Pro Glu His Met Asn Pro Pro Ala Ala Trp Glu Ala Gln Lys Thr Pro
65                  70                  75                  80

Glu Phe Lys Glu Pro Gln Lys Pro Pro Glu Pro Gln Asp Leu Leu Pro
                85                  90                  95

Trp Glu Pro Pro Ala Ala Trp Glu Leu Gln Glu Ala Pro Ala Ala Pro
            100                 105                 110

Glu Ser Leu Ala Pro Pro Ala Thr Arg Glu Ser Gln Lys Pro Pro Met
        115                 120                 125

Ala His Glu Ile Pro Thr Val Leu Glu Gly Gln Gly Pro Ala Asn Thr
    130                 135                 140

Gln Asp Ala Thr Ile Ala Gln Glu Pro Lys Asn Ser Glu Pro Gln Asp
145                 150                 155                 160

Pro Pro Asn Ile Glu Lys Pro Gln Glu Ala Pro Glu Tyr Gln Glu Thr
                165                 170                 175

Ala Ala Gln Leu Glu Phe Leu Glu Leu Pro Pro Gln Glu Pro Leu
            180                 185                 190

Glu Pro Ser Asn Ala Gln Glu Phe Leu Glu Leu Ser Ala Ala Gln Glu
        195                 200                 205

Ser Leu Glu Gly Leu Ile Val Val Glu Thr Ser Ala Ala Ser Glu Phe
    210                 215                 220

Pro Gln Ala Pro Ile Gly Leu Glu Ala Thr Asp Phe Pro Leu Gln Tyr
225                 230                 235                 240

Thr Leu Thr Phe Ser Gly Asp Ser Gln Lys Leu Pro Glu Phe Leu Val
                245                 250                 255

Gln Leu Tyr Ser Tyr Met Arg Val Arg Gly His Leu Tyr Pro Thr Glu
            260                 265                 270

Ala Ala Leu Val Ser Phe Val Gly Asn Cys Phe Ser Gly Arg Ala Gly
        275                 280                 285

Trp Trp Phe Gln Leu Leu Leu Asp Ile Gln Ser Pro Leu Leu Glu Gln
    290                 295                 300

Cys Glu Ser Phe Ile Pro Val Leu Gln Asp Thr Phe Asp Asn Pro Glu
305                 310                 315                 320

Asn Met Lys Asp Ala Asn Gln Cys Ile His Gln Leu Cys Gln Gly Glu
                325                 330                 335

Gly His Val Ala Thr His Phe His Leu Ile Ala Gln Glu Leu Asn Trp
            340                 345                 350

Asp Glu Ser Thr Leu Trp Ile Gln Phe Gln Glu Gly Leu Ala Ser Ser
        355                 360                 365

Ile Gln Asp Glu Leu Ser His Thr Ser Pro Ala Thr Asn Leu Ser Asp
    370                 375                 380

Leu Ile Thr Gln Cys Ile Ser Leu Glu Glu Lys Pro Asp Pro Asn Pro
385                 390                 395                 400

Leu Gly Lys Ser Ser Ala Glu Gly Asp Gly Pro Glu Ser Pro Pro
                405                 410                 415

Ala Glu Asn Gln Pro Met Gln Ala Ala Ile Asn Cys Pro His Ile Ser
            420                 425                 430

Glu Ala Glu Trp Val Arg Trp His Lys Gly Arg Leu Cys Leu Tyr Cys
        435                 440                 445

Gly Tyr Pro Gly His Phe Ala Arg Asp Cys Pro Val Lys Pro His Gln
    450                 455                 460

Ala Leu Gln Ala Gly Asn Ile Gln Ala Cys Gln
465                 470                 475

<210> SEQ ID NO 21
<211> LENGTH: 239
<212> TYPE: PRT
<213> ORGANISM: Homo sapiens

<400> SEQUENCE: 21

Gly Val Gln Pro Gln Thr Ser Lys Ala Glu Ser Pro Ala Leu Ala Ala
1               5                   10                  15

Ser Pro Asn Ala Gln Met Asp Asp Val Ile Asp Thr Leu Thr Ser Leu
            20                  25                  30

Arg Leu Thr Asn Ser Ala Leu Arg Arg Glu Ala Ser Thr Leu Arg Ala
        35                  40                  45

Glu Lys Ala Asn Leu Thr Asn Met Leu Glu Ser Val Met Ala Glu Leu
    50                  55                  60

Thr Leu Leu Arg Thr Arg Ala Arg Ile Pro Gly Ala Leu Gln Ile Thr
65                  70                  75                  80

Pro Pro Ile Ser Ser Ile Thr Ser Asn Gly Thr Arg Pro Met Thr Thr
                85                  90                  95

Pro Pro Thr Ser Leu Pro Glu Pro Phe Ser Gly Asp Pro Gly Arg Leu
            100                 105                 110

Ala Gly Phe Leu Met Gln Met Asp Arg Phe Met Ile Phe Gln Ala Ser
        115                 120                 125

Arg Phe Pro Gly Glu Ala Glu Arg Val Ala Phe Leu Val Ser Arg Leu
    130                 135                 140

```
Thr Gly Glu Ala Glu Lys Trp Ala Ile Pro His Met Gln Pro Asp Ser
145                 150                 155                 160

Pro Leu Arg Asn Asn Tyr Gln Gly Phe Leu Ala Glu Leu Arg Arg Thr
            165                 170                 175

Tyr Lys Ser Pro Leu Arg His Ala Arg Arg Ala Gln Ile Arg Lys Thr
        180                 185                 190

Ser Ala Ser Asn Arg Ala Val Arg Glu Arg Gln Met Leu Cys Arg Gln
    195                 200                 205

Leu Ala Ser Ala Gly Thr Gly Pro Cys Pro Val His Pro Ala Ser Asn
210                 215                 220

Gly Thr Ser Pro Ala Pro Ala Leu Pro Ala Arg Ala Arg Asn Leu
225                 230                 235

<210> SEQ ID NO 22
<211> LENGTH: 113
<212> TYPE: PRT
<213> ORGANISM: Homo sapiens

<400> SEQUENCE: 22

Gly Asp Gly Arg Val Gln Leu Met Lys Ala Leu Leu Ala Gly Pro Leu
1               5                   10                  15

Arg Pro Ala Ala Arg Arg Trp Arg Asn Pro Ile Pro Phe Pro Glu Thr
            20                  25                  30

Phe Asp Gly Asp Thr Asp Arg Leu Pro Glu Phe Ile Val Gln Thr Ser
        35                  40                  45

Ser Tyr Met Phe Val Asp Glu Asn Thr Phe Ser Asn Asp Ala Leu Lys
    50                  55                  60

Val Thr Phe Leu Ile Thr Arg Leu Thr Gly Pro Ala Leu Gln Trp Val
65              70                  75                  80

Ile Pro Tyr Ile Arg Lys Glu Ser Pro Leu Leu Asn Asp Tyr Arg Gly
            85                  90                  95

Phe Leu Ala Glu Met Lys Arg Val Phe Gly Trp Glu Glu Asp Glu Asp
        100                 105                 110

Phe

<210> SEQ ID NO 23
<211> LENGTH: 113
<212> TYPE: PRT
<213> ORGANISM: Homo sapiens

<400> SEQUENCE: 23

Gly Glu Gly Arg Val Gln Leu Met Lys Ala Leu Leu Ala Arg Pro Leu
1               5                   10                  15

Arg Pro Ala Ala Arg Arg Trp Arg Asn Pro Ile Pro Phe Pro Glu Thr
            20                  25                  30

Phe Asp Gly Asp Thr Asp Arg Leu Pro Glu Phe Ile Val Gln Thr Ser
        35                  40                  45

Ser Tyr Met Phe Val Asp Glu Asn Thr Phe Ser Asn Asp Ala Leu Lys
    50                  55                  60

Val Thr Phe Leu Ile Thr Arg Leu Thr Gly Pro Ala Leu Gln Trp Val
65              70                  75                  80

Ile Pro Tyr Ile Lys Lys Glu Ser Pro Leu Leu Ser Asp Tyr Arg Gly
            85                  90                  95

Phe Leu Ala Glu Met Lys Arg Val Phe Gly Trp Glu Glu Asp Glu Asp
        100                 105                 110

Phe
```

```
<210> SEQ ID NO 24
<211> LENGTH: 364
<212> TYPE: PRT
<213> ORGANISM: Homo sapiens

<400> SEQUENCE: 24

Gly Pro Arg Gly Arg Cys Arg Gln Gln Gly Pro Arg Ile Pro Ile Trp
1               5                   10                  15

Ala Ala Ala Asn Tyr Ala Asn Ala His Pro Trp Gln Gln Met Asp Lys
            20                  25                  30

Ala Ser Pro Gly Val Ala Tyr Thr Pro Leu Val Asp Pro Trp Ile Glu
        35                  40                  45

Arg Pro Cys Cys Gly Asp Thr Val Cys Val Arg Thr Thr Met Glu Gln
    50                  55                  60

Lys Ser Thr Ala Ser Gly Thr Cys Gly Gly Lys Pro Ala Glu Arg Gly
65                  70                  75                  80

Pro Leu Ala Gly His Met Pro Ser Ser Arg Pro His Arg Val Asp Phe
                85                  90                  95

Cys Trp Val Pro Gly Ser Asp Pro Gly Thr Phe Asp Gly Ser Pro Trp
            100                 105                 110

Leu Leu Asp Arg Phe Leu Ala Gln Leu Gly Asp Tyr Met Ser Phe His
        115                 120                 125

Phe Glu His Tyr Gln Asp Asn Ile Ser Arg Val Cys Glu Ile Leu Arg
    130                 135                 140

Arg Leu Thr Gly Arg Ala Gln Ala Trp Ala Ala Pro Tyr Leu Asp Gly
145                 150                 155                 160

Asp Leu Pro Leu Pro Asp Asp Tyr Glu Leu Phe Cys Gln Asp Leu Lys
                165                 170                 175

Glu Val Val Gln Asp Pro Asn Ser Phe Ala Glu Tyr His Ala Val Val
            180                 185                 190

Thr Cys Pro Leu Pro Leu Ala Ser Ser Gln Leu Pro Val Ala Pro Gln
        195                 200                 205

Leu Pro Val Val Arg Gln Tyr Leu Ala Arg Phe Leu Glu Gly Leu Ala
    210                 215                 220

Leu Asp Met Gly Thr Ala Pro Arg Ser Leu Pro Ala Ala Met Ala Thr
225                 230                 235                 240

Pro Ala Val Ser Gly Ser Asn Ser Val Ser Arg Ser Ala Leu Phe Glu
                245                 250                 255

Gln Gln Leu Thr Lys Glu Ser Thr Pro Gly Pro Lys Glu Pro Pro Val
            260                 265                 270

Leu Pro Ser Ser Thr Cys Ser Ser Lys Pro Gly Pro Val Glu Pro Ala
        275                 280                 285

Ser Ser Gln Pro Glu Glu Ala Pro Thr Pro Val Pro Arg Leu Ser
    290                 295                 300

Glu Ser Ala Asn Pro Pro Ala Gln Arg Pro Asp Pro Ala His Pro Gly
305                 310                 315                 320

Gly Pro Lys Pro Gln Lys Thr Glu Glu Val Leu Glu Thr Glu Gly
                325                 330                 335

Asp Gln Glu Val Ser Leu Gly Thr Pro Gln Glu Val Val Glu Ala Pro
            340                 345                 350

Glu Thr Pro Gly Glu Pro Pro Leu Ser Pro Gly Phe
        355                 360
```

```
<210> SEQ ID NO 25
<211> LENGTH: 146
<212> TYPE: PRT
<213> ORGANISM: Homo sapiens

<400> SEQUENCE: 25

Gly Val Asp Glu Leu Val Leu Leu His Ala Leu Leu Met Arg His
1               5                   10                  15

Arg Ala Leu Ser Ile Glu Asn Ser Gln Leu Met Glu Gln Leu Arg Leu
                20                  25                  30

Leu Val Cys Glu Arg Ala Ser Leu Leu Arg Gln Val Arg Pro Pro Ser
                35                  40                  45

Cys Pro Val Pro Phe Pro Glu Thr Phe Asn Gly Glu Ser Ser Arg Leu
        50                  55                  60

Pro Glu Phe Ile Val Gln Thr Ala Ser Tyr Met Leu Val Asn Glu Asn
65                  70                  75                  80

Arg Phe Cys Asn Asp Ala Met Lys Val Ala Phe Leu Ile Ser Leu Leu
                85                  90                  95

Thr Gly Glu Ala Glu Glu Trp Val Val Pro Tyr Ile Glu Met Asp Ser
                100                 105                 110

Pro Ile Leu Gly Asp Tyr Arg Ala Phe Leu Asp Glu Met Lys Gln Cys
            115                 120                 125

Phe Gly Trp Asp Asp Asp Asp Glu Asp Asp Asp Glu Glu Glu Glu Asp
    130                 135                 140

Asp Tyr
145

<210> SEQ ID NO 26
<211> LENGTH: 549
<212> TYPE: PRT
<213> ORGANISM: Homo sapiens

<400> SEQUENCE: 26

Gly Pro Val Asp Leu Gly Gln Ala Leu Gly Leu Leu Pro Ser Leu Ala
1               5                   10                  15

Lys Ala Glu Asp Ser Gln Phe Ser Glu Ser Asp Ala Ala Leu Gln Glu
                20                  25                  30

Glu Leu Ser Ser Pro Glu Thr Ala Arg Gln Leu Phe Arg Gln Phe Arg
                35                  40                  45

Tyr Gln Val Met Ser Gly Pro His Glu Thr Leu Lys Gln Leu Arg Lys
    50                  55                  60

Leu Cys Phe Gln Trp Leu Gln Pro Glu Val His Thr Lys Glu Gln Ile
65              70                  75                  80

Leu Glu Ile Leu Met Leu Glu Gln Phe Leu Thr Ile Leu Pro Gly Glu
                85                  90                  95

Ile Gln Met Trp Val Arg Lys Gln Cys Pro Gly Ser Gly Glu Glu Ala
                100                 105                 110

Val Thr Leu Val Glu Ser Leu Lys Gly Asp Pro Gln Arg Leu Trp Gln
            115                 120                 125

Trp Ile Ser Ile Gln Val Leu Gly Gln Asp Ile Leu Ser Glu Lys Met
    130                 135                 140

Glu Ser Pro Ser Cys Gln Val Gly Glu Val Glu Pro His Leu Glu Val
145                 150                 155                 160

Val Pro Gln Glu Leu Gly Leu Glu Asn Ser Ser Gly Pro Gly Glu
                165                 170                 175
```

```
Leu Leu Ser His Ile Val Lys Glu Glu Ser Asp Thr Glu Ala Glu Leu
            180                 185                 190
Ala Leu Ala Ala Ser Gln Pro Ala Arg Leu Glu Glu Arg Leu Ile Arg
        195                 200                 205
Asp Gln Asp Leu Gly Ala Ser Leu Leu Pro Ala Ala Pro Gln Glu Gln
    210                 215                 220
Trp Arg Gln Leu Asp Ser Thr Gln Lys Glu Gln Tyr Trp Asp Leu Met
225                 230                 235                 240
Leu Glu Thr Tyr Gly Lys Met Val Ser Gly Ala Gly Ile Ser His Pro
                245                 250                 255
Lys Ser Asp Leu Thr Asn Ser Ile Glu Phe Gly Glu Glu Leu Ala Gly
            260                 265                 270
Ile Tyr Leu His Val Asn Glu Lys Ile Pro Arg Pro Thr Cys Ile Gly
        275                 280                 285
Asp Arg Gln Glu Asn Asp Lys Glu Asn Leu Asn Leu Glu Asn His Arg
    290                 295                 300
Asp Gln Glu Leu Leu His Ala Ser Cys Gln Ala Ser Gly Glu Val Pro
305                 310                 315                 320
Ser Gln Ala Ser Leu Arg Gly Phe Phe Thr Glu Asp Glu Pro Gly Cys
                325                 330                 335
Phe Gly Glu Gly Glu Asn Leu Pro Glu Ala Leu Gln Asn Ile Gln Asp
            340                 345                 350
Glu Gly Thr Gly Glu Gln Leu Ser Pro Gln Glu Arg Ile Ser Glu Lys
        355                 360                 365
Gln Leu Gly Gln His Leu Pro Asn Pro His Ser Gly Glu Met Ser Thr
    370                 375                 380
Met Trp Leu Glu Glu Lys Arg Glu Thr Ser Gln Lys Gly Gln Pro Arg
385                 390                 395                 400
Ala Pro Met Ala Gln Lys Leu Pro Thr Cys Arg Glu Cys Gly Lys Thr
                405                 410                 415
Phe Tyr Arg Asn Ser Gln Leu Ile Phe His Gln Arg Thr His Thr Gly
            420                 425                 430
Glu Thr Tyr Phe Gln Cys Thr Ile Cys Lys Lys Ala Phe Leu Arg Ser
        435                 440                 445
Ser Asp Phe Val Lys His Gln Arg Thr His Thr Gly Glu Lys Pro Cys
    450                 455                 460
Lys Cys Asp Tyr Cys Gly Lys Gly Phe Ser Asp Phe Ser Gly Leu Arg
465                 470                 475                 480
His His Glu Lys Ile His Thr Gly Glu Lys Pro Tyr Lys Cys Pro Ile
                485                 490                 495
Cys Glu Lys Ser Phe Ile Gln Arg Ser Asn Phe Asn Arg His Gln Arg
            500                 505                 510
Val His Thr Gly Glu Lys Pro Tyr Lys Cys Ser His Cys Gly Lys Ser
        515                 520                 525
Phe Ser Trp Ser Ser Ser Leu Asp Lys His Gln Arg Ser His Leu Gly
    530                 535                 540
Lys Lys Pro Phe Gln
545

<210> SEQ ID NO 27
<211> LENGTH: 351
<212> TYPE: PRT
<213> ORGANISM: Homo sapiens
```

-continued

```
<400> SEQUENCE: 27

Gly Thr Leu Arg Leu Leu Glu Asp Trp Cys Arg Gly Met Asp Met Asn
1               5                   10                  15

Pro Arg Lys Ala Leu Leu Ile Ala Gly Ile Ser Gln Ser Cys Ser Val
            20                  25                  30

Ala Glu Ile Glu Glu Ala Leu Gln Ala Gly Leu Ala Pro Leu Gly Glu
        35                  40                  45

Tyr Arg Leu Leu Gly Arg Met Phe Arg Arg Asp Glu Asn Arg Lys Val
    50                  55                  60

Ala Leu Val Gly Leu Thr Ala Glu Thr Ser His Ala Leu Val Pro Lys
65                  70                  75                  80

Glu Ile Pro Gly Lys Gly Ile Trp Arg Val Ile Phe Lys Pro Pro
                85                  90                  95

Asp Pro Asp Asn Thr Phe Leu Ser Arg Leu Asn Glu Phe Leu Ala Gly
            100                 105                 110

Glu Gly Met Thr Val Gly Glu Leu Ser Arg Ala Leu Gly His Glu Asn
        115                 120                 125

Gly Ser Leu Asp Pro Glu Gln Gly Met Ile Pro Glu Met Trp Ala Pro
130                 135                 140

Met Leu Ala Gln Ala Leu Glu Ala Leu Gln Pro Ala Leu Gln Cys Leu
145                 150                 155                 160

Lys Tyr Lys Lys Leu Arg Val Phe Ser Gly Arg Glu Ser Pro Glu Pro
                165                 170                 175

Gly Glu Glu Glu Phe Gly Arg Trp Met Phe His Thr Thr Gln Met Ile
            180                 185                 190

Lys Ala Trp Gln Val Pro Asp Val Glu Lys Arg Arg Arg Leu Leu Glu
        195                 200                 205

Ser Leu Arg Gly Pro Ala Leu Asp Val Ile Arg Val Leu Lys Ile Asn
    210                 215                 220

Asn Pro Leu Ile Thr Val Asp Glu Cys Leu Gln Ala Leu Glu Glu Val
225                 230                 235                 240

Phe Gly Val Thr Asp Asn Pro Arg Glu Leu Gln Val Lys Tyr Leu Thr
                245                 250                 255

Thr Tyr His Lys Asp Glu Glu Lys Leu Ser Ala Tyr Val Leu Arg Leu
            260                 265                 270

Glu Pro Leu Leu Gln Lys Leu Val Gln Arg Gly Ala Ile Glu Arg Asp
        275                 280                 285

Ala Val Asn Gln Ala Arg Leu Asp Gln Val Ile Ala Gly Ala Val His
    290                 295                 300

Lys Thr Ile Arg Arg Glu Leu Asn Leu Pro Glu Asp Gly Pro Ala Pro
305                 310                 315                 320

Gly Phe Leu Gln Leu Leu Val Leu Ile Lys Asp Tyr Glu Ala Ala Glu
                325                 330                 335

Glu Glu Glu Ala Leu Leu Gln Ala Ile Leu Glu Gly Asn Phe Thr
            340                 345                 350

<210> SEQ ID NO 28
<211> LENGTH: 708
<212> TYPE: PRT
<213> ORGANISM: Homo sapiens
```

```
<400> SEQUENCE: 28

Gly Thr Glu Arg Arg Asp Glu Leu Ser Glu Glu Ile Asn Asn Leu
1               5                   10                  15

Arg Glu Lys Val Met Lys Gln Ser Glu Glu Asn Asn Asn Leu Gln Ser
            20                  25                  30

Gln Val Gln Lys Leu Thr Glu Asn Thr Thr Leu Arg Glu Gln Val
        35                  40                  45

Glu Pro Thr Pro Glu Asp Glu Asp Asp Ile Glu Leu Arg Gly Ala
    50                  55                  60

Ala Ala Ala Ala Pro Pro Pro Ile Glu Glu Glu Cys Pro Glu
65                  70                  75                  80

Asp Leu Pro Glu Lys Phe Asp Gly Asn Pro Asp Met Leu Ala Pro Phe
                85                  90                  95

Met Ala Gln Cys Gln Ile Phe Met Glu Lys Ser Thr Arg Asp Phe Ser
            100                 105                 110

Val Asp Arg Val Arg Val Cys Phe Val Thr Ser Met Met Thr Gly Arg
        115                 120                 125

Ala Ala Arg Trp Ala Ser Ala Lys Leu Glu Arg Ser His Tyr Leu Met
130                 135                 140

His Asn Tyr Pro Ala Phe Met Met Glu Met Lys His Val Phe Glu Asp
145                 150                 155                 160

Pro Gln Arg Arg Glu Val Ala Lys Arg Lys Ile Arg Arg Leu Arg Gln
                165                 170                 175

Gly Met Gly Ser Val Ile Asp Tyr Ser Asn Ala Phe Gln Met Ile Ala
            180                 185                 190

Gln Asp Leu Asp Trp Asn Glu Pro Ala Leu Ile Asp Gln Tyr His Glu
        195                 200                 205

Gly Leu Ser Asp His Ile Gln Glu Leu Ser His Leu Glu Val Ala
    210                 215                 220

Lys Ser Leu Ser Ala Leu Ile Gly Gln Cys Ile His Ile Glu Arg Arg
225                 230                 235                 240

Leu Ala Arg Ala Ala Ala Arg Lys Pro Arg Ser Pro Pro Arg Ala
                245                 250                 255

Leu Val Leu Pro His Ile Ala Ser His His Gln Val Asp Pro Thr Glu
                260                 265                 270

Pro Val Gly Gly Ala Arg Met Arg Leu Thr Gln Glu Glu Lys Glu Arg
            275                 280                 285

Arg Arg Lys Leu Asn Leu Cys Leu Tyr Cys Gly Thr Gly Gly His Tyr
        290                 295                 300

Ala Asp Asn Cys Pro Ala Lys Ala Ser Lys Ser Ser Pro Ala Gly Lys
305                 310                 315                 320

Leu Pro Gly Pro Ala Val Glu Gly Pro Ser Ala Thr Gly Pro Glu Ile
                325                 330                 335

Ile Arg Ser Pro Gln Asp Asp Ala Ser Ser Pro His Leu Gln Val Met
                340                 345                 350

Leu Gln Ile His Leu Pro Gly Arg His Thr Leu Phe Val Arg Ala Met
        355                 360                 365

Ile Asp Ser Gly Ala Ser Gly Asn Phe Ile Asp His Glu Tyr Val Ala
370                 375                 380

Gln Asn Gly Ile Pro Leu Arg Ile Lys Asp Trp Pro Ile Leu Val Glu
385                 390                 395                 400

Ala Ile Asp Gly Arg Pro Ile Ala Ser Gly Pro Val Val His Glu Thr
                405                 410                 415
```

```
His Asp Leu Ile Val Asp Leu Gly Asp His Arg Glu Val Leu Ser Phe
            420                 425                 430

Asp Val Thr Gln Ser Pro Phe Phe Pro Val Val Leu Gly Val Arg Trp
            435                 440                 445

Leu Ser Thr His Asp Pro Asn Ile Thr Trp Ser Thr Arg Ser Ile Val
450                 455                 460

Phe Asp Ser Glu Tyr Cys Arg Tyr His Cys Arg Met Tyr Ser Pro Ile
465                 470                 475                 480

Pro Pro Ser Leu Pro Pro Ala Pro Gln Pro Pro Leu Tyr Tyr Pro
                485                 490                 495

Val Asp Gly Tyr Arg Val Tyr Gln Pro Val Arg Tyr Tyr Val Gln
            500                 505                 510

Asn Val Tyr Thr Pro Val Asp Glu His Val Tyr Pro Asp His Arg Leu
            515                 520                 525

Val Asp Pro His Ile Glu Met Ile Pro Gly Ala His Ser Ile Pro Ser
530                 535                 540

Gly His Val Tyr Ser Leu Ser Glu Pro Glu Met Ala Ala Leu Arg Asp
545                 550                 555                 560

Phe Val Ala Arg Asn Val Lys Asp Gly Leu Ile Thr Pro Thr Ile Ala
                565                 570                 575

Pro Asn Gly Ala Gln Val Leu Gln Val Lys Arg Gly Trp Lys Leu Gln
            580                 585                 590

Val Ser Tyr Asp Cys Arg Ala Pro Asn Asn Phe Thr Ile Gln Asn Gln
            595                 600                 605

Tyr Pro Arg Leu Ser Ile Pro Asn Leu Glu Asp Gln Ala His Leu Ala
610                 615                 620

Thr Tyr Thr Glu Phe Val Pro Gln Ile Pro Gly Tyr Gln Thr Tyr Pro
625                 630                 635                 640

Thr Tyr Ala Ala Tyr Pro Thr Tyr Pro Val Gly Phe Ala Trp Tyr Pro
                645                 650                 655

Val Gly Arg Asp Gly Gln Gly Arg Ser Leu Tyr Val Pro Val Met Ile
            660                 665                 670

Thr Trp Asn Pro His Trp Tyr Arg Gln Pro Pro Val Pro Gln Tyr Pro
            675                 680                 685

Pro Pro Gln Pro Pro Pro Pro Pro Pro Pro Pro Pro Pro Pro Pro Ser
690                 695                 700

Tyr Ser Thr Leu
705

<210> SEQ ID NO 29
<211> LENGTH: 396
<212> TYPE: PRT
<213> ORGANISM: Mus sp.

<400> SEQUENCE: 29

Met Glu Leu Asp His Met Thr Thr Gly Gly Leu His Ala Tyr Pro Ala
1               5                   10                  15

Pro Arg Gly Gly Pro Ala Ala Lys Pro Asn Val Ile Leu Gln Ile Gly
            20                  25                  30

Lys Cys Arg Ala Glu Met Leu Glu His Val Arg Arg Thr His Arg His
        35                  40                  45

Leu Leu Thr Glu Val Ser Lys Gln Val Glu Arg Glu Leu Lys Gly Leu
    50                  55                  60

His Arg Ser Val Gly Lys Leu Glu Asn Asn Leu Asp Gly Tyr Val Pro
65                  70                  75                  80
```

```
Thr Gly Asp Ser Gln Arg Trp Lys Lys Ser Ile Lys Ala Cys Leu Cys
                85                  90                  95
Arg Cys Gln Glu Thr Ile Ala Asn Leu Glu Arg Trp Val Lys Arg Glu
            100                 105                 110
Met His Val Trp Arg Glu Val Phe Tyr Arg Leu Glu Arg Trp Ala Asp
        115                 120                 125
Arg Leu Glu Ser Met Gly Gly Lys Tyr Pro Val Gly Ser Glu Pro Ala
    130                 135                 140
Arg His Thr Val Ser Val Gly Val Gly Pro Glu Pro Tyr Cys Gln
145                 150                 155                 160
Glu Ala Asp Gly Tyr Asp Tyr Thr Val Ser Pro Tyr Ala Ile Thr Pro
                165                 170                 175
Pro Pro Ala Ala Gly Glu Leu Pro Glu Gln Glu Ser Val Glu Ala Gln
            180                 185                 190
Gln Tyr Gln Ser Trp Gly Pro Gly Glu Asp Gly Gln Pro Ser Pro Gly
        195                 200                 205
Val Asp Thr Gln Ile Phe Glu Asp Pro Arg Glu Phe Leu Ser His Leu
    210                 215                 220
Glu Glu Tyr Leu Arg Gln Val Gly Gly Ser Glu Glu Tyr Trp Leu Ser
225                 230                 235                 240
Gln Ile Gln Asn His Met Asn Gly Pro Ala Lys Lys Trp Trp Glu Phe
                245                 250                 255
Lys Gln Gly Ser Val Lys Asn Trp Val Glu Phe Lys Lys Glu Phe Leu
            260                 265                 270
Gln Tyr Ser Glu Gly Thr Leu Ser Arg Glu Ala Ile Gln Arg Glu Leu
        275                 280                 285
Glu Leu Pro Gln Lys Gln Gly Glu Pro Leu Asp Gln Phe Leu Trp Arg
    290                 295                 300
Lys Arg Asp Leu Tyr Gln Thr Leu Tyr Val Asp Ala Glu Glu Glu
305                 310                 315                 320
Ile Ile Gln Tyr Val Val Gly Thr Leu Gln Pro Lys Leu Lys Arg Phe
                325                 330                 335
Leu Arg His Pro Leu Pro Lys Thr Leu Glu Gln Leu Ile Gln Arg Gly
            340                 345                 350
Met Glu Val Gln Asp Gly Leu Glu Gln Ala Ala Glu Pro Ser Gly Thr
        355                 360                 365
Pro Leu Pro Thr Glu Asp Glu Thr Glu Ala Leu Thr Pro Ala Leu Thr
    370                 375                 380
Ser Glu Ser Val Ala Ser Asp Arg Thr Gln Pro Glu
385                 390                 395

<210> SEQ ID NO 30
<211> LENGTH: 15
<212> TYPE: PRT
<213> ORGANISM: Severe acute respiratory syndrome coronavirus 2

<400> SEQUENCE: 30

Ser Tyr Gly Phe Gln Pro Thr Asn Gly Val Gly Tyr Gln Pro Tyr
1               5                   10                  15

<210> SEQ ID NO 31
<211> LENGTH: 15
<212> TYPE: PRT
<213> ORGANISM: Severe acute respiratory syndrome coronavirus 2
```

```
<400> SEQUENCE: 31

Ser Gln Ser Ile Ile Ala Tyr Thr Met Ser Leu Gly Ala Glu Asn
1               5                   10                  15

<210> SEQ ID NO 32
<211> LENGTH: 15
<212> TYPE: PRT
<213> ORGANISM: Severe acute respiratory syndrome coronavirus 2

<400> SEQUENCE: 32

Ile Pro Thr Asn Phe Thr Ile Ser Val Thr Thr Glu Ile Leu Pro
1               5                   10                  15

<210> SEQ ID NO 33
<211> LENGTH: 15
<212> TYPE: PRT
<213> ORGANISM: Severe acute respiratory syndrome coronavirus 2

<400> SEQUENCE: 33

Ala Ala Ala Tyr Tyr Val Gly Tyr Leu Gln Pro Arg Thr Phe Leu
1               5                   10                  15

<210> SEQ ID NO 34
<211> LENGTH: 15
<212> TYPE: PRT
<213> ORGANISM: Severe acute respiratory syndrome coronavirus 2

<400> SEQUENCE: 34

Ala Pro His Gly Val Val Phe Leu His Val Thr Tyr Val Pro Ala
1               5                   10                  15

<210> SEQ ID NO 35
<211> LENGTH: 15
<212> TYPE: PRT
<213> ORGANISM: Severe acute respiratory syndrome coronavirus 2

<400> SEQUENCE: 35

Asp Gly Glu Val Ile Thr Phe Asp Asn Leu Lys Thr Leu Leu Ser
1               5                   10                  15

<210> SEQ ID NO 36
<211> LENGTH: 15
<212> TYPE: PRT
<213> ORGANISM: Severe acute respiratory syndrome coronavirus 2

<400> SEQUENCE: 36

Glu Val Arg Thr Ile Lys Val Phe Thr Thr Val Asp Asn Ile Asn
1               5                   10                  15

<210> SEQ ID NO 37
<211> LENGTH: 15
<212> TYPE: PRT
<213> ORGANISM: Severe acute respiratory syndrome coronavirus 2

<400> SEQUENCE: 37

Ile Ile Asn Leu Val Gln Met Ala Pro Ile Ser Ala Met Val Arg
1               5                   10                  15

<210> SEQ ID NO 38
<211> LENGTH: 15
<212> TYPE: PRT
<213> ORGANISM: Severe acute respiratory syndrome coronavirus 2
```

```
<400> SEQUENCE: 38

Asn Pro Thr Thr Phe His Leu Asp Gly Glu Val Ile Thr Phe Asp
1               5                   10                  15

<210> SEQ ID NO 39
<211> LENGTH: 15
<212> TYPE: PRT
<213> ORGANISM: Severe acute respiratory syndrome coronavirus 2

<400> SEQUENCE: 39

Val Ala Ala Ile Phe Tyr Leu Ile Thr Pro Val His Val Met Ser
1               5                   10                  15

<210> SEQ ID NO 40
<211> LENGTH: 15
<212> TYPE: PRT
<213> ORGANISM: Severe acute respiratory syndrome coronavirus 2

<400> SEQUENCE: 40

Ile Ala Ser Phe Arg Leu Phe Ala Arg Thr Arg Ser Met Trp Ser
1               5                   10                  15

<210> SEQ ID NO 41
<211> LENGTH: 15
<212> TYPE: PRT
<213> ORGANISM: Severe acute respiratory syndrome coronavirus 2

<400> SEQUENCE: 41

Ala Thr Lys Ala Tyr Asn Val Thr Gln Ala Phe Gly Arg Arg Gly
1               5                   10                  15

<210> SEQ ID NO 42
<211> LENGTH: 15
<212> TYPE: PRT
<213> ORGANISM: Severe acute respiratory syndrome coronavirus 2

<400> SEQUENCE: 42

Val Lys Pro Ser Phe Tyr Val Tyr Ser Arg Val Lys Asn Leu Asn
1               5                   10                  15

<210> SEQ ID NO 43
<211> LENGTH: 1273
<212> TYPE: PRT
<213> ORGANISM: Severe acute respiratory syndrome coronavirus 2

<400> SEQUENCE: 43

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110
```

-continued

```
Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525
```

```
Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940
```

```
Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 44
<211> LENGTH: 1255
<212> TYPE: PRT
<213> ORGANISM: Severe acute respiratory syndrome coronavirus 2

<400> SEQUENCE: 44

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30
```

-continued

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
 50                  55                  60

Asn Val Thr Gly Phe His Thr Ile Asn His Thr Phe Gly Asn Pro Val
65                   70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

```
Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
                515                 520                 525

Phe Asn Gly Leu Thr Gly Thr Gly Val Leu Thr Pro Ser Ser Lys Arg
530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
                690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
850                 855                 860
```

```
Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
        900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
        980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255
```

```
<210> SEQ ID NO 45
<211> LENGTH: 252
<212> TYPE: PRT
<213> ORGANISM: Influenza A virus

<400> SEQUENCE: 45

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ser Gly Ser Gly Ser Gly Ser Gly Ser
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 47

His His His His His His
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ser Gly Ser Gly Ser
1               5
```

What is claimed is:

1. A composition comprising: 1) an ARC polypeptide or an endogenous gag (endo-gag) polypeptide; 2) a pathogen-associated antigen; and 3) an adjuvant.

2. The composition of claim 1, wherein the composition comprises the ARC polypeptide, wherein the ARC polypeptide comprises:
an amino acid sequence that is SEQ ID NO: 1 or an amino acid sequence that is at least 90% identical to the SEQ ID NO: 1.

3. The composition of claim 1, wherein composition comprises the endo-gag polypeptide, wherein the endo-gag polypeptide comprises:
   a) an amino acid sequence that is SEQ ID NO: 16 or an amino acid sequence that is at least 90% identical to the SEQ ID NO: 16;
   b) an amino acid sequence that is SEQ ID NO: 17 or an amino acid sequence that is at least 90% identical to the SEQ ID NO: 17;
   c) an amino acid sequence that is SEQ ID NO: 18 or an amino acid sequence that is at least 90% identical to the SEQ ID NO: 18;
   d) an amino acid sequence that is SEQ ID NO: 19 or an amino acid sequence that is at least 90% identical to the SEQ ID NO: 19;
   e) an amino acid sequence that is SEQ ID NO: 20 or an amino acid sequence that is at least 90% identical to the SEQ ID NO: 20;
   f) an amino acid sequence that is SEQ ID NO: 21 or an amino acid sequence that is at least 90% identical to the SEQ ID NO: 21;
   g) an amino acid sequence that is SEQ ID NO: 22 or an amino acid sequence that is at least 90% identical to the SEQ ID NO: 22;
   h) an amino acid sequence that is SEQ ID NO: 23 or an amino acid sequence that is at least 90% identical to the SEQ ID NO: 23;
   i) an amino acid sequence that is SEQ ID NO: 24 or an amino acid sequence that is at least 90% identical to the SEQ ID NO: 24;
   j an amino acid sequence that is SEQ ID NO: 25 or an amino acid sequence that is at least 90% identical to the SEQ ID NO: 25;
   k) an amino acid sequence that is SEQ ID NO: 26 or an amino acid sequence that is at least 90% identical to the SEQ ID NO: 26;
   l) an amino acid sequence that is SEQ ID NO: 27 or an amino acid sequence that is at least 90% identical to the SEQ ID NO: 27;
   m) an amino acid sequence that is SEQ ID NO: 28 or an amino acid sequence that is at least 90% identical to the SEQ ID NO: 28; or
   n) any combination thereof.

4. The composition of claim 1, wherein the pathogen-associated antigen comprises a polypeptide antigen.

5. The composition of claim 1, wherein the pathogen-associated antigen is a bacterial antigen, a fungal antigen, a parasitic antigen, or a viral antigen.

6. The composition of claim 5, wherein the composition comprises the viral antigen, wherein the viral antigen is a Coronaviridae antigen.

7. The composition of claim 6, wherein the viral antigen comprises an amino acid residue sequence as set forth in any one of SEQ ID NOs: 30 to 42, and combinations thereof.

8. The composition of claim 5, wherein composition comprises the viral antigen, wherein the viral antigen is an Influenza antigen.

9. The composition of claim 1, wherein the ARC polypeptide or the endo-gag polypeptide is coupled to the pathogen-associated antigen.

10. The composition of claim 9, wherein the ARC polypeptide or the endo-gag polypeptide is coupled to the pathogen-associated antigen by a peptide bond.

11. The composition of claim 1, wherein the adjuvant comprises an immune stimulatory compound.

12. The composition of claim 11, wherein the immune stimulatory compound comprises a lipid, a nucleic acid, an aluminum compound, a water-in-oil emulsion, a polypeptide, or any combination thereof.

13. The composition of claim 1, wherein the adjuvant is coupled to the ARC polypeptide or the endo-gag polypeptide.

14. The composition of claim 1, wherein the composition further comprises a virus-like particle.

15. The composition of claim 14, wherein the virus-like particle comprises: (a) a mixture of the ARC polypeptide or the endo-gag polypeptide coupled to the pathogen-associated antigen; and (b) the ARC polypeptide or the endo-gag polypeptide coupled to the adjuvant.

16. The composition of claim 15, wherein the virus-like particle further comprises the ARC polypeptide or the endo-gag polypeptide not coupled to the adjuvant or the pathogen-associated antigen.

17. The composition of claim 1, further comprising a pharmaceutically acceptable excipient, carrier, or diluent.

18. A method of priming an adaptive immune response to a pathogen-associated antigen in an individual comprising administering the composition of claim 1 to the individual, thereby priming the adaptive immune response to the pathogen-associated antigen.

19. The method of claim 18, wherein the individual is a human individual.

20. The method of claim 18, wherein the adaptive immune response is an antibody response to the pathogen-associated antigen.

21. The method of claim 20, wherein the antibody response produces IgG antibodies that specifically bind the pathogen-associated antigen.

22. The method of claim 18, wherein the adaptive immune response is a cellular immune response to the pathogen-associated antigen.

23. A method of vaccinating an individual comprising administering the composition of claim 1 to the individual, thereby vaccinating the individual.

* * * * *